United States Patent
Davidson et al.

(10) Patent No.: US 9,487,779 B2
(45) Date of Patent: Nov. 8, 2016

(54) SIRNA-MEDIATED GENE SILENCING

(71) Applicant: University of Iowa Research Foundation, Iowa City, IA (US)

(72) Inventors: Beverly L. Davidson, Iowa City, IA (US); Henry Paulson, Iowa City, IA (US); Victor Miller, Iowa City, IA (US); Cynthia Gouvion, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/297,378

(22) Filed: Jun. 5, 2014

(65) Prior Publication Data

US 2016/0040159 A1   Feb. 11, 2016

Related U.S. Application Data

(63) Continuation of application No. 13/668,739, filed on Nov. 5, 2012, now Pat. No. 8,779,116, and a continuation of application No. 12/952,449, filed on Nov. 23, 2010, now Pat. No. 8,329,890, and a continuation of application No. 10/738,642, filed on Dec. 16, 2003, now abandoned, and a continuation-in-part of application No. PCT/US03/16887, filed on May 6, 2003, and a continuation-in-part of application No. 10/430,351, filed on May 5, 2003, now abandoned, and a continuation of application No. 10/322,086, filed on Dec. 17, 2002, now abandoned, and a continuation-in-part of application No. 10/212,322, filed on Aug. 5, 2002, now abandoned.

(51) Int. Cl.
| | |
|---|---|
| C07H 21/04 | (2006.01) |
| C12N 15/113 | (2010.01) |
| C12N 15/11 | (2006.01) |
| A61K 38/00 | (2006.01) |
| A61K 48/00 | (2006.01) |

(52) U.S. Cl.
CPC ........... *C12N 15/113* (2013.01); *C12N 15/111* (2013.01); *C12N 15/1137* (2013.01); *C12Y 302/01031* (2013.01); *A01K 2217/05* (2013.01); *A61K 38/00* (2013.01); *A61K 48/00* (2013.01); *C12N 2310/111* (2013.01); *C12N 2310/14* (2013.01); *C12N 2310/53* (2013.01); *C12N 2330/30* (2013.01); *C12N 2799/021* (2013.01); *C12N 2799/022* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 4,873,192 | A | 10/1989 | Kunkel |
| 4,962,091 | A | 10/1990 | Eppstein et al. |
| 5,350,674 | A | 9/1994 | Boenisch et al. |
| 5,580,859 | A | 12/1996 | Felgner et al. |
| 5,585,362 | A | 12/1996 | Wilson et al. |
| 5,686,288 | A | 11/1997 | MacDonald et al. |
| 5,814,500 | A | 9/1998 | Dietz |
| 5,837,449 | A | 11/1998 | Monia et al. |
| 5,849,995 | A | 12/1998 | Hayden et al. |
| 5,902,880 | A | 5/1999 | Thompson |
| 5,922,602 | A | 7/1999 | Kumagai et al. |
| 5,928,906 | A | 7/1999 | Koster et al. |
| 5,972,704 | A | 10/1999 | Draper et al. |
| 6,001,990 | A | 12/1999 | Wands et al. |
| 6,177,246 | B1 | 1/2001 | Monia et al. |
| 6,387,616 | B1 | 5/2002 | Ozelius et al. |
| 6,420,345 | B1 | 7/2002 | Patel et al. |
| 6,468,524 | B1 | 10/2002 | Chiorini et al. |
| 6,479,291 | B2 | 11/2002 | Kumagai et al. |
| 6,506,559 | B1 | 1/2003 | Driver et al. |
| 6,531,647 | B1 | 3/2003 | Baulcombe et al. |
| 6,573,099 | B2 | 6/2003 | Graham |
| 6,596,535 | B1 | 7/2003 | Carter |
| 6,794,414 | B1 | 9/2004 | Steinman |
| 6,852,535 | B1 | 2/2005 | Thompson |
| 7,186,552 | B2 | 3/2007 | Wilson et al. |
| 7,902,352 | B2 | 3/2011 | Kaemmerer et al. |
| 8,227,592 | B2 | 7/2012 | Harper et al. |
| 8,258,286 | B2 | 9/2012 | Davidson et al. |
| 8,329,890 | B2 | 12/2012 | Davidson et al. |
| 8,481,710 | B2 | 7/2013 | Davidson et al. |
| 8,487,088 | B2 | 7/2013 | Davidson et al. |
| 8,524,881 | B2 | 9/2013 | Davidson et al. |
| 8,691,567 | B2 | 4/2014 | Harper et al. |
| 8,779,116 | B2 | 7/2014 | Davidson et al. |
| 2002/0086356 | A1 | 7/2002 | Tuschl et al. |
| 2002/0132788 | A1 | 9/2002 | Lewis et al. |

(Continued)

FOREIGN PATENT DOCUMENTS

| | | |
|---|---|---|
| DE | 10100586 | 4/2002 |
| DE | 10100588 | 7/2002 |

(Continued)

OTHER PUBLICATIONS

Abdallah et al., "Non-viral gene transfer: Applications in developmental biology and gene therapy," *Biol. Cell*, 1995, 85:1-7.
Abdelgany et al., "Allele-specific silencing of a pathogenic mutant acetylcholine receptor subunit by RNA interference," *Hum. Mol. Genet.*, 2003, 12(20):2637-2644.
Adelman et al., "In Vitro Deletional Mutagenesis for Bacterial Production of the 20,000-Dalton Form of Human Pituitary Growth Hormone," *DNA*, 1983, 2(3):183-193.

(Continued)

*Primary Examiner* — Kimberly Chong
(74) *Attorney, Agent, or Firm* — Viksnins Harris & Padys PLLP

(57) ABSTRACT

The present invention is directed to small interfering RNA molecules (siRNA) targeted against an allele of interest, and methods of using these siRNA molecules.

20 Claims, 35 Drawing Sheets

(56) References Cited

U.S. PATENT DOCUMENTS

| | | |
|---|---|---|
| 2002/0173478 A1 | 11/2002 | Gewirtz |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0108923 A1 | 6/2003 | Tuschl et al. |
| 2003/0143732 A1 | 7/2003 | Fosnaugh et al. |
| 2003/0148519 A1 | 8/2003 | Engelke et al. |
| 2003/0165853 A1 | 9/2003 | Partridge et al. |
| 2004/0023390 A1 | 2/2004 | Davidson et al. |
| 2004/0053875 A1 | 3/2004 | Kreutzer et al. |
| 2004/0086860 A1 | 5/2004 | Sohail |
| 2004/0096843 A1 | 5/2004 | Rossi et al. |
| 2004/0192629 A1 | 9/2004 | Xu et al. |
| 2004/0241854 A1 | 12/2004 | Davidson et al. |
| 2005/0042646 A1 | 2/2005 | Davidson et al. |
| 2005/0074887 A1 | 4/2005 | Rossi et al. |
| 2005/0096284 A1 | 5/2005 | McSwiggen |
| 2005/0106731 A1 | 5/2005 | Davidson et al. |
| 2005/0186586 A1 | 8/2005 | Zamore et al. |
| 2005/0196862 A1 | 9/2005 | Wooddell et al. |
| 2005/0197315 A1 | 9/2005 | Taira et al. |
| 2005/0255086 A1 | 11/2005 | Davidson et al. |
| 2006/0009408 A1 | 1/2006 | Davidson et al. |
| 2006/0257912 A1 | 11/2006 | Kaemmerer et al. |
| 2008/0176812 A1 | 7/2008 | Davidson et al. |
| 2008/0274989 A1 | 11/2008 | Davidson et al. |
| 2009/0036395 A1 | 2/2009 | Davidson et al. |
| 2009/0105169 A1 | 4/2009 | Davidson et al. |
| 2010/0008981 A1 | 1/2010 | Kaemmerer et al. |
| 2010/0144026 A1 | 6/2010 | Davidson et al. |
| 2010/0190243 A1 | 7/2010 | Davidson et al. |
| 2010/0325746 A9 | 12/2010 | Kaemmerer et al. |
| 2011/0111491 A1 | 5/2011 | Davidson et al. |
| 2011/0212520 A1 | 9/2011 | Davidson et al. |
| 2011/0244562 A1 | 10/2011 | Davidson et al. |
| 2012/0270317 A1 | 10/2012 | Harper et al. |
| 2012/0283424 A1 | 11/2012 | Davidson et al. |
| 2014/0163214 A1 | 6/2014 | Davidson et al. |
| 2014/0179003 A1 | 6/2014 | Harper et al. |
| 2014/0287492 A1 | 9/2014 | Davidson et al. |
| 2014/0303362 A1 | 10/2014 | Davidson et al. |

FOREIGN PATENT DOCUMENTS

| | | |
|---|---|---|
| EP | 1 144 623 | 10/2001 |
| EP | 1 214 945 | 6/2002 |
| WO | WO 90/14090 | 11/1990 |
| WO | WO 94/01550 | 1/1994 |
| WO | WO 94/07529 | 4/1994 |
| WO | WO 99/32619 | 7/1999 |
| WO | WO 99/49029 | 9/1999 |
| WO | WO 00/44895 | 8/2000 |
| WO | WO 01/29058 | 4/2001 |
| WO | WO 01/49844 | 7/2001 |
| WO | WO 01/70949 | 9/2001 |
| WO | WO 01/75164 | 10/2001 |
| WO | WO 02/44321 | 6/2002 |
| WO | WO 02/055692 | 7/2002 |
| WO | WO 02/055693 | 7/2002 |
| WO | WO 03/006477 | 1/2003 |
| WO | WO 03/008573 | 1/2003 |
| WO | WO 03/010180 | 2/2003 |
| WO | WO 03/022052 | 3/2003 |
| WO | WO 03/023015 | 3/2003 |
| WO | WO 03/048362 | 6/2003 |
| WO | WO 03/080807 | 10/2003 |
| WO | WO 2004/013280 | 2/2004 |
| WO | WO 2004/013355 | 2/2004 |
| WO | WO 2004/042027 | 5/2004 |
| WO | WO 2004/047872 | 6/2004 |
| WO | WO 2004/058940 | 7/2004 |
| WO | WO 2005/105995 | 11/2005 |
| WO | WO 2006/031267 | 3/2006 |
| WO | WO 2006/083800 | 8/2006 |

OTHER PUBLICATIONS

Agrawal, "Antisense oligonucleotides: towards clinical trials," *TIBTech.*, 1996, 14:376-387.

Alisky and Davidson, "Gene Therapy for Amyotrophic Lateral Sclerosis and Other Motor Neuron Diseases," *Hum. Gen. Ther.*, 2000, 11:2315-2329.

Alisky et al., "Transduction of murine cerebellar neurons with recombinant FIV and AAV5 vectors," *NeuroReport*, 2000, 11(12):2669-2673.

Alisky et al., "Towards therapy using RNA interference", *Am J Pharmacogenomics*, 4(1):45-51 (2004).

Altschul et al., "Basic Local Alignment Search Tool," *J. Mol. Biol.*, 1990, 215:403-410.

Altschul et al., "Gapped BLAST and PSI-BLAST: a new generation of protein database search programs," *Nucl. Acids Res.*, 1997, 25(17):3389-3402.

Ambrose et al., "Structure and Expression of the Huntington's Disease Gene: Evidence against Simple Inactivation Due to an Expanded CAG Repeat," *Somat. Cell Mol. Genet.*, 1994, 20(1):27-38.

Ancellin et al., "Extracellular Export of Sphingosine Kinase-1 Enzyme," *J. Biol. Chem.*, 2002, 277(8):6667-6675.

Anderson et al., "A simple method for the rapid generation of recombinant adenovirus vectors," *Gene Ther.*, 2000, 7:1034-1038.

Anderson, "Human gene therapy," *Nature*, 1998, 392:25-30.

Andreason and Evans, "Introduction and Expression of DNA Molecules in Eukaryotic Cells by Electroporation," *BioTechniques*, 1988, 6(7):650-660.

Augood et al., "Distribution of the mRNAs Encoding TorsinA and TorsinB in the Normal Adult Human Brain," *Ann. Neurol.*, 1999, 46:761-769.

Augood et al., "Dopamine transmission in *DYT1* dystonia: A biochemical and autoradiographical study," *Neurology*, 2002, 59:445-448.

Bass, "The short answer," *Nature*, 2001, 411:428-429.

Bates et al., "Experimental therapeutics in Huntington's disease: are models useful for therapeutic trials?" *Curr Opin Neurol.*, 2003, 16:465-470.

Batzer et al., "Enhanced evolutionary PCR using oligonucleotides with inosine at the 3'-terminus," *Nucl. Acids Res.*, 1991, 19(18):5081.

Baulcombe, "RNA as a target and an initiator of post-transcriptional gene silencing in transgenic plants," *Plant Mol. Biol.*, 1996, 32:79-88.

Behr et al., "Efficient gene transfer into mammalian primary endocrine cells with lipopolyamine-coated DNA," *Proc. Natl. Acad. Sci. USA*, 1989, 86:6982-6986.

Bernstein et al., "Role for a bidentate ribonuclease in the initiation step of RNA interference," *Nature*, 2001, 409:363-366.

Bertrand et al., "The expression cassette determines the functional activity of ribozymes in mammalian cells by controlling their intracellular localization", *RNA*, 1997 3(1):75-88.

Bledsoe et al., "Cytokine production in motor neurons by poliovirus replicon vector gene delivery," *Nat. Biot.*, 2000, 18:964-969.

Boado et al., "Antisense-mediated down-regulation of the human huntingtin gene", *J Pharmacol Exp Ther.* 2000, 295(1):239-243.

Boden et al., "Enhanced gene silencing of HIV-1 specific siRNA using microRNA designed hairpins", *Nucleic Acids Research*, vol. 32, No. 3, pp. 115-1158, 2004.

Branch, "A good antisense molecule is hard to find," *TIBS*, 1998, 23:45-50.

Brantl, "Antisense-RNA regulation and RNA interference," *Biochimica et Biophysica Acta*, 2002, 1575:15-25.

Brash et al., "Strontium Phosphate Transfection of Human Cells in Primary Culture: Stable Expression of the Simian Virus 40 Large-T-Antigen Gene in Primary Human Bronchial Epithelial Cells," *Mol. Cell. Biol.*, 1987, 7(5):2031-2034.

Breakefield et al., "TorsinA: Movement at Many Levels," *Neuron*, 2001, 31:9-12.

Bridge et al., "Induction of an interferon response by RNAi vectors in mammalian cells", *Nat Genet.*, 2003, 34:263-264.

(56) References Cited

OTHER PUBLICATIONS

Brooks et al., "Functional correction of established central nervous system deficits in an animal model of lysosomal storage disease with feline immunodeficiency virus-based vectors," *Proc. Natl. Acad. Sci. USA*, 2002, 99(9):6216-6221.
Brummelkamp et al., "A System for Stable Expression of Short Interfering RNAs in Mammalian Cells," *Science*, 2002, 296:550-553.
Brummelkamp et al., "Stable suppression of tumorigenicity by virus-mediated RNA interference," *Cancer Cell*, 2002, 2:243-247.
Burright et al., "SCA1 Transgenic Mice: A model for neurodegeneration caused by an expanded CAG trinucleotide repeat", *Cell*, 1995, 82:937-948.
Capecchi, "High Efficiency Transformation by Direct Microinjection of DNA into Cultured Mammalian Cells," *Cell*, 1980, 22:479-488.
Caplen et al., "Specific inhibition of gene expression by small couple-stranded RNAs in invertebrate and vertebrate systems," *Proc. Natl. Acad. Sci. USA*, 2001, 98(17):9742-9747.
Caplen et al., "Rescue of polyglutamine-mediated cytotoxicity by double-stranded RNA-mediated RNA interference," *Hum. Mol. Genet.*, 2002, 11(2):175-184.
Carter et al., "Characterization of progressive motor deficits in mice transgenic for the human Huntington's disease mutation", *J Neurosci.*, 1999, 19(8):3248-3257.
Cemal et al., "YAC transgenic mice carrying pathological alleles of the *MJD1* locus exhibit a mild and slowly progressive cerebellar deficit," *Hum. Mol. Genet.*, 2002, 11(9):1075-1094.
Chai et al., "Evidence for proteasome involvement in polyglutamine disease: localization to nuclear inclusions in SCA3/MJD and suppression of polyglutamine aggregation in vitro," *Hum. Mol. Genet.*, 1999, 8(4):673-682.
Chai et al., "Analysis of the Role of Heat Shock Protein (Hsp) Molecular Chaperones in Polyglutamine Disease," *J. Neurosci.*, 1999, 19(23):10338-10347.
Chan et al., "Mechanisms of chaperone suppression of polyglutamine disease: selectivity, synergy and modulation of protein solubility in *Drosophila,*" *Hum. Mol. Genet.*, 2000, 9(19):2811-2820.
Check, "Patent flurry casts cloud over gene silencing," *Nature*, 2002, 417:779.
Check, "Hopes rise for RNA therapy as mouse study hits target", *Nature*, 2004, 432, 136.
Chen et al., "Interaction of Akt-Phosphorylated Ataxin-1 with 14-3-3 mediates neurodegeneration in spinocerebellar ataxia type 1", *Cell*, 2003, 113(4):457-468.
Chiu and Rana, "RNAi in Human Cells: Basic Structural and Functional Features of Small Interfering RNA," *Mol. Cell*, 2002, 10:549-561.
Clemens et al., "Use of double-stranded RNA interference in *Drosophila* cell lines to dissect signal transduction pathways," *Proc. Natl. Acad. Sci. USA*, 2000, 97(12):6499-6503.
Cogoni et al., "Suppression of gene expression by homologous transgenes," *Antonie Van Leeuwenhoek*, 1994, 65:205-209.
Corpet et al., "Multiple sequence alignment with hierarchical clustering," *Nucl. Acids Res.*, 1988, 16(22):10881-10890.
Cortez et al., "ATR and ATRIP: Partners in Checkpoint Signaling," *Science*, 2001, 294:1713-1716.
Couzin, "RNAi shows cracks in its armor", *Science*, 2004, 306, 1124-1125.
Crea et al., "Chemical synthesis of genes for human insulin," *Proc. Natl. Acad. Sci. USA*, 1978, 75(12):5765-5769.
Cullen, "RNA interference: antiviral defense and genetic tool," *Nat. Immunol.*, 2002, 3(7):597-599.
Czauderna et al., "Inducible shRNA expression for application in a prostate cancer mouse model", *Nucleic Acids Research*, vol. 31, No. 21, e127, Oxford University Press, 2003.
Czauderna et al., "Structural variations and stabilizing modifications of synthetic siRNAs in mammalian cells", *Nucleic Acids Res*, 31(11), pp. 2705-2716, 2003.

Dale et al., "A test of the model to predict unusually stable RNA hairpin loop stability", *RNA*, 6, pp. 608-615, 2000.
Davidson and Breakefield, "Viral Vectors for Gene Delivery to the Nervous System," *Nat. Rev. Neurosci.*, 2003, 4(5):353-364.
Davidson et al., "Molecular medicine for the brain: silencing of disease genes with RNA interference", *The Lancet Neurol.*, 2004, 3:145-149.
Davidson et al., "Recombinant adeno-associated virus type 2, 4, and 5 vectors: Transduction of variant cell types and regions in the mammalian central nervous system," *Proc. Natl. Acad. Sci. USA*, 2000, 97(7):3428-3432.
Davidson et al., "Viral delivery of recombinant short hairpin RNAs", *Meth Enzymol*, 392:145-173, (2005).
Deng et al., "First Total Synthesis of an Exceptionally Potent Antitumor Saponin, OSW-1," *J. Org. Chem.*, 1999, 64:202-208.
Dillin, "The specifics of small interfering RNA specificity," *Proc. Natl. Acad. Sci. USA*, 2003, 100(11):6289-6291.
Ding et al., "Selective silencing by RNAi of a dominant allele that causes amyotrophic lateral sclerosis," *Aging Cell*, 2003, 2:209-217.
Doench et al., "siRNAs can function as miRNAs," *Genes Dev.*, 2003, 17(4):438-442.
Doheny et al., "Clinical finding of a myoclonus-dystonia family with two distinct mutations," *Neurology*, 2002, 59:1244-1246.
Donzé and Picard, "RNA interference in mammalian cells using siRNAs synthesized with T7 RNA polymerase," *Nucl. Acids Res.*, 2002, 30(10):1-4.
Elbashir et al., "RNA interference is mediated by 21- and 22-nucleotide RNAs," *Genes Dev.*, 2001, 15:188-200.
Elbashir et al., "Functional anatomy of siRNAs for mediating efficient RNAi in *Drosophila melanogaster* embryo lysate," *EMBO J.*, 2001, 20(23):6877-6888.
Elbashir et al., "Dupleses of 21-nucleotide RNAs mediate RNA interference in cultured mammalian cells", *Nature* vol. 411, 494-498 (2001).
Emamian et al., "Serine 776 of ataxin-1 is critical for polyglutamine-induced disease in SCA1 transgenic mice", *Neuron*, 2003, 38:375-87.
Fahn et al., "Classification of Dystonia," *Dystonia 3: Advances in Neurology*, 1998, 78:1-10.
Felgner et al., "Lipofection: A highly efficient, lipid-mediated DNA-transfection procedure," *Proc. Natl. Acad. Sci. USA*, 1987, 84:7413-7417.
Feng et al., "Inhibition of CCR5-Dependent HIV-1 Infection by Hairpin Ribozyme Gene Therapy against CC-Chemokine Receptor 5", *Virology*, 2000 25;276(2):271-278.
Fernandez-Funez et al., "Identification of genes that modify ataxin-1-induced neurodegeneration", *Nature*, 2000, 408:101-106.
Fire et al., "Potent and specific genetic interference by double-stranded RNA in *Caenorhabditis elegans,*" *Nature*, 1998, 391:806-811.
Fujigasaki et al., "CAG repeat expansion in the TATA box-bidning protein gene causes autosomal dominant cerebellar ataxia", *Brain*, 124, pp. 1939-1947, 2001.
Garrus et al., "Tsg101 and the Vacuolar Protein Sorting Pathway Are Essential for HIV-1 Budding" *Cell*, 2001, 107:55-65.
Gaspar et al., "Ancestral Origins of the Machado-Joseph Disease Mutation: A Worldwide Haplotype Study," *Am. J. Hum. Genet.*, 2001, 68:523-528.
Gitlin et al., "Short interfering RNA confers intracellular antiviral immunity in human cells," *Nature*, 2002, 418:430-434.
Goeddel et al., "Synthesis of human fibroblast interferon by *E. coli,*" *Nucl. Acids Res.*, 1980, 8(18):4057-4074.
Gonzalez-Alegre et al., "Toward Therapy for DYT1 Dystonia: Allele-Specific Silencing of Mutant TorsinA," *Ann. Neurol.*, 2003, 53:781-787.
Gonzalez-Alegre et al., "Silencing primary dystonia: lentiviral-mediated RNA interference therapy for DYT1 Dystonia", *J Neurosci.*, 2005; 25(45):10502-9.
Goodchild et al., "Investigations into the normal function of the DYT1 protein TorsinA," *Mov. Disord.*, 2002, 17(Suppl. 5):958, Abstract only.

(56) References Cited

OTHER PUBLICATIONS

Goto et al., "Suppression of Huntingtin Gene Expression by siRNA: A Possible Therapeutic Tool for Huntington's Disease", *Neurology*, 60(5), Suppl 1, p. A286, Abstract P04.055, 2003.
Grishok et al., "Genetic Requirements for Inheritance of RNAi in *C. elegans*," *Science*, 2000, 287:2494-2497.
Guo and Fuchs, "The First Synthesis of the Aglycone of the Potent Anti-tumor Steroidal Saponin OSW-1," *Tetrahedron Letters*, 1998, 39:1099-1102.
Hamilton and Baulcombe, "A Species of Small Antisense RNA in Posttranscriptional Gene Silencing in Plants," *Science*, 1999, 286:950-952.
Hammond et al., "Post-transcriptional gene silencing by double-stranded RNA", *Nature*. 2001;2(2):110-119.
Hammond et al., "An RNA-directed nuclease mediates post-transcriptional gene silencing in *Drosophila* Cells," *Nature*, 2000, 404:293-296.
Hannon, "RNA interference", *Nature*, 2002, 418:244-251.
Haque et al., "Antisense gene therapy for neurodegenerative disease?" *Exp Neurol.* 1997; 144; 139-46.
Harborth et al., "Identification of essential genes in cultured mammalian cells using small interfering RNAs," *J. Cell Science*, 2001, 114:4557-4565.
Hardy et al., "The Amyloid Hypothesis of Alzheimer's Disease: Progress and Problems on the Road to Therapeutics," *Science*, 2002, 297(5580):353-356.
Harper et al., "Plasmid-based RNA interference, Construction of small-hairpin RNA expression vectors", *Meth Mol Biol*, 309:219-236 (2005).
Harper et al., "RNA interference improves motor and neuropathological abnormalities in a Huntington's disease mouse model", *PNAS*, 102(16):5820-5825, (2005).
Hasholt et al., "Antisense downregulation of mutant huntingtin in a cell model", *J Gene Med.* 2003;5(6):528-38.
Hewett et al., "Mutant torsinA, responsible for early-onset torsion dystonia, forms membrane inclusions in cultured neural cells," *Hum. Mol. Gen.*, 2000, 9(9):1403-1413.
Higgins and Sharp, "Fast and sensitive multiple sequence alignments on a microcomputer," *CABIOS*, 1989, 5(2):151-153.
Higgins and Sharp, "CLUSTAL: a package for performing multiple sequence alignment on a microcomputer," *Gene*, 1988, 73:237-244.
Hilberg et al., "Functional analysis of a retroviral host-range mutant: Altered long terminal repeat sequences allow expression in embryonal carcinoma cells," *Proc. Natl. Acad. Sci. USA*, 1987, 84:5232-5236.
Holen et al., "Positional effects of short interfering RNAs targeting the human coagulation trigger Tissue Factor", *Nucleic Acids Res*, 30(8), pp. 1757-6617, 2002.
Holland et al., "Enhancer sequences of a retroviral vector determine expression of a gene in multipotent hematopoietic progenitors and committed erythroid cells," *Proc. Natl. Acad. Sci. USA*, 1987, 84:8662-8666.
Hornykiewicz et al., "Brain Neurotransmitters in Dystonia Musculorum Deformans," *N. Engl. J. Med.*, 1986, 315:347-353.
Houlden et al., "Corticobasal degeneration and progressive supranuclear palsy share a common tau haplotype," *Neurology*, 2001, 56(12):1702-1706.
Huang et al., "Parallelization of a local similarity algorithm," *CABIOS*, 1992, 8(2):155-165.
Hutton et al., "Association of missense and 5'-splice-site mutations in tau with the inherited dementia FTDP-17," *Nature*, 1998, 393:702-705.
Jacque et al., "Modulation of HIV-1 replication by RNA interference," *Nature*, 2002, 418:435-438.
Johnston, "Biolistic transformation: microbes to mice," *Nature*, 1990, 346:776-777.
Kao et al., "BACE1 suppression by RNA interference in primary cortical neurons", *J. Biol. Chem.*, 2004, 279:1942-1949.

Karlin and Altschul, "Methods for assessing the statistical significance of molecular sequence features by using general scoring schemes," *Proc. Natl. Acad. Sci. USA*, 1990, 87:2264-2268.
Karlin and Altschul, "Applications and statistics for multiple high-scoring segments in molecular sequences," *Proc. Natl. Acad. Sci. USA*, 1993, 90:5873-5877.
Kato et al., "A Complex of the Bacteriophage T7 Primase-Helicase and DNA Polymerase Directs Primer Utilization," *J. Biol. Chem.*, 2001, 276(24):21809-21820.
Kawasaki and Taira, "Short hairpin type of dsRNAs that are controlled by tRNA$^{Val}$ promoter significantly induce RNAi-mediated gene silencing in the cytoplasm of human cells," *Nucl. Acids Res.*, 2003, 31(2):700-707.
Kennerdell and Carthew, "Use of dsRNA-Mediated Genetic Interference to Demonstrate that frizzled and frizzled 2 Act in the Wingless Pathway," *Cell*, 1998, 95:1017-1026.
Kennerdell et al., "Heritable gene silencing in *Drosphila* using double-stranded RNA", *Nat Biotechnol*, 17, 2000;1896-898.
Ketting and Plasterk, "A genetic link between co-suppression and RNA interference in *C. elegans*," *Nature*, 2000, 404:296-298.
Khvorova et al., "Functional siRNAs and miRNAs exhibit strand bias", 2003, *Cell*, 115:505.
Kisielow et al., "Isoform-specific knockdown and expression of adaptor protein ShcA using small interfering RNA," *Biochem. J.*, 2002, 363:1-5.
Kitabwalla and Ruprecht, RNA Interference—A New Weapon Against HIV and Beyond, *N. Engl. J. Med.*, 2002, 347(17):1364-1367.
Klein et al., "ε-Sarcoglycan Mutations Found in Combination with Other Dystonia Gene Mutations," *Ann. Neurol.*, 2002, 52:675-679.
Klein and Ozelius, "Dystonia: clinical features, genetics, and treatment," *Curr. Opin. Neurol.*, 2002, 15:491-497.
Konakova et al., "Cellular Distribution of Torsin A and Torsin B in Normal Human Brain," *Arch. Neurol.*, 2001, 58:921-927.
Koseki et al., "Factors Governing the Activity In Vivo of Ribozymes Transcribed by RNA Polymerase III," *J. Virol.*, 1999, 73(3):1868-1877.
Krichevsky and Kosik, "RNAi functions in cultured mammalian neurons," *Proc. Natl. Acad. Sci. USA*, 2002, 99(18):11926-11929.
Kunath et al., "Transgenic RNA interference in ES cell-derived embryos recapitulates a genetic null phenotype", *Nat. Biotechnol.*, 2003, 21:559-561.
Kunkel et al., "Rapid and Efficient Site-Specific Mutagenesis without Phenotypic Selection," *Meth. Enzymol.*, 1987, 154:367-382.
Kunkel, "Rapid and efficient site-specific mutagenesis without phenotypic selection," *Proc. Natl. Acad. Sci. USA*, 1985, 82:488-492.
Kustedjo et al., "Torsin A and Its Torsion Dystonia-associated Mutant Forms Are Lumenal Glycoproteins That Exhibit Distinct Subcellular Localizations," *J. Biol. Chem.*, 2000, 275(36):27933-27939.
Laccone et al., "A Fast Polymerase Chain Reaction-Mediated Strategy for Introducing Repeat Expansions into CAG-Repeat Containing Genes," *Hum. Mutat.*, 1999, 13(6):497-502.
Lai et al., "Antisense RNA complementary to 3' coding and noncoding sequences of creating kinase is a potent inhibitor of translation in vivo," *Proc. Natl. Acad. Sci. USA*, 1989, 86:10006-10010.
Larrick and Burck, "Gene Transfer: Introduction of DNA into Cells Using Physical and Biological Methods," *Gene Therapy—Application of Molecular Biology*, 1991, Elsevier Science Publishing Co., Inc., New York, Chapter 4, p. 71-104.
Lawn et al., "The sequence of human serum albumin cDNA and its expression in *E. coli*," *Nucl. Acids Res.*, 1981, 9:6103-6114.
Lee et al. "Expression of small interfering RNAs targeted against HIV-1 rev transcripts in human cells," *Nature Biotechnology*, 2002, 19:500-505.
Lee et al., "Neurodegenerative Tauopathies," *Annu. Rev. Neurosci.*, 2001, 24:1121-1159.
Lee et al., "Distinct roles for *Drosophila* Dicer-1 and Dicer-2 in the siRNA/miRNA Silencing Pathways", *Cell*, 2004, 117:69-81.
Léger et al., "Identification of tau protein regions required for process formation in PC12 cells," *J. Cell Sci.*, 1994, 107:3403-3412.

(56) References Cited

OTHER PUBLICATIONS

Leung et al., "Novel mutation in the TOR1A (DYT1) gene in atypical, early onset dystonia and polymorphisms in dystonia and early onset parkinsonism," *Neurogenetics*, 2001, 3:133-143.

Lewis et al., "Enhanced Neurofibrillary Degeneration in Transgenic Mice Expressing Mutant Tau and APP," *Science*, 2001, 293(5534):1487-1491.

Lin et al., "Neurological abnormalities in a knock-in mouse model of Huntington's disease," *Hum. Mol. Genet.*, 2001, 10(2):137-144.

Liu et al., "Specific inhibition of Huntington's disease gene expression by siRNAs in cultured cells", *Proc Japan Acad.*, 79, Ser. B, pp. 293-298, 2003.

Loeffler et al., "Lipopolyamine-Mediated Transfection Allows Gene Expression Studies in Primary Neuronal Cells," *J. Neurochem.*, 1990, 54:1812-1815.

Lotery et al., "Gene transfer to the nonhuman primate retina with recombinant feline immunodeficiency virus vectors", *Hum Gene Ther.*, 2002, 13:689-696.

Manche et al., "Interactions between Double-Stranded RNA Regulators and the Protein Kinase DAI," *Mol. Cell Biol.*, 1992, 12:5238-5248.

Margolis and Ross, "Expansion explosion: new clues to the pathogenesis of repeat expansion neurodegenerative diseases," *Trends Mol. Med.*, 2001, 7:479-482.

Martinez et al., "Single-Stranded Antisense siRNAs Guide Target RNA Cleavage in RNAi," *Cell*, 2002, 110:563-574.

Martinez et al., "Synthetic small inhibiting RNAs: Efficient tools to inactivate oncogenic mutations and restore p53 pathways," *Proc. Natl. Acad. Sci. USA*, 2002, 99(23):14849-14854.

McCaffrey et al., "RNA interference in adult mice," *Nature*, 2002, 418(6893):38-39.

McManus and Sharp, "Gene Silencing in Mammals by Small Interfering RNAs," *Nature Reviews Genetics*, 2002, 3(10):737-747.

McManus et al., "Gene silencing using micro-RNA designed hairpins", *RNA*, 8, pp. 842-850, 2002.

Meinkoth and Wahl, "Hybridization of Nucleic Acids Immobilized on Solid Supports," *Anal. Biochem.*, 1984, 138:267-284.

Mercola and Cohen, "Antisense approaches to cancer gene therapy," *Cancer Gene Therapy*, 1995, 2(1):47-59.

Miller et al., "Allele-specific silencing of dominant disease genes", *PNAS* vol. 100 (12), 7195-7200 (2003).

Miller et al., "Targeting Alzheimer's disease genes with RNA interference: an efficient strategy for silencing mutant alleles", *Nucleic Acids Research*, 32(2), pp. 661-668, 2004.

Miller et al., "Gene Transfer by Retrovirus Vectors Occurs Only in Cells That Are Actively Replicating at the Time of Infection," *Mol. Cell. Biol.*, 1990, 10:4239-4242.

Minks et al., "Structural Requirements of Double-Stranded RNA for the Activation of 2',5'-Oligo(A) Polymerase and Protein Kinase of Interferon-treated HeLa Cells," *J. Biol. Chem.*, 1979, 254(20):10180-10183.

Miyagishi et al., "Strategies for generation of an siRNA expression library directed against the human genome", *Oligonucleotides*, vol. 13, pp. 325-333, 2003.

Miyagishi and Taira, "U6 promoter-driven siRNAs with four uridine 3' overhangs efficiently suppress targeted gene expression in mammalian cells," *Nature Biotechnoloqy*, 2002, 19:497-499.

Mölling, "Naked DNA for vaccine therapy," *J. Mol. Med.*, 1997, 75(4):242-246.

Moulder et al., "Generation of Neuronal Intranuclear Inclusion by Polyglutamine-GFP: Analysis of Inclusion Clearance and Toxicity as a Function of Polyglutamine Length," *J. Neurosci.*, 1999, 19:705-715.

Mullan et al., "A pathogenic mutation for probable Alzheimer's disease in the APP gene at the n-terminus of β-amyloid," *Nature Genetics*, 1992, 1:345-347.

Myers and Miller, "Optimal alignments in linear space," *CABIOS*, 1988, 4:11-17.

Nasir et al., "Targeted Disruption of the Huntington's Disease Gene Results in Embryonic Lethality and Behavioral and Morphological Changes in Heterozygotes," *Cell*, 1995, 81:811-823.

Needleman and Wunsch, "A General Method Applicable to the Search for Similarities in the Amino Acid Sequence of Two Proteins," *J. Mol. Biol.*, 1970, 48:443-453.

Nellemann et al., "Inhibition of Huntingtin Synthesis by Antisense Oligodeoxynucleotides", *Mol Cell Neurosci.* 2000;16(4):313-323.

Nykänen et al., "ATP Requirements and Small Interfering RNA Structure in the RNA Interference Pathway," *Cell*, 2001, 107:309-321.

Oddo et al., "Triple-Transgenic Model of Alzheimer's Disease with Plaques and Tangles: Intracellular Aβ and Synaptic Dysfunction," *Neuron*, 2003, 39:409-421.

Ogura and Wilkinson, "AAA$^+$ superfamily ATPases: common structure-diverse function," *Genes to Cells*, 2001, 6:575-597.

Ohtsuka et al., "An Alternative Approach to Deoxyoligonucleotides as Hybridization Probes by Insertion of Deoxyinosine at Ambiguous Codon Positions," *J. Biol. Chem.*, 1985, 260(5):2605-2608.

Okabe et al., "'Green mice' as a source of ubiquitous green cells," *FEBS Lett.*, 1997, 407:313-319.

Ooboshi et al., "Augmented Adenovirus-Mediated Gene Transfer to Atherosclerotic Vessels," *Arterioscler. Thromb. Vasc. Biol.*, 1997, 17:1786-1792.

Ozelius et al., "The TOR1A (DYT1) Gene Family and Its Role in Early Onset Torsion Dystonia," *Genomics*, 1999, 62:377-384.

Ozelius et al., "The early-onset torsion Dystonia gene (DYT1) encodes an ATP-binding protein," *Nature Genetics*, 1997, 17:40-48.

Paddison et al., "Short hairpin RNAs (shRNAs) induce sequence-specific silencing in mammalian cells," *Genes Dev.*, 2002, 16:948-958.

Paddison et al., "Stable suppression of gene expression by RNAi in mammalian cells," *Proc. Natl. Acad. Sci. USA*, 2002, 99(3):1443-1448.

Pardoll et al., "Exposing the Immunology of Naked DNA Vaccines," *Immunity*, 1995, 3(2):165-169.

Paul et al., "Effective expression of small interfering RNA in human cells," *Nature Biotechnology*, 2002, 29:505-508.

Paule and White, "Transcription by RNA polymerases I and III," *Nucl. Acids Res.*, 2000, 28(6):1283-1298.

Paulson et al., "Machado-Joseph Disease Gene Product Is a Cytoplasmic Protein Widely Expressed in Brain," *Ann. Neurol.*, 1997, 41(4):453-462.

Pearson and Lipman, "Improved tools for biological sequence comparison," *Proc. Natl. Acad. Sci. USA*, 1988, 85:2444-2448.

Pearson, "Using the FASTA Program to Search Protein and DNA Sequence Databases," *Meth. Mol. Biol.*, 1994, 24:307-331.

Pham et al., "A Dicer-2-Dependent 80S Complex Cleaves Targeted mRNAs during RNAi in *Drosophila*", *Cell*, 2004, 117:83-94.

Pittman et al., "A System for Characterizing Cellular and Molecular Events in Programmed Neuronal Cell Death," *J. Neurosci.*, 1993, 13(9):3669-3680.

Poorkaj et al., "Tau Is a Candidate Gene for Chromosome 17 Frontotemporal Dementia," *Ann. Neurol.*, 1998, 43:815-825.

Promega siRNA Designer, SiLentGene U6 Cassette RNA Interference Version 1.1, May 2003, www.promega.com/siRNADesigner/program/default.asp.

Quantin et al., "Adenovirus as an expression vector in muscle cells in vivo," *Proc. Natl. Acad. Sci. USA*, 1992, 89:2581-2584.

Reynolds et al., "Rational siRNA design for RNA interference", *Nat. Biotechnol,.* 2004, 22:326-30.

Rosenfeld et al., "Adenovirus-Meidated Transfer of a Recombinant α1-Antitrypsin Gene to the Lung Epithelium in Vivo," *Science*, 1991, 252:431-434.

Rossolini et al., "Use of deoxyinosine-containing primers vs degenerate primers for polymerase chain reaction based on ambiguous sequence information," *Mol. Cell. Probes*, 1994, 8:91-98.

Rubinson et al., "A lentivirus-based system to functionally silence genes in primary mammalian cells, stem cells and transgenic mice by RNA interference", *Nature Genetics*, 2003, 33:401-406.

Scharfmann et al., "Long term in vivo expression of retrovirus-mediated gene transfer in mouse fibroblast implants," *Proc. Natl. Acad. Sci. USA*, 1991, 88:4626-4630.

(56) References Cited

OTHER PUBLICATIONS

Schilling et al., "Intranuclear inclusions and neuritic aggregates in transgenic mice expressing a mutant N-terminal fragment of huntingtin", *Hum Mol Genet.*, 1999, 8(3):397-407.
Schilling et al., "Distinct behavioral and neuropathological abnormalities in transgenic mouse models of HD and DRPLA", *Neurobiol Dis.*, 2001, 8:405-418.
Schramke et al., "RNA-interference-directed chromatin modification coupled to RNA polymerase II transcription", *Nature*, 2005, 435:1275-1279.
Schwarz et al., "Asymmetry in the Assembly of the RNAi Enzyme Complex," *Cell*, 2003, 115:199-208.
Schwarz et al., "Evidence that siRNAs Function as Guides, Not Primers, in the *Drosophila* and Human RNAi Pathways," *Mol. Cell*, 2002, 10:537-548.
Sharp "RNAi and double-strand RNA," *Genes Dev.*, 1999, 13:139-141.
Shi et al., "Genetic interference in *Trypanosoma brucei* by heritable and inducible double-stranded RNA," *RNA*, 2000, 6:1069-1076.
Shipley et al., "The Role of Glycosylation and Phosphorylation in the Expression of Active Human β-Glucuronidase," *J. Biol. Chem.*, 1993, 268(16):12193-12198.
Sisodia et al., γ-Secretase, Notch, Aβ and Alzheimer's Disease: Where do the Presenilins Fit In? *Nat. Rev. Neurosci.*, 2002, 3(4):281-290.
Sledz et al., "Activation of the interferon system by short-interfering RNAs", *Nat Cell Biol.*, 2003, 5:834-839.
Smith and Waterman, "Comparison of Biosequences," *Adv. Appl. Math.*, 1981, 2:482-489.
Song et al., "RNA interference targeting Fas protects mice from fulminant hepatitis," *Nat. Med.*, 2003, 9:347-351.
Stein et al., "Systemic and Central Nervous System Correction of Lysosomal Storage in Mucopolysaccharidosis Type VII Mice," *J. Virol.*, 1999, 73(4):3424-3429.
Stein et al., "RNAi: Mammalian oocytes do it without RNA-dependent RNA polymerase," *RNA*, 2003, 9:187-192.
Sui et al., "A DNA vector-based RNAi technology to suppress gene expression in mammalian cells," *Proc. Natl. Acad. Sci. USA*, 2002, 99(8):5515-5520.
Svoboda et al., "Selective reduction of dormant maternal mRNAs in mouse oocytes by RNA interference," *Development*, 2000, 127:4147-4156.
Tabara et al., "The rde-1 Gene, RNA Interference, and Transposon Silencing in *C. elegans*," *Cell*, 1999, 99:123-132.
Tanemura et al., "Neurodegeneration with Tau Accumulation in a Transgenic Mouse Expressing V337M Human Tau," *J. Neurosci.*, 2002, 22(1):133-141.
Tang et al., "A biochemical framework for RNA silencing in plants," *Genes Dev.*, 2003, 17(1):49-63.
Temin, "Retrovirus vectors for gene transfer: Efficient integration into and expression of exogenous DNA in vertebrate cell genomes," *Gene Transfer*, 1986, Kucherlapati (ed.), Chapter 6, pp. 149-187.
Tijsterman et al., "Dicers at RISC: The mechanism of RNAi", *Cell*, 2004; 117(1):1-4.
Tijssen, "Overview of principles of hybridization and the strategy of nucleic acid probe assays," *Laboratory Techniques in Biochemistry and Molecular Biology. Hybridization with Nucleic Acid Probes*, Part 1, Chapter 2, Elsevier, New York, 1993, pp. 19-78.
Timmons and Fire, "Specific interference by ingested dsRNA," *Nature*, 1998, 395:854.
Tritz et al., "Screening Promoters for Optimal Expression of Ribozymes", 1999, pp. 115-123, in Intracellular Ribozyme Applications: Principles and Protocols, Horizon Scientific Press.

Trottier et al., "Polyglutamine expansion as a pathological epitope in Huntington's disease and four dominant cerebellar ataxias," *Nature*, 1995, 378:403-406.
Turner et al., "The Potential Exploitation of Plant Viral Translational Enhancers in Biotechnology for Increased Gene Expression," *Mol. Biotech.*, 1995, 3:225-236.
Tuschl, "Expanding small RNA interference," *Nat. Biotechnol.*, 2002, 20:446-448.
Valerio et al., "Retrovirus-mediated gene transfer into embryonal carcinoma and hemopoietic stem cells: expression from a hybrid long terminal repeat," *Gene*, 1989, 84:419-427.
Verma and Somia, "Gene therapy—promises, problems and prospects," *Nature*, 1997, 389:239-242.
Victor et al., "HAT activity is essential for CBP-1-dependent transcription and differentiation in *Caenorhabditis elegans*", *EMBO Reports*, 3(1), pp. 50-55, 2002.
Vieira and Messing, "Production of Single-Stranded Plasmid DNA," *Meth. Enzymol.*, 1987, 153:3-11.
Wagner and Sun, "Double-stranded RNA poses puzzle," *Nature*, 1998, 391:744-745.
Walker et al., "TorsinA immunoreactivity in brains of patients with DYT1 and non-DYT1 dystonia," *Neurology*, 2002, 58:120-124.
Waterhouse et al., "Virus resistance and gene silencing in plants can be induced by simultaneous expression of sense and antisense RNA," *Proc. Natl. Acad. Sci. USA*, 1998, 95:13959-13964.
Wianny and Zernicka-Goetz, "Specific interference with gene function by double-stranded RNA in early mouse development," *Nat. Cell Biol.*, 2000, 2:70-75.
Xia et al., "The HIV Tat protein transduction domain improves the biodistribution of β-glucuronidase expressed from recombinant viral vectors," *Nat. Biotechnol.*, 2001, 19:640-644.
Xia et al., "RNAi suppresses polyglutamine-induced neurodegeneration in a model of spinocerebellar ataxia", *Nat Med*, 10(8):1-5 (2004).
Xia et al., "RNAi suppresses polyglutamine-induced neurodegeneration in a model of spinocerebellar ataxia", *Nat Med*, 10(8), pp. 816-820, 2004.
Xia et al., "siRNA-mediated gene silencing in vitro and in vivo," *Nat. Biotech.*, 2002, 20:1006-1010.
Xiao et al., "Gene therapy vectors based on adeno-associated virus type 1", *Journal of Virology*, 73(5), pp. 3994-4003, 1999.
Yamamoto et al., "Reversal of Neuropatholgy and Motor Dysfunction in a Conditional Model of Huntington's Disease," *Cell*, 2000, 101(1):57-66.
Yang et al., "Specific Double-Stranded RNA Interference in Undifferentiated Mouse Embryonic Stem Cells," *Mol. Cell. Biol.*, 2001, 21(22):7807-7816.
Yu et al., "RNA interference by expression of short-interfering RNAs and hairpin RNAs in mammalian cells," *Proc. Natl. Acad. Sci. USA*, 2002, 99(9):6047-6052.
Yu et al., "Mutant Huntingtin causes contex-dependent neurodegenration in mice with Huntington's Disease", *Journal of Neuroscience*, vol. 23, pp. 2193-2202, 2003.
Zamore et al., "RNAi: Double-Stranded RNA Directs the ATP-Dependent Cleavage of mRNA at 21 to 23 Nucleotide Intervals," *Cell*, 2000, 101:25-33.
Zeng et al., "MicroRNAs and small interfering RNAs can inhibit mRNA expression by similar mechanisms," *Proc. Natl. Acad. Sci. USA*, 2003, 100(17):9779-9784.
Zeng et al., "Sequence requirements for micro RNA processing and function in human cells", *RNA*, 2003, 9(1), 112-123.
Zoghbi and Orr, "Glutamine Repeats and Neurodegeneration," *Annu. Rev. Neurosci.*, 2000, 23:217-247.

*Fig. 1F*
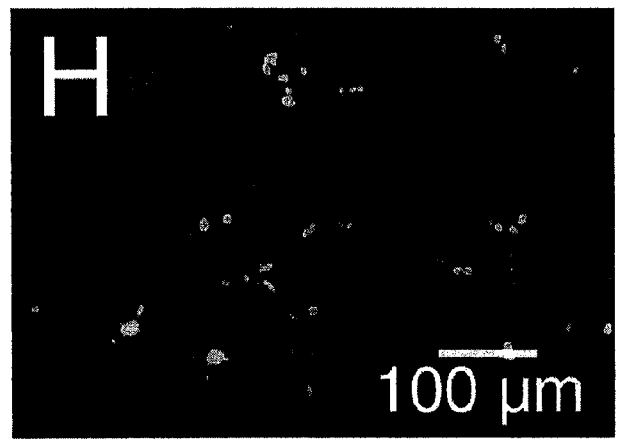
*Fig. 1G*
*Fig. 1H*

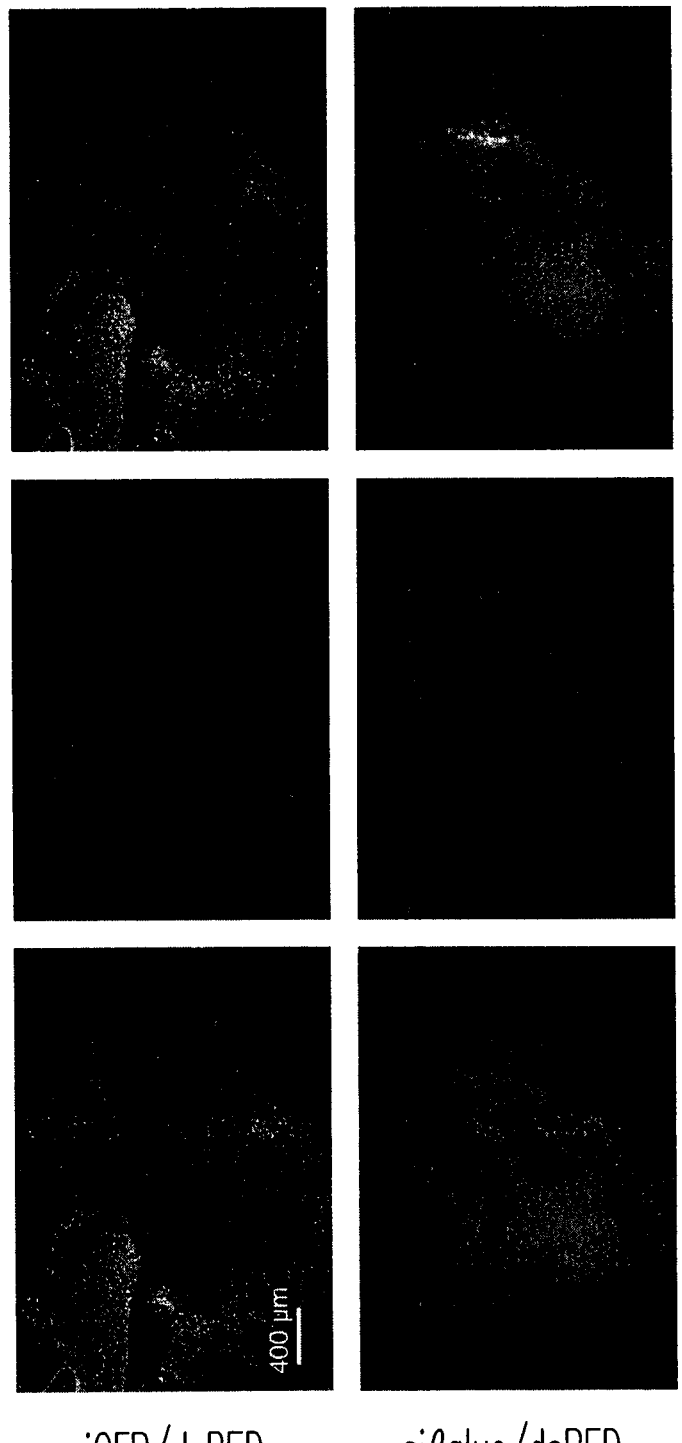

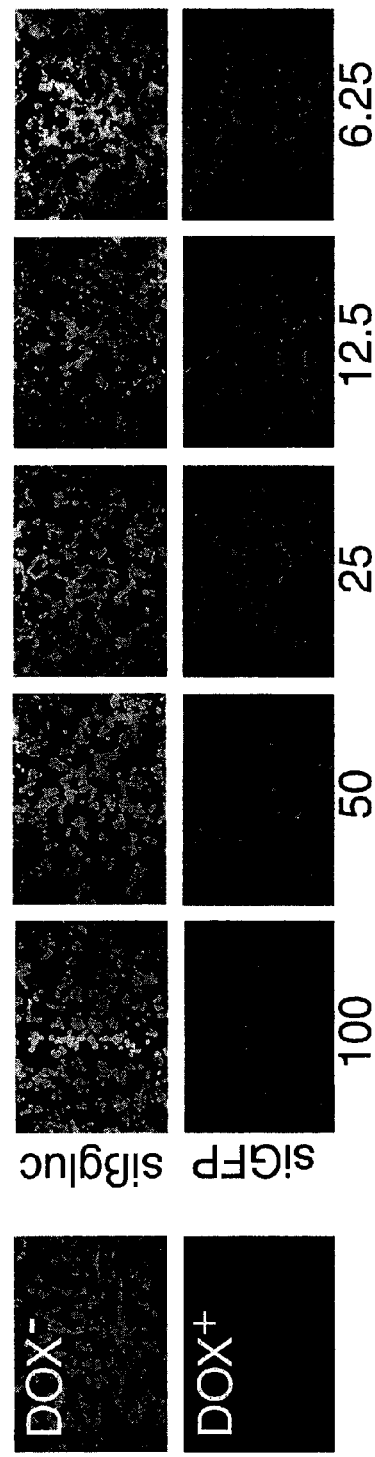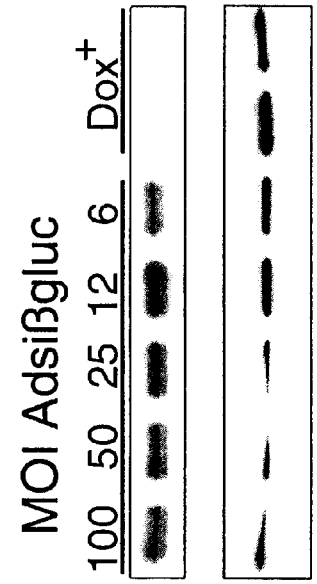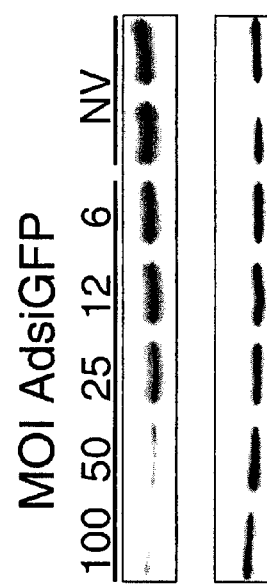
Fig. 3A
Fig. 3C
Fig. 3B

| | Ataxin-3 | | Tau |
|---|---|---|---|
| NAME | Primer Sequence (5'-3') | NAME | Primer Sequence (5'-3') |
| siMiss | CGGCAAGCTGCGCATGAAGTTC<br>ATGAACTTCATGCTCAGCTTGC | siN'-Tau | TCGAAGTGATGGAAGATCACGC<br>CAGCGTGATCTTCCATCACTTC |
| siGFP | ATGAACTTCAGGGTCAGCTTGC<br>CGGCAAGCTGACCCTGAAGTTC | si272 | CAGCCGGGAGTCGGGAAGGTGC<br>CTGCACCTTCCCGACTCCCGGC |
| siC7 | CAGCAGCGGGACCTATCAGGAC<br>CTGTCCTGATAGGTCCCGCTGC | si301 | ACGTCCTCGGCGGCGGCAGTGTGC<br>TTGCACACTGCCGCCTCCGCGGAC |
| siG10 | CAGCAGCAGGGGGACCTATC<br>CTGATAGGTCCCCCTGCTGC | si406 | ACGTCTCCATGGCATCTCAGC<br>TTGCTGAGATGCCATGGAGAC |
| siC7/8 | CAGCAGCCGGACCTATCAGGAC<br>CTGTCCTGATAGGTCCGGCTGC | siA9 | GTGGCCAGATGGAAGTAAAATC<br>CAGATTTTACTTCCATCTGGCC |
| siC10 | CAGCAGCAGCGGGACCTATC<br>CTGATAGGTCCCGCTGCTGC | siA9/C8 | GTGGCCACATGGAAGTAAAATC<br>CAGATTTTACTTCCATGTGGCC |
| siN'CAG | TTGAAAAACAGCAGCAAAAGC<br>CTGCTTTTGCTGCTGTTTTTC | siA9/C12 | GTGGCCAGATGCAAGTAAAATC<br>CAGATTTTACTTGCATCTGGCC |
| siCAG | CAGCAGCAGCAGCAGCAGCAGC<br>CTGCTGCTGCTGCTGCTGCTGC | | |

*Fig. 6*

|       | Ex2<br>siHD | siEx58<br>#1 | siEx58<br>#2 |       | siGFP |
|-------|-------------|--------------|--------------|-------|-------|

*Fig. 15*

| NAME | Primer Sequence (5'-3') | NAME | Primer Sequence (5'-3') |
|---|---|---|---|
| Miscellaneous | | APP | |
| siMiss | ATGAACTTCATGCTCAGCTTGC<br>CGGCAAGCTGCGCATGAAGTTC | siAPP | AAGTGAAGATGGATGCAGAATTC<br>CGGAATTCTGCATCCATCTTCAC |
| siMiss+G | AACTTCACCCTGAGCTTGCC<br>CGGCAAGCTCAGGGTGAAGT | siAPP+G | TGAAGTGAAGATGGATGCAG<br>TCTGCATCCATCTTCACTTC |
| siGFP | ATGAACTTCAGGGTCAGCTTGC<br>CGGCAAGCTGACCCTGAAGTTC | siT8/C9 | AAGTGAATCTGGATGCAGAA<br>ATTCTGCATCCAGATTCACT |
| siGFP+G | AACTTCAGGGTCAGCTTGCC<br>CGGCAAGCTGACCCTGAAGT | siT9/C10 | GAAGTGAATCTGGATGCAGA<br>TTCTGCATCCAGATTCACTT |
| siLamin | AACTGGACTTCCAGAAGAAC<br>TGTTCTTCTGGAAGTCCAGT | siT10/C11 | TGAAGTGAATCTGGATGCAG<br>TCTGCATCCAGATTCACTTC |
| Tau | | siT11/C12 | CTGAAGTGAATCTGGATGCA<br>CTGCATCCAGATTCACTTCA |
| siA9 | GTGGCCAGATGGAAGTAAAA<br>ATTTTACTTCCATCTGGCCA | siT12/C13 | TCTGAAGTGAATCTGGATGC<br>TGCATCCAGATTCACTTCAG |
| siA10 | GGTGGCCAGATGGAAGTAAA<br>TTTTACTTCCATCTGGCCAC | | |
| siA11 | AGGTGGCCAGATGGAAGTAA<br>TTACTTCCATCTGGCCACC | | |
| siA12 | GAGGTGGCCAGATGGAAGTA<br>TTACTTCCATCTGGCCACCT | | |

*Fig. 16*

| | | | | | |
|---|---|---|---|---|---|
| siMiss+G | + | − | − | − | − |
| siA9 | − | + | − | − | − |
| siA10 | − | − | + | − | − |
| siA11 | − | − | − | + | − |
| siA12 | − | − | − | − | + |
Tubulin
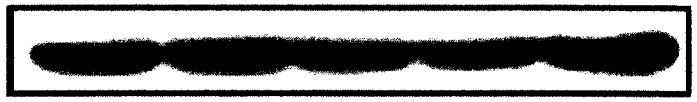
*Fig. 18A*
| | | | |
|---|---|---|---|
| tvMiss | + | − | − |
| tvA10 | − | + | − |
| tvWT-Tau | − | − | + |
Tubulin
*Fig. 18B*

| | | | | |
|---|---|---|---|---|
| tvMiss | + | − | − | − |
| tvAPP | − | + | − | − |
| tvT10/C11 | − | − | + | − |
APP 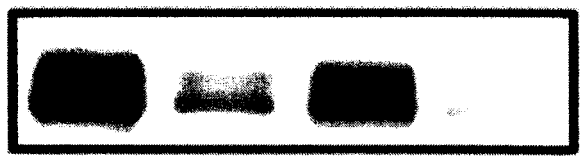
Tubulin 
APPsw 
Tubulin 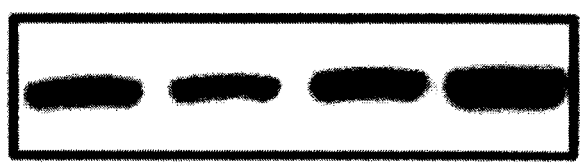
*Fig. 19C*

US 9,487,779 B2

SIRNA-MEDIATED GENE SILENCING

CLAIM OF PRIORITY

This application is a continuation application of U.S. application Ser. No. 13/668,739, which was filed on Nov. 5, 2012, which is a continuation of U.S. application Ser. No. 12/952,449, which was filed on Nov. 23, 2010, which issued as U.S. Pat. No. 8,329,890, which is a continuation of U.S. application Ser. No. 10/738,642, which was filed on Dec. 16, 2003, which is a continuation-in-part of International Application No. PCT/US03/16887 filed on May 26, 2003, which is a continuation-in-part of U.S. application Ser. No. 10/430,351 filed on May 5, 2003, which is a continuation of U.S. application Ser. No. 10/322,086 filed on Dec. 17, 2002, which is a continuation-in-part application of U.S. application Ser. No. 10/212,322, filed Aug. 5, 2002, all of which applications are incorporated herein by reference.

STATEMENT REGARDING FEDERALLY SPONSORED RESEARCH OR DEVELOPMENT

This invention was made with government support under NS044494 and NS38712 awarded by the National Institutes of Health. The government has certain rights in the invention.

BACKGROUND OF THE INVENTION

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis. Recent work suggests that RNA fragments are the sequence-specific mediators of RNAi (Elbashir et al., 2001). Interference of gene expression by these small interfering RNA (siRNA) is now recognized as a naturally occurring strategy for silencing genes in C. elegans, Drosophila, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000). In mammalian cell culture, a siRNA-mediated reduction in gene expression has been accomplished only by transfecting cells with synthetic RNA oligonucleotides (Caplan et al., 2001; Elbashir et al., 2001).

SUMMARY OF THE INVENTION

The present invention provides a mammalian cell containing an isolated first strand of RNA of 15 to 30 nucleotides in length having a 5' end and a 3' end, wherein the first strand is complementary to at least 15 nucleotides of a targeted gene of interest, and wherein the 5' end of the first strand of RNA is operably linked to a G nucleotide to form a first segment of RNA, and an isolated second strand of RNA of 15 to 30 nucleotides in length having a 5' end and a 3' end, wherein at least 12 nucleotides of the first and second strands are complementary to each other and form a small interfering RNA (siRNA) duplex under physiological conditions, and wherein the siRNA silences only one allele of the targeted gene in the cell. The duplex formed by the two strands of RNA may be between 15 and 25 base pairs in length, such as 20 base pairs in length. The first strand may be 20 nucleotides in length, and the second strand may be 20 nucleotides in length. In one embodiment, the 5' end of the second strand of RNA is operably linked to a G nucleotide. This G nucleotide may be directly linked to the second strand of RNA (i.e., no intervening nucleotides are present).

In one embodiment, the first strand is complementary to 19 out of 20 contiguous nucleotides of the targeted gene and is non-complementary to one nucleotide of the targeted gene. For example, the one non-complementary nucleotide is at position 9, 10, or 11, as measured from the 5' end of the first strand of RNA. In one embodiment, the one non-complementary nucleotide is at position 10, as measured from the 5' end of the first strand of RNA. In an alternative embodiment, the first strand is complementary to 18 out of 20 contiguous nucleotides of the targeted gene and is non-complementary to two nucleotides of the targeted gene. For example, the two non-complementary nucleotides are at nucleotide position 9, 10, 11, or 12 as measured from the 5' end of the first strand of RNA. In one embodiment, the two non-complementary nucleotides are at nucleotide position 10 and 11, as measured from the 5' end of the first strand of RNA.

In the present invention, the first and second strand of RNA may be operably linked together by means of an RNA loop strand to form a hairpin structure to form a "duplex structure" and a "loop structure." These loop structures may be from 4 to 10 nucleotides in length. For example, the loop structure may be 4, 5 or 6 nucleotides long.

In the mammalian cell of the present invention, the targeted gene may be a gene associated with a condition amenable to siRNA therapy. In one embodiment, the gene encodes a transcript for Swedish double amyloid precursor protein (APPsw) mutation or a transcript for Tau.

The present invention also provides a mammalian cell containing an expression cassette encoding an isolated first strand of RNA of 15 to 30 nucleotides in length having a 5' end and a 3' end, wherein the first strand is complementary to at least 15 nucleotides of a targeted gene of interest, and wherein the 5' end of the first strand of RNA is operably linked to a G nucleotide to form a first strand of RNA, and an isolated second strand of RNA of 15 to 30 nucleotides in length having a 5' end and a 3' end, and wherein at least 12 nucleotides of the first and second strands are complementary to each other and form a small interfering RNA (siRNA) duplex under physiological conditions, and wherein the siRNA silences only one allele of the targeted gene in the cell. These expression cassettes may further contain a promoter. Such promoters can be regulatable promoters or constitutive promoters. Examples of suitable promoters include a CMV, RSV, pol II or pol III promoter. The expression cassette may further contain a polyadenylation signal, such as a synthetic minimal polyadenylation signal. The expression cassette may further contain a marker gene. The expression cassette may be contained in a vector. Examples of appropriate vectors include adenoviral, lentiviral, adeno-associated viral (AAV), poliovirus, HSV, or murine Maloney-based viral vectors. In one embodiment, the vector is an adenoviral vector.

The present invention further provides an isolated RNA duplex containing a first strand of RNA having a 5' end and a 3' end, and a second strand of RNA, transcript encoded by siA10 GGTGGCCAGATGGAAGTAAA (SEQ ID NO:63), wherein the 5' end of the first strand of RNA is operably linked to a G nucleotide to form a first segment of RNA, and wherein the second strand is complementary to all the nucleotides of the first strand. In one embodiment, the first strand and the second strand are operably linked by means of an RNA loop strand to form a hairpin structure comprising a duplex structure and a loop structure.

The present invention also provides an expression cassette comprising a nucleic acid encoding at least one strand of the RNA duplex described above. As used herein the term "encoded by" means that the DNA sequence in the SEQ ID NO is transcribed into the RNA of interest.

The present invention provides a vector containing the expression cassette described above. Further, the vector may contain two expression cassettes, a first expression cassette containing a nucleic acid encoding a first strand of the RNA duplex and a second expression cassette containing a nucleic acid encoding a second strand of the RNA duplex. The present invention also provides cells containing these expression cassettes (such as a mammalian cell), and a non-human mammal that has a cell containing one of these expression cassettes.

The present invention provides an isolated RNA duplex containing a first strand of RNA having a 5' end and a 3' end, and a second strand of RNA, wherein the first strand is made of 20 nucleotides complementary to Swedish double amyloid precursor protein (APPsw) mutation transcript encoded by siT10/C11 TGAAGTGAATCTGGATGCAG (SEQ ID NO:64), wherein the 5' end of the first strand of RNA is operably linked to a G nucleotide to form a first segment of RNA, and wherein the second strand is complementary to all the nucleotides of the first strand. In this RNA duplex, the first strand and the second strand may be operably linked by means of an RNA loop strand to form a hairpin structure comprising a duplex structure and a loop structure. The loop structure may contain from 4 to 10 nucleotides, such as 4, 5 or 6 nucleotides.

The present invention provides an expression cassette containing a nucleic acid encoding at least one strand of the RNA duplex described above. It also provides a vector that contains this expression cassette. Further, the vector may contain two expression cassettes, a first expression cassette containing a nucleic acid encoding the first strand of the RNA duplex as described above and a second expression cassette containing a nucleic acid encoding the second strand of the RNA duplex. The present invention also provides a cell (such as a mammalian cell) containing this expression cassette.

In the present invention, an expression cassette may contain a nucleic acid encoding at least one strand of the RNA duplex described above. Such an expression cassette may further contain a promoter. The expression cassette may be contained in a vector. These cassettes and vectors may be contained in a cell, such as a mammalian cell. A cell in a non-human mammal may contain the cassette or vector. The vector may contain two expression cassettes, the first expression cassette containing a nucleic acid encoding the first strand of the RNA duplex, and a second expression cassette containing a nucleic acid encoding the second strand of the RNA duplex.

The present invention further provides a method of performing allele-specific gene silencing in a mammal by administering to the mammal an isolated first strand of RNA of 15 to 30 nucleotides in length having a 5' end and a 3' end, wherein the first strand is complementary to at least 15 nucleotides of a targeted gene of interest, and wherein the 5' end of the first strand of RNA is operably linked to a G nucleotide to form a first segment of RNA, and an isolated second strand of RNA of 15 to 30 nucleotides in length having a 5' end and a 3' end, wherein at least 12 nucleotides of the first and second strands are complementary to each other and form a small interfering RNA (siRNA) duplex under physiological conditions, and wherein the siRNA preferentially silences one allele of the targeted gene in the mammal. In one embodiment of the present invention, the duplex is between 15 and 25 base pairs in length.

In one embodiment, the duplex may be 20 base pairs in length. In one embodiment of the present invention, the first strand is 20 nucleotides in length, and the second strand is 20 nucleotides in length. For example, the first strand is complementary to 19 out of 20 contiguous nucleotides of the targeted gene and is non-complementary to one nucleotide of the targeted gene. The one non-complementary nucleotide may be at position 9, 10, or 11, as measured from the 5' end of the first strand of RNA. For instance, the one non-complementary nucleotide is at position 10, as measured from the 5' end of the first strand of RNA.

In another embodiment, the first strand is complementary to 18 out of 20 contiguous nucleotides of the targeted gene and is non-complementary to two nucleotides of the targeted gene. The two non-complementary nucleotides may be at nucleotide position 9, 10, 11, or 12 as measured from the 5' end of the first strand of RNA. For instance, the two non-complementary nucleotides may be at nucleotide position 10 and 11, as measured from the 5' end of the first strand of RNA. In this method, the 5' end of the second strand of RNA may be operably linked to a G nucleotide. In one embodiment, the first strand and the second strand are operably linked by means of an RNA loop strand to form a hairpin structure comprising a duplex structure and a loop structure. In one embodiment, the targeted gene is a gene associated with a condition amenable to siRNA therapy. For example, gene may encode a transcript for Swedish double amyloid precursor protein (APPsw) mutation or a transcript for Tau.

The targeted gene may be a gene associated with a condition amenable to siRNA therapy. For example, the condition amenable to siRNA therapy could be a disabling neurological disorder. "Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of DNA repeats such as the polyglutamine (polyQ) repeat diseases, e.g., Huntington's disease (HD), specific spinocerebellar ataxias (SCA1, SCA2, SCA3, SCA6, SCAT, and SCA17), spinal and bulbar muscular atrophy (SBMA), dentatorubropallidoluysian atrophy (DRPLA).

The present invention also provides a method of producing an RNA by (a) producing an isolated first strand of RNA of 15 to 30 nucleotides in length having a 5' end and a 3' end, wherein the first strand is complementary to at least 15 nucleotides of a targeted gene of interest, and wherein the 5' end of the first strand of RNA is operably linked to a G nucleotide to form a first segment of RNA, (b) producing an isolated second strand of RNA of 15 to 30 nucleotides in length having a 5' end and a 3' end, and (c) contacting the first strand and the second strand under hybridizing conditions to form a siRNA duplex, wherein the siRNA silences only one allele of the targeted gene in the cell.

In the present method, the duplex may be between 15 and 25 base pairs in length, such as 20 base pairs in length. In one embodiment, the first strand is 20 nucleotides in length, and the second strand is 20 nucleotides in length. The first strand may be complementary to 19 out of 20 contiguous nucleotides of the targeted gene and is non-complementary to one nucleotide of the targeted gene. In one embodiment, the one non-complementary nucleotide is at position 9, 10, or 11, as measured from the 5' end of the first strand of RNA (such as at position 10). Alternatively, the first strand may be complementary to 18 out of 20 contiguous nucleotides of the targeted gene and is non-complementary to one nucleotide of the targeted gene. In one embodiment, the two non-complementary nucleotides are at nucleotide position 9, 10, 11, or 12 as measured from the 5' end of the first strand of RNA (such as at nucleotide position 10 and 11). In one embodiment, the 5' end of the second strand of RNA is operably linked (directly or indirectly) to a G nucleotide.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIGS. 1A-1J. siRNA expressed from CMV promoter constructs and in vitro effects. (A) A cartoon of the expression plasmid used for expression of functional siRNA in cells. The CMV promoter was modified to allow close juxtaposition of the hairpin to the transcription initiation site, and a minimal polyadenylation signal containing cassette was constructed immediately 3' of the MCS (mCMV, modified CMV; mpA, minipA). (B, C) Fluorescence photomicrographs of HEK293 cells 72 h after transfection of pEGFPN1 and pCMVβgal (control), or pEGFPN1 and pmCMVsiGFPmpA, respectively. (D) Northern blot evaluation of transcripts harvested from pmCMVsiGFPmpA (lanes 3, 4) and pmCMVsiβgalmpA (lane 2) transfected HEK293 cells. Blots were probed with $^{32}$P-labeled sense oligonucleotides. Antisense probes yielded similar results (not shown). Lane 1, $^{32}$P-labeled RNA markers. AdsiGFP infected cells also possessed appropriately sized transcripts (not shown). (E) Northern blot for evaluation of target mRNA reduction by siRNA (upper panel). The internal control GAPDH is shown in the lower panel. HEK293 cells were transfected with pEGFPN1 and pmCMVsiGFPmpA, expressing siGFP, or plasmids expressing the control siRNA as indicated. pCMVeGFPx, which expresses siGFPx, contains a large poly(A) cassette from SV40 large T and an unmodified CMV promoter, in contrast to pmCMVsiGFPmpA shown in (A). (F) Western blot with anti-GFP antibodies of cell lysates harvested 72 h after transfection with pEGFPN1 and pmCMVsiGFPmpA, or pEGFPN1 and pmCMVsiβglucmpA. (G, H) Fluorescence photomicrographs of HEK293 cells 72 h after transfection of pEGFPN1 and pCMVsiGFPx, or pEGFPN1 and pmCMVsiβglucmpA, respectively. (I, J) siRNA reduces expression from endogenous alleles. Recombinant adenoviruses were generated from pmCMVsiβglucmpA and pmCMVsiGFPmpA and purified. HeLa cells were infected with 25 infectious viruses/cell (MOI=25) or mock-infected (control) and cell lysates harvested 72 h later. (I) Northern blot for β-glucuronidase mRNA levels in Adsiβgluc and AdsiGFP transduced cells. GAPDH was used as an internal control for loading. (J) The concentration of β-glucuronidase activity in lysates quantified by a fluorometric assay. Stein, C. S. et al., *J. Virol.* 73:3424-3429 (1999).

FIGS. 2A-2C. Viral vectors expressing siRNA reduce expression from transgenic and endogenous alleles in vivo. Recombinant adenovirus vectors were prepared from the siGFP and siβgluc shuttle plasmids described in FIG. 1. (A) Fluorescence microscopy reveals diminution of eGFP expression in vivo. In addition to the siRNA sequences in the E1 region of adenovirus, RFP expression cassettes in E3 facilitate localization of gene transfer. Representative photomicrographs of eGFP (left), RFP (middle), and merged images (right) of coronal sections from mice injected with adenoviruses expressing siGFP (top panels) or siβgluc (bottom panels) demonstrate siRNA specificity in eGFP transgenic mice striata after direct brain injection. (B) Full coronal brain sections (1 mm) harvested from AdsiGFP or Adsiβgluc injected mice were split into hemisections and both ipsilateral (il) and contralateral (cl) portions evaluated by western blot using antibodies to GFP. Actin was used as an internal control for each sample. (C) Tail vein injection of recombinant adenoviruses expressing siβgluc directed against mouse β-glucuronidase (AdsiMuβgluc) reduces endogenous β-glucuronidase RNA as determined by Northern blot in contrast to control-treated (Adsiβgal) mice.

FIGS. 3A-3D. siGFP gene transfer reduces Q19-eGFP expression in cell lines. PC12 cells expressing the polyglutamine repeat Q19 fused to eGFP (eGFP-Q19) under tetracycline repression (A, bottom left) were washed and dox-free media added to allow eGFP-Q19 expression (A, top left). Adenoviruses were applied at the indicated multiplicity of infection (MOI) 3 days after dox removal. (A) eGFP fluorescence 3 days after adenovirus-mediated gene transfer of Adsiβgluc (top panels) or AdsiGFP (bottom panels). (B, C) Western blot analysis of cell lysates harvested 3 days after infection at the indicated MOIs demonstrate a dose-dependent decrease in GFP-Q19 protein levels. NV, no virus. Top lanes, eGFP-Q19. Bottom lanes, actin loading controls. (D) Quantitation of eGFP fluorescence. Data represent mean total area fluorescence±standard deviation in 4 low power fields/well (3 wells/plate).

FIG. 6. Primer sequences (SEQ ID NOs:11-40) for in vitro synthesis of siRNAs using T7 polymerase. All primers contain the following T7 promoter sequence at their 3' ends: 5'-TATAGTGAGTCGTATTA-3' (SEQ ID NO:9). The following primer was annealed to all oligos to synthesize siRNAs: 5'-TAATACGACTCACTATAG-3' (SEQ ID NO:10).

FIG. 15. Allele-specific silencing of mutant huntingtin by siRNA. PC6-3 cells were co-transfected with plasmids expressing siRNA specific for the polymorphism encoding the transcript for mutant huntingtin.

FIG. 16. Primer sequences for in vitro generation of siRNA duplexes using T7 polymerase (SEQ ID NOs:11-12, 13-14, 63-90). All primers used for T7 synthesis contain the following promoter sequence at their 3' ends: 5'-CTATAGT-GAGTCGTATTA-3' (SEQ ID NO:62). The following primer was annealed to all templates to synthesize siRNA duplexes: 5'-TAATACGACTCACTATAG-3' (SEQ ID NO:10).

FIGS. 18A-18B. Optimization of allele-specific silencing of mutant tau. Cos-7 cells were cotransfected with expression constructs encoding mutant (V337M-GFP) and WT (Flag-WT) tau and the indicated siRNAs or shRNA plasmids. (A) Western blot results showing the efficacy of allele-specific silencing when varying the placement of the point mutation (G to A) in the siRNA from positions 9-12. (B) Silencing tau with shRNA plasmid expressed from the tRNA-valine promoter. Shown is a western blot analysis of cells cotransfected with mutant and wild type tau and the indicated shRNA plasmids. Placing the mutation at position 10 (tvA10) of the hairpin results in strong preferential silencing of mutant tau. shRNA directed against wild type (mismatched at position 9 relative to mutant tau) tau inhibits expression from both alleles but shows a preference for the wild type sequence.

FIGS. 19A-19C. Optimization of allele-specific silencing of mutant APP. Cos-7 cells were transfected with expression constructs encoding wild type APP (APP) or mutant (APPsw) and the indicated siRNAs or shRNA plasmids. (A) Immunofluorescence of Cos-7 cells cotransfected with plasmids encoding APP or APPsw and the indicated siRNA+G. Representative images of fields (630×) reveals that allele specificity is optimal when the double mismatch is placed at the central position (siT10/C11) of the targeted sequence. APP proteins are visualized with APP antibody followed by secondary antibody labeled with FITC (green). Nuclei are stained with DAPI (blue). (B) Lanes 5-10 show a Western blot of cells transfected as in A, confirming preferential silencing of APPsw with siRNA containing central mismatches. Lane 4 is APP or APPsw transfected without siRNA. Lane 11 represents untransfected cells showing endogenous APP. Also shown in lanes 1-3 is comparable silencing of APP with siRNA or siRNA+G duplexes targeted to APP. Tubulin is shown as a loading control. (C) Western blot analysis of Cos-7 cells transfected with APP or APPsw and the indicated shRNA plasmids. tvAPP silences APP whereas tvT10/C11 selectively suppresses APPsw expression. Endogenous APP in untransfected cells is shown in the last lane. Tubulin loading control is also shown.

DETAILED DESCRIPTION OF THE INVENTION

Figure 1A:
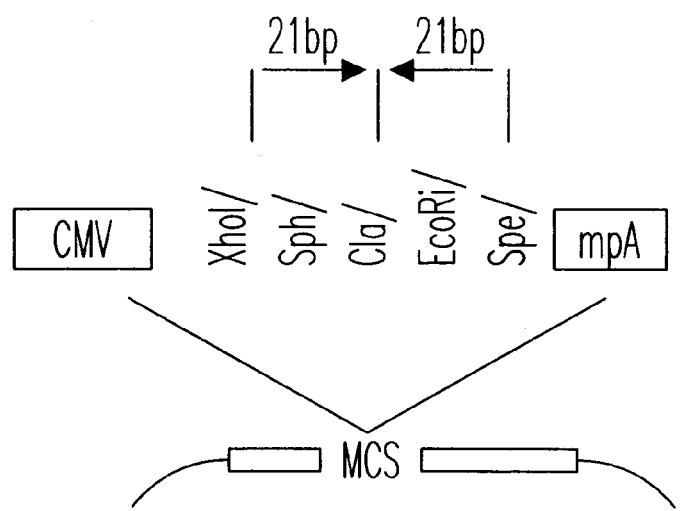
Figure 1B:
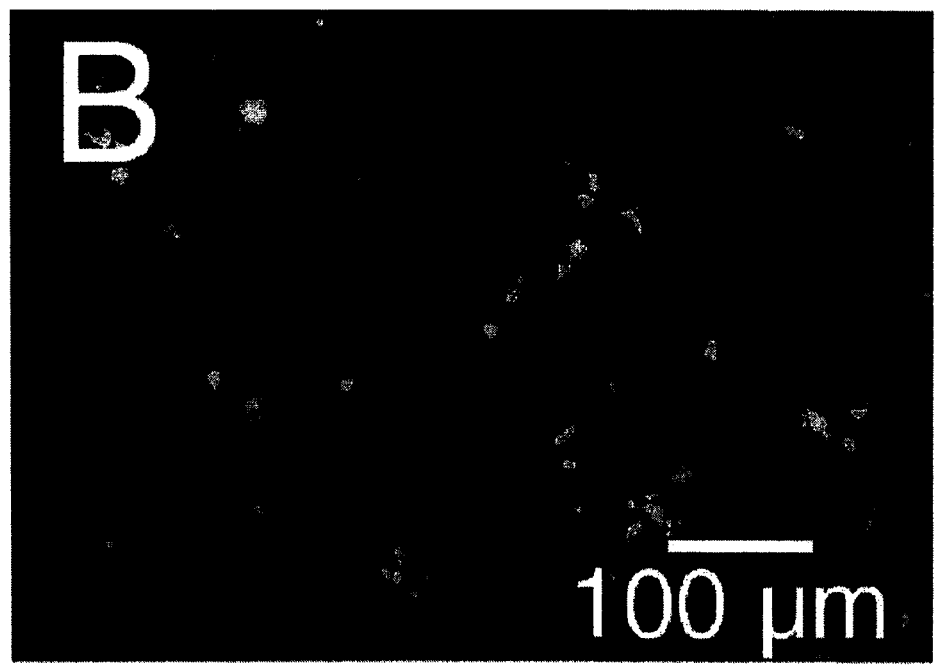

Modulation of gene expression by endogenous, noncoding RNAs is increasingly appreciated as a mechanism playing a role in eukaryotic development, maintenance of chromatin structure and genomic integrity (McManus, 2002). Recently, techniques have been developed to trigger RNA interference (RNAi) against specific targets in mammalian cells by introducing exogenously produced or intracellularly expressed siRNAs (Elbashir, 2001; Brummelkamp, 2002). These methods have proven to be quick, inexpensive and effective for knockdown experiments in vitro and in vivo (2 Elbashir, 2001; Brummelkamp, 2002; McCaffrey, 2002; Xia, 2002). The ability to accomplish selective gene silencing has led to the hypothesis that siRNAs might be employed to suppress gene expression for therapeutic benefit (Xia, 2002; Jacque, 2002; Gitlin, 2002).

RNA interference is now established as an important biological strategy for gene silencing, but its application to mammalian cells has been limited by nonspecific inhibitory effects of long double-stranded RNA on translation. Moreover, delivery of interfering RNA has largely been limited to administration of RNA molecules. Hence, such administration must be performed repeatedly to have any sustained effect. The present inventors have developed a delivery mechanism that results in specific silencing of targeted genes through expression of small interfering RNA (siRNA). The inventors have markedly diminished expression of exogenous and endogenous genes in vitro and in vivo in brain and liver, and further apply this novel strategy to a model system of a major class of neurodegenerative disorders, the polyglutamine diseases, to show reduced polyglutamine aggregation in cells. This strategy is generally useful in reducing expression of target genes in order to model biological processes or to provide therapy for dominant human diseases.

Disclosed herein is a strategy that results in substantial silencing of targeted alleles via siRNA. Use of this strategy results in markedly diminished in vitro and in vivo expression of targeted alleles. This strategy is useful in reducing expression of targeted alleles in order to model biological processes or to provide therapy for human diseases. For example, this strategy can be applied to a major class of neurodegenerative disorders, the polyglutamine diseases, as is demonstrated by the reduction of polyglutamine aggregation in cells following application of the strategy. As used herein the term "substantial silencing" means that the mRNA of the targeted allele is inhibited and/or degraded by the presence of the introduced siRNA, such that expression of the targeted allele is reduced by about 10% to 100% as compared to the level of expression seen when the siRNA is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of an allele when an siRNA has not been introduced to a cell.

Dominantly inherited diseases are ideal candidates for siRNA-based therapy. To explore the utility of siRNA in inherited human disorders, the present inventors employed cellular models to test whether mutant alleles responsible for these dominantly-inherited human disorders could be specifically targeted. First, different classes of dominantly inherited, untreatable neurodegenerative diseases were examined: polyglutamine (polyQ) neurodegeneration in MJD/SCA3, Huntington's disease and frontotemporal dementia with parkinsonism linked to chromosome 17 (FTDP-17). Machado-Joseph disease is also known as Spinocerebellar Ataxia Type 3 (The HUGO official name is MJD). The gene involved is MJD1, which encodes for the protein ataxin-3 (also called Mjd1p). Huntington's disease is due to expansion of the CAG repeat motif in exon 1 of huntingtin. In 38% of patients a polymorphism exists in exon 58 of the huntingtin gene, allowing for allele specific targeting. Frontotemporal dementia (sometimes with parkinonism, and linked to chromosome 17, so sometimes called FTDP-17) is due to mutations in the MAPT1 gene that encodes the protein tau. The inventors also examined amyloid precursor protein (APP) as a target of RNAi.

APP and tau were chosen as candidate RNAi targets because of their central role in inherited and acquired forms of age-related dementia, including Alzheimer's disease (AD) (Hardy et al., 2002; Lee et al., 2001; Mullan et al., 1992; Poorkaj et al., 1998; Hutton et al., 1998). AD is characterized by two major pathological hallmarks: senile plaques, which contain beta-amyloid (Aβ) derived from cleavage of APP; and neurofibrillary tangles, which contain filamentous tau protein. Rare inherited forms of AD have revealed an essential role for Aβ production in the pathogenesis of all forms of AD, both sporadic and inherited (Hardy et al., 2002). Mutations in the three genes known to cause familial AD—the genes encoding APP, presenilin 1 and presenilin 2—act dominantly to enhance the production of neurotoxic Aβ (Hardy et al., 2002).

The best studied AD mutation is the Swedish double mutation in APP (APPsw), two consecutive missense changes that alter adjacent amino acids near the β cleavage site (Mullan et al., 1992). APPsw has been used to create several widely used transgenic mouse models of AD (Lewis et al., 2001; Oddo et al., 2003), thus the inventors chose it as an ideal mutation against which to generate allele-specific siRNAs for AD research. Such siRNA might also have therapeutic value because RNAi-mediated silencing of APP should inhibit Aβ deposition.

Tau, the major component of neurofibrillary tangles, likewise plays a significant role in AD pathogenesis (Lee et al., 2001). Mutations in tau cause a similar dominantly inherited neurodegenerative disease, frontotemporal dementia with parkinsonism linked to chromosome 17 (FTDP-17). In FTDP-17, tau mutations either alter the tau protein sequence or lead to aberrant splicing (Lee et al., 2001; Lewis et al., 2001; Oddo et al., 2003). Abnormalities of tau expression also contribute to several other important neurodegenerative disorders, including progressive supranuclear palsy and cortical-basal ganglionic degeneration (Houlden et al., 2001). Thus, efforts to reduce tau expression, either generally or in an allele-specific manner, may prove to be therapeutically useful in FTDP-17, AD or other tau-related diseases.

The polyQ neurodegenerative disorders include at least nine diseases caused by CAG repeat expansions that encode polyQ in the disease protein. PolyQ expansion confers a dominant toxic property on the mutant protein that is associated with aberrant accumulation of the disease protein in neurons (Zoghbi, 2000). In FTDP-17, Tau mutations lead to the formation of neurofibrillary tangles accompanied by neuronal dysfunction and degeneration (Poorkaj, 1998; Hutton, 1998). The precise mechanisms by which these mutant proteins cause neuronal injury are unknown, but considerable evidence suggests that the abnormal proteins themselves initiate the pathogenic process (Zoghbi, 2000). Accordingly, eliminating expression of the mutant protein by siRNA or other means slows or prevents disease (Yamamoto, 2000). However, because many dominant disease genes also encode essential proteins (e.g. Nasir, 1995) siRNA-mediated approaches were developed that selectively inactivate mutant alleles, while allowing continued expression of the wild type proteins ataxin-3 and huntingtin.

Second, the dominantly-inherited disorder DYT1 dystonia was studied. DYT1 dystonia is also known as Torsion dystonia type 1, and is caused by a GAG deletion in the TOR1A gene encoding torsinA. DYT1 dystonia is the most common cause of primary generalized dystonia. DYT1 usually presents in childhood as focal dystonia that progresses to severe generalized disease (Fahn, 1998; Klein, 2002a). With one possible exception (Leung, 2001; Doheny, 2002; Klein, 2002), all cases of DYT1 result from a common GAG deletion in TOR1A, eliminating one of two adjacent glutamic acids near the C-terminus of the protein TorsinA (TA) (Ozelius, 1997). Although the precise cellular function of TA is unknown, it seems clear that mutant TA (TAmut) acts through a dominant-negative or dominant-toxic mechanism (Breakefield, 2001).

Several characteristics of DYT1 make it an ideal disease in which to use siRNA-mediated gene silencing as therapy. Of greatest importance, the dominant nature of the disease suggests that a reduction in mutant TA, whatever the precise pathogenic mechanism proves to be, is helpful. Moreover, the existence of a single common mutation that deletes a full three nucleotides suggested it might be feasible to design siRNA that specifically targets the mutant allele and is applicable to all affected persons. Finally, there is no effective therapy for DYT1, a relentless and disabling disease.

Figure 11A:
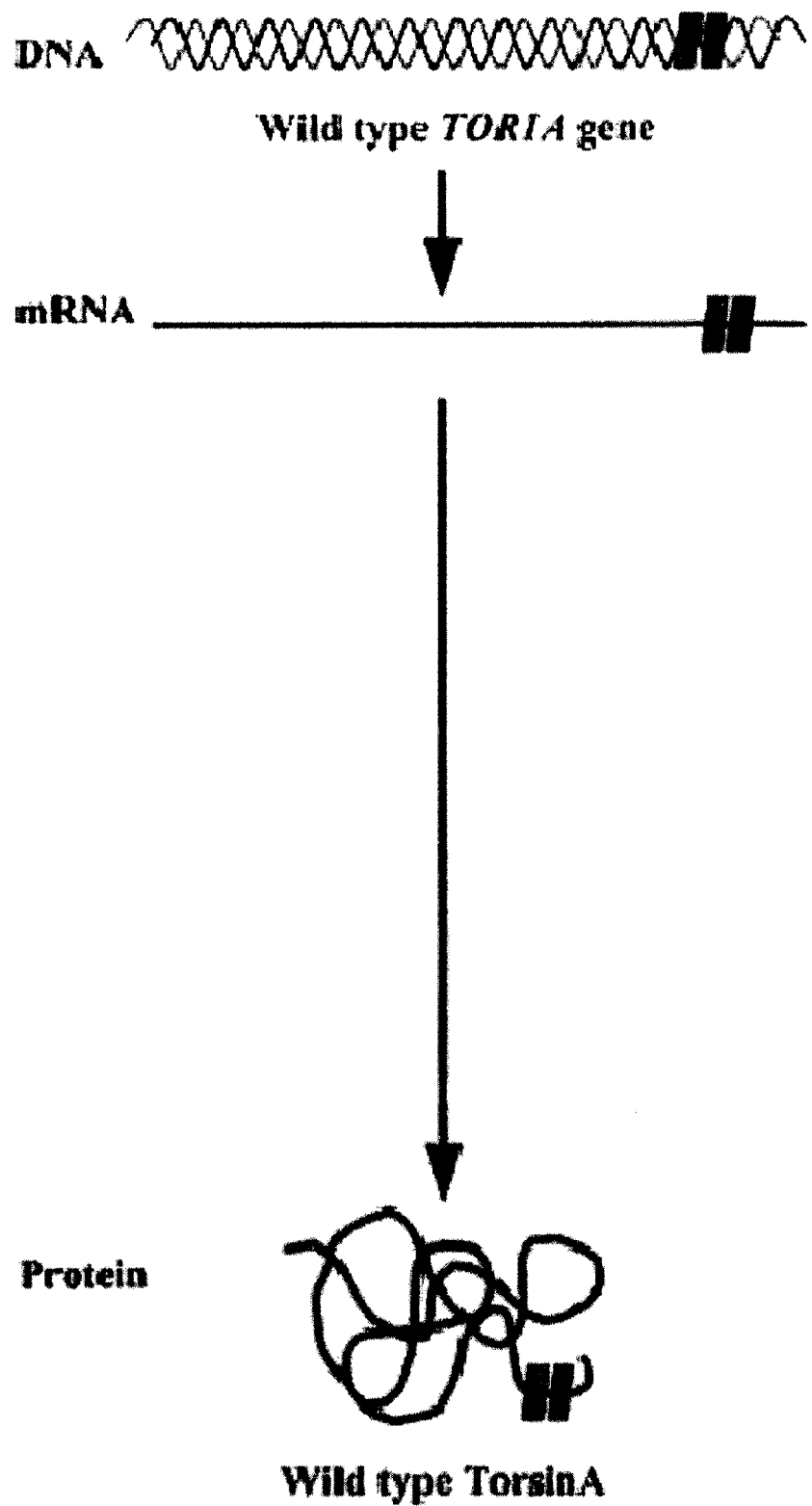
FIGS. 11A-11B. Schematic diagram of allele-specific silencing of mutant TorsinA by small interfering RNA (siRNA). In the disease state, wild type and mutant alleles of TOR1A are both transcribed into mRNA. siRNA with sequence identical to the mutant allele (deleted of GAG) should bind mutant mRNA selectively and mediate its degradation by the RNA-induced silencing complex (RISC) (circle). Wild type mRNA, not recognized by the mutant-specific siRNA, will remain and continue to be translated into normal TorsinA (FIG. 11A). The two adjacent GAG's in wild type TOR1A alleles are shown as two parallelograms, one of which is deleted in mutant TOR1A alleles (FIG. 11B).
Figure 11B:
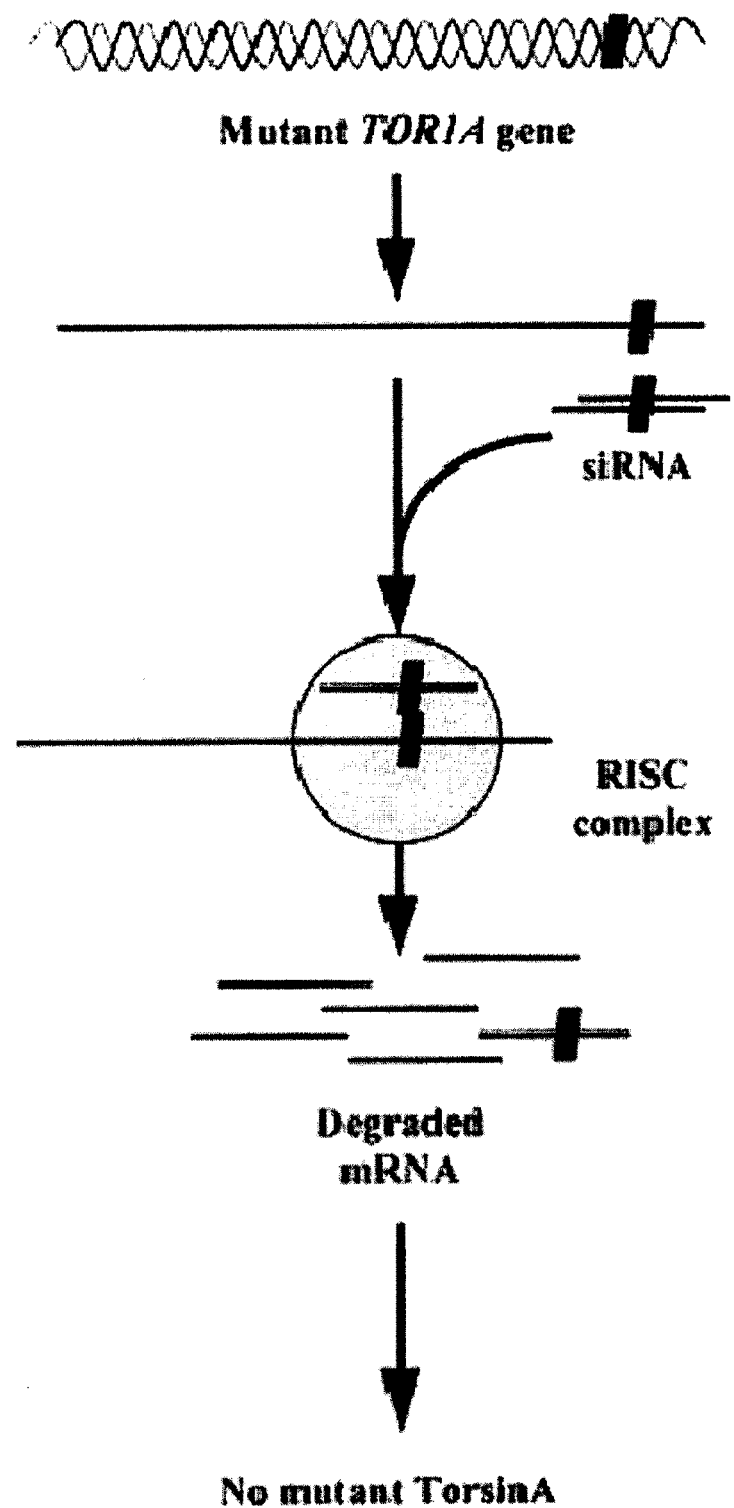

As outlined in the strategy in FIG. 11, the inventors developed siRNA that would specifically eliminate production of protein from the mutant allele. By exploiting the three base pair difference between wild type and mutant alleles, the inventors successfully silenced expression of the mutant protein (TAmut) without interfering with expression of the wild type protein (TAwt). Because TAwt may be an essential protein it is critically important that efforts be made to silence only the mutant allele. This allele-specific strategy has obvious therapeutic potential for DYT1 and represents a novel and powerful research tool with which to investigate the function of TA and its dysfunction in the disease state.

Expansions of poly-glutamine tracts in proteins that are expressed in the central nervous system can cause neurodegenerative diseases. Some neurodegenerative diseases are caused by a $(CAG)_n$ repeat that encodes poly-glutamine in a protein include Huntington disease (HD), spinocerebellar ataxia (SCA1, SCA2, SCA3, SCA6, SCA7), spinal and bulbar muscular atrophy (SBMA), and dentatorubropallidoluysian atrophy (DRPLA). In these diseases, the poly-glutamine expansion in a protein confers a novel toxic property upon the protein. Studies indicate that the toxic property is a tendency for the disease protein to misfold and form aggregates within neurons.

The gene involved in Huntington's disease (IT-15) is located at the end of the short arm of chromosome 4. This gene is designated HD and encodes the protein huntingtin (also known as Htt). A mutation occurs in the coding region of this gene and produces an unstable expanded trinucleotide repeat (cytosine-adenosine-guanosine), resulting in a protein with an expanded glutamate sequence. The normal and abnormal functions of this protein (termed huntingtin) are unknown. The abnormal huntingtin protein appears to accumulate in neuronal nuclei of transgenic mice, but the causal relationship of this accumulation to neuronal death is uncertain.

One of skill in the art can select additional target sites for generating siRNA specific for other alleles beyond those specifically described in the experimental examples. Such allele-specific siRNAs made be designed using the guidelines provided by Ambion (Austin, Tex.). Briefly, the target cDNA sequence is scanned for target sequences that had AA di-nucleotides. Sense and anti-sense oligonucleotides are generated to these targets (AA+3' adjacent 19 nucleotides) that contained a G/C content of 35 to 55%. These sequences are then compared to others in the human genome database to minimize homology to other known coding sequences (BLAST search).

To accomplish intracellular expression of the therapeutic siRNA, an RNA molecule is constructed containing two complementary strands or a hairpin sequence (such as a 21-bp hairpin) representing sequences directed against the gene of interest. The siRNA, or a nucleic acid encoding the siRNA, is introduced to the target cell, such as a diseased brain cell. The siRNA reduces target mRNA and protein expression.

The construct encoding the therapeutic siRNA is configured such that the one or more strands of the siRNA are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, such as by injection, allowing for diminished target-gene expression in the cell.

It was surprising that a pol II promoter would be effective. While small RNAs with extensive secondary structure are routinely made from Pol III promoters, there is no a priori reason to assume that small interfering RNAs could be expressed from pol II promoters. Pol III promoters terminate in a short stretch of Ts (5 or 6), leaving a very small 3' end and allowing stabilization of secondary structure. Polymerase II transcription extends well past the coding and polyadenylation regions, after which the transcript is cleaved. Two adenylation steps occur, leaving a transcript with a tail of up to 200 As. This string of As would of course completely destabilize any small, 21 base pair hairpin. Therefore, in addition to modifying the promoter to minimize sequences between the transcription start site and the siRNA sequence (thereby stabilizing the hairpin), the inventors also extensively modified the polyadenylation sequence to test if a very short polyadenylation could occur. The results, which were not predicted from prior literature, showed that it could.

The present invention provides an expression cassette containing an isolated nucleic acid sequence encoding a small interfering RNA molecule (siRNA) targeted against a gene of interest. The siRNA may form a hairpin structure that contains a duplex structure and a loop structure. The loop structure may contain from 4 to 10 nucleotides, such as 4, 5 or 6 nucleotides. The duplex is less than 30 nucleotides in length, such as from 19 to 25 nucleotides. The siRNA may further contain an overhang region. Such an overhang may be a 3' overhang region or a 5' overhang region. The overhang region may be, for example, from 1 to 6 nucleotides in length. The expression cassette may further contain a pol II promoter, as described herein. Examples of pol II promoters include regulatable promoters and constitutive promoters. For example, the promoter may be a CMV or RSV promoter. The expression cassette may further contain a polyadenylation signal, such as a synthetic minimal polyadenylation signal. The nucleic acid sequence may further contain a marker gene. The expression cassette may be contained in a viral vector. An appropriate viral vector for use in the present invention may be an adenoviral, lentiviral, adeno-associated viral (AAV), poliovirus, herpes simplex virus (HSV) or murine Maloney-based viral vector. The gene of interest may be a gene associated with a condition amenable to siRNA therapy. Examples of such conditions include neurodegenerative diseases, such as a trinucleotide-repeat disease (e.g., polyglutamine repeat disease). Examples of these diseases include Huntington's disease, several spinocerebellar ataxias, and Alzheimer's disease. Alternatively, the gene of interest may encode a ligand for a chemokine involved in the migration of a cancer cell, or a chemokine receptor.

The present invention also provides an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a small interfering RNA molecule (siRNA) targeted against a gene of interest. The expression cassette may be contained in a vector, such as a viral vector.

The present invention provides a method of reducing the expression of a gene product in a cell by contacting a cell with an expression cassette described above. It also provides a method of treating a patient by administering to the patient a composition of the expression cassette described above.

The present invention further provides a method of reducing the expression of a gene product in a cell by contacting a cell with an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a small interfering RNA molecule (siRNA) targeted against a gene of interest.

The present invention also provides a method of treating a patient, by administering to the patient a composition containing an expression cassette, wherein the expression cassette contains an isolated nucleic acid sequence encoding a first segment, a second segment located immediately 3' of the first segment, and a third segment located immediately 3' of the second segment, wherein the first and third segments are each less than 30 bases in length and each more than 10 bases in length, and wherein the sequence of the third segment is the complement of the sequence of the first segment, and wherein the isolated nucleic acid sequence functions as a small interfering RNA molecule (siRNA) targeted against a gene of interest.

RNAi holds promise as a potential therapy for human diseases. Yet a limitation to successfully developing gene-specific or allele-specific siRNAs is the selection and design of siRNAs with the desired silencing characteristics. Individual siRNAs targeted to different regions of a transcript often display striking differences in efficacy and specificity (Miller et al., 2003; Ding et al., 2003). Typically, several target sites and designs need to be tested before optimal silencing is achieved (Miller et al., 2003). Here the inventors have described a simple method that not only circumvents the time and cost disadvantages of chemically synthesizing siRNA duplexes but also removes the sequence restrictions imposed by in vitro transcription with T7 polymerase.

The insertion of a single G mismatch at the 5' of the siRNA duplex permitted efficient priming by T7 polymerase without compromising the silencing efficacy of the resultant siRNA. Such "+G" siRNAs can rapidly be generated to essentially any point in a targeted gene and tested for efficacy. This approach to siRNA design facilitates the in vitro generation of effective siRNAs. As demonstrated here for two important disease targets, tau and APP, these in vitro transcribed duplexes can then serve as guides for producing shRNA plasmids that retain silencing capability and allele specificity. This approach represents an improved, stepwise method for optimized silencing of essentially any gene of interest.

Indeed, based on new insights into RISC assembly, manipulating the 5' terminal nucleotide of the guide strand in this way may be highly advantageous. Schwarz et al. (Schwarz et al., 2003) recently discovered marked asymmetry in the rate at which each strand of an RNA duplex enters the RISC complex. Preferential entry of the guide, or antisense, strand into RISC can be achieved by introducing 5' mismatches in the antisense strand while maintaining perfect base pairing at the 5' terminus of the sense strand. This maximizes entry of the antisense strand into the RISC complex, while also reducing potential off-target inhibition by the sense strand. The "+G" approach to siRNA design is perfectly suited to engineering dsRNAs based on this principle that should display preferred RISC entry of the guide strand.

The inventors have also discovered that central placement of mismatches is required for allelic discrimination. Using the present approach to in vitro siRNA production, the inventors systematically tested the effect of placing mismatches at each point along the guide strand of the siRNA. The inventors have found that central placement of mismatches resulted in optimal allele-specific silencing of mutant alleles.

I. Definitions

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., (1991); Ohtsuka et al., (1985); Rossolini et al., (1994)).

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins.

The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid", "nucleic acid molecule", "nucleic acid fragment", "nucleic acid sequence or segment", or "polynucleotide" are used interchangeably and may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or RNA molecule or an "isolated" or "purified" polypeptide is a DNA molecule, RNA molecule, or polypeptide that exists apart from its native environment and is therefore not a product of nature. An isolated DNA molecule, RNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid)

in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, or 5% (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

"Naturally occurring" is used to describe an object that can be found in nature as distinct from being artificially produced. For example, a protein or nucleotide sequence present in an organism (including a virus), which can be isolated from a source in nature and which has not been intentionally modified by a person in the laboratory, is naturally occurring.

The term "chimeric" refers to a gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

A "foreign" gene refers to a gene not normally found in the host organism that has been introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell (2001).

The terms "heterologous gene", "heterologous DNA sequence", "exogenous DNA sequence", "heterologous RNA sequence", "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest but may also code for a functional RNA of interest, for example an antisense RNA, a nontranslated RNA in the sense or antisense direction, or a siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of an regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters. Examples of promoters that may be used in the present invention include CMV, RSV, polII and polIII promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Preferred, non-limiting examples of such mathematical algorithms are the algorithm of Myers and Miller (1988); the local homology algorithm of Smith et al. (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller, supra. The BLAST programs of Altschul et al. (1990), are based on the algorithm of Karlin and Altschul supra.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See http://www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (also called "truncation") or addition of one or more amino acids to the N-terminal and/or C-terminal end of the native protein; deletion or addition of one or more amino acids at one or more sites in the native protein; or substitution of one or more amino acids at one or more sites in the native protein. Such variants may results from, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985); Kunkel et al. (1987); U.S. Pat. No. 4,873,192; Walker and Gaastra (1983), and the references cited therein. Guidance as to appropriate amino acid substitutions that do not affect biological activity of the protein of interest may be found in the model of Dayhoff et al. (1978). Conservative substitutions, such as exchanging one amino acid with another having similar properties, are preferred.

Thus, the genes and nucleotide sequences of the invention include both the naturally occurring sequences as well as variant forms. Likewise, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells, and organisms comprising transgenic cells are referred to as "transgenic organisms".

"Transformed", "transduced", "transgenic", and "recombinant" refer to a host cell or organism into which a heterologous nucleic acid molecule has been introduced. The nucleic acid molecule can be stably integrated into the genome generally known in the art and are disclosed in Sambrook and Russell, infra. See also Innis et al. (1995); and Gelfand (1995); and Innis and Gelfand (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

The term "fusion protein" is intended to describe at least two polypeptides, typically from different sources, which are operably linked. With regard to polypeptides, the term operably linked is intended to mean that the two polypeptides are connected in a manner such that each polypeptide can serve its intended function. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

As used herein, the term "derived" or "directed to" with respect to a nucleotide molecule means that the molecule has complementary sequence identity to a particular molecule of interest.

"Gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference (for a review, see Brantl, 2002). In some embodiments, gene silencing may be allele-specific. "Allele-specific" gene silencing refers to the specific silencing of one allele of a gene.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. For example, the expression may be reduced by 10, 20, 30, 40, 50, 60, 70, 80, 90, 95, or even 99%. Knock-down of gene expression can be directed by the use of dsRNAs or siRNAs. For example, "RNA interference (RNAi)," which can involve the use of siRNA, has been successfully applied to knockdown the expression of specific genes in plants, *D. melanogaster, C. elegans*, trypanosomes, planaria, hydra, and several vertebrate species including the mouse. For a review of the mechanisms proposed to mediate RNAi, please refer to Bass et al., 2001, Elbashir et al., 2001 or Brantl 2002.

"RNA interference (RNAi)" is the process of sequence-specific, post-transcriptional gene silencing initiated by siRNA. RNAi is seen in a number of organisms such as *Drosophila*, nematodes, fungi and plants, and is believed to be involved in anti-viral defense, modulation of transposon activity, and regulation of gene expression. During RNAi, siRNA induces degradation of target mRNA with consequent sequence-specific inhibition of gene expression.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Treating" as used herein refers to ameliorating at least one symptom of, curing and/or preventing the development of a disease or a condition.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCAT, and SCA17), spinal and bulbar muscular atrophy (SBMA), dentatorubropallidoluysian atrophy (DRPLA). An example of a neurological disorder that does not appear to result in atrophy is DYT1 dystonia.

II. Nucleic Acid Molecules of the Invention

Sources of nucleotide sequences from which the present nucleic acid molecules can be obtained include any vertebrate, preferably mammalian, cellular source.

As discussed above, the terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an siRNA. Such an isolated siRNA may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al. (1981), and Goeddel et al. (1980). Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. This technique is known in the art as described by Adelman et al. (1983). Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. (1987). Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

III. Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein. For example, Sambrook and Russell, infra, provides suitable methods of construction.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described hereinbelow, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed above, a "transfected", "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell", comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

IV. Promoters of the Invention

As described herein, an expression cassette of the invention contains, inter alia, a promoter. Such promoters include the CMV promoter, as well as the RSV promoter, SV40 late promoter and retroviral LTRs (long terminal repeat elements), or brain cell specific promoters, although many other promoter elements well known to the art, such as tissue specific promoters or regulatable promoters may be employed in the practice of the invention.

In one embodiment of the present invention, an expression cassette may contain a pol II promoter that is operably linked to a nucleic acid sequence encoding a siRNA. Thus, the pol II promoter, i.e., a RNA polymerase II dependent promoter, initiates the transcription of the siRNA. In another embodiment, the pol II promoter is regulatable.

Three RNA polymerases transcribe nuclear genes in eukaryotes. RNA polymerase II (pol II) synthesizes mRNA, i.e., pol II transcribes the genes that encode proteins. In contrast, RNA polymerase I (pol I) and RNA polymerase III (pol III) transcribe only a limited set of transcripts, synthesizing RNAs that have structural or catalytic roles. RNA polymerase I makes the large ribosomal RNAs (rRNA), which are under the control of pol I promoters. RNA polymerase III makes a variety of small, stable RNAs, including the small 5S rRNA and transfer RNAs (tRNA), the transcription of which is under the control of pol III promoters.

As described herein, the inventors unexpectedly discovered that pol II promoters are useful to direct transcription of the siRNA. This was surprising because, as discussed above, pol II promoters are thought to be responsible for transcription of messenger RNA, i.e., relatively long RNAs as compared to RNAs of 30 bases or less.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the siRNA may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference).

In one embodiment, a pol II promoter that effectively directs the expression of the siRNA in the cell type, organelle, and organism chosen for expression will be employed. Those of ordinary skill in the art of molecular biology generally know the use of promoters for protein expression, for example, see Sambrook and Russell (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

V. Methods for Introducing the Expression Cassettes of the Invention Into Cells

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including: calcium phosphate DNA co-precipitation (Methods in Molecular Biology (1991)); DEAE-dextran (supra); electroporation (supra); cationic liposome-mediated transfection (supra); and tungsten particle-facilitated microparticle bombardment (Johnston (1990)). Strontium phosphate DNA co-precipitation (Brash et al. (1987)) is also a transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR) (Scharfmann et al. (1991)), adenosine deaminase, phosphoglycerol kinase (PGK), pyruvate kinase, phosphoglycerol mutase, the beta-actin promoter (Lai et al. (1989)), and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides various methods for making and using the above-described genetically-modified cells.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

VI. Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus) (Temin (1986)).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Standard protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are provided in Kriegler (1990) and Murray (1991).

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have been reported to enhance expression of an inserted coding sequence in a variety of cell types (see e.g., Hilberg et al. (1987); Holland et al. (1987); Valerio et al. (1989). Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA carried by the vector to be integrated into the target genome (Miller et al. (1990)).

Another viral candidate useful as an expression vector for transformation of cells is the adenovirus, a double-stranded DNA virus. The adenovirus is infective in a wide range of cell types, including, for example, muscle and endothelial cells (Larrick and Burck (1991)). The adenovirus also has been used as an expression vector in muscle cells in vivo (Quantin et al. (1992)).

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself (Rosenfeld et al. (1991)). Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate siRNA in a brain cell or brain tissue. A suitable vector for this application is an FIV vector (Brooks et al. (2002); Alisky et al. (2000a)) or an AAV vector. For example, one may use AAV5 (Davidson et al. (2000); Alisky et al. (2000a)). Also, one may apply poliovirus (Bledsoe et al. (2000)) or HSV vectors (Alisky et al. (2000b)).

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection (Capecchi (1980)), electroporation (Andreason and Evans (1988), scrape loading, microparticle bombardment (Johnston (1990)) or by cellular uptake as a chemical complex (e.g., calcium or strontium co-precipitation, complexation with lipid, complexation with ligand) (Methods in Molecular Biology (1991)). Several commercial products are available for cationic liposome complexation including Lipofectin™ (Gibco-BRL, Gaithersburg, Md.) (Felgner et al. (1987)) and Transfectam™ (ProMega, Madison, Wis.) (Behr et al. (1989); Loeffler et al. (1990)). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

VII. Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state. Examples of targetable disease mutations include tau mutations that cause frontotemporal dementia and the GAG deletion in the TOR1A gene that causes DYT1 dystonia. An example of a targetable polymorphism that is not itself a mutation is the C/G single nucleotide polymorphism (G987C) in the MJD1 gene immediately downstream of the mutation that causes spinocerebellar ataxia type 3 and the polymorphism in exon 58 associated with Huntington's disease.

Single nucleotide polymorphisms comprise most of the genetic diversity between humans. Many disease genes, including the HD gene in Huntington's disease, contain numerous single nucleotide or multiple nucleotide polymorphisms that could be separately targeted in one allele vs. the other, as shown in FIG. 15. The major risk factor for developing Alzheimer's disease is the presence of a particular polymorphism in the apolipoprotein E gene.

A. Gene Defects

A number of diseases caused by gene defects have been identified. For example, this strategy can be applied to a major class of disabling neurological disorders. For example this strategy can be applied to the polyglutamine diseases, as is demonstrated by the reduction of polyglutamine aggregation in cells following application of the strategy. The neurodegenerative disease may be a trinucleotide-repeat disease, such as a disease associated with polyglutamine repeats, including Huntington's disease, and several spinocerebellar ataxias. Additionally, this strategy can be applied to a non-degenerative neurological disorder, such as DYT1 dystonia.

B. Acquired Pathologies

As used herein, "acquired pathology" refers to a disease or syndrome manifested by an abnormal physiological, biochemical, cellular, structural, or molecular biological state. For example, the disease could be a viral disease, such as hepatitis or AIDS.

C. Cancers

The condition amenable to gene silencing therapy alternatively can be a genetic disorder or an acquired pathology that is manifested by abnormal cell proliferation, e.g., cancer. According to this embodiment, the instant invention is useful for silencing a gene involved in neoplastic activity. The present invention can also be used to inhibit overexpression of one or several genes. The present invention can be used to treat neuroblastoma, medulloblastoma, or glioblastoma.

VIII. Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

Administration of siRNA may be accomplished through the administration of the nucleic acid molecule encoding the siRNA (see, for example, Feigner et al., U.S. Pat. No. 5,580,859, Pardoll et al. 1995; Stevenson et al. 1995; Moiling 1997; Donnelly et al. 1995; Yang et al. II; Abdallah et al. 1995). Pharmaceutical formulations, dosages and routes of administration for nucleic acids are generally disclosed, for example, in Feigner et al., supra.

The present invention envisions treating a disease, for example, a neurodegenerative disease, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The invention will now be illustrated by the following non-limiting Example.

Example 1 siRNA-Mediated Silencing of Genes Using Viral Vectors

In this Example, it is shown that genes can be silenced in an allele-specific manner. It is also demonstrated that viral-mediated delivery of siRNA can specifically reduce expression of targeted genes in various cell types, both in vitro and in vivo. This strategy was then applied to reduce expression of a neurotoxic polyglutamine disease protein. The ability of viral vectors to transduce cells efficiently in vivo, coupled with the efficacy of virally expressed siRNA shown here, extends the application of siRNA to viral-based therapies and in vivo targeting experiments that aim to define the function of specific genes.

Experimental Protocols

Generation of the Expression Cassettes and Viral Vectors.

The modified CMV (mCMV) promoter was made by PCR amplification of CMV by primers 5'-AAGGTACCAGATCTTAGTTATTAATAGTAATCAATTACGG-3' (SEQ ID NO:1) and 5'-GAATCGATGCATGCCTCGAGACGGTTCACTAAACCAGCTCTGC-3' (SEQ ID NO:2) with peGFPN1 plasmid (purchased from Clontech, Inc) as template. The mCMV product was cloned into the KpnI and ClaI sites of the adenoviral shuttle vector pAd5KnpA, and was named pmCMVknpA. To construct the minimal polyA cassette, the oligonucleotides, 5'-CTAGAACTAGTAATAAAGGATCCTTTATTTTCATTGGATCCGTGTGTTGGTTTTTTGTGTGCGGCCGCG-3' (SEQ ID NO:3) and 5'-TCGACGCGGCCGCACACAAAAAACCAACACACGGATCCAATGAAAATAAAGGATCCTTTATTACTAGTT-3' (SEQ ID NO:4), were used. The oligonucleotides contain SpeI and SalI sites at the 5' and 3' ends, respectively. The synthesized polyA cassette was ligated into SpeI, SalI digested pmCMVKnpA. The resultant shuttle plasmid, pmCMVmpA was used for construction of head-to-head 21 bp hairpins of eGFP (bp 418 to 438), human β-glucuronidase (bp 649 to 669), mouse β-glucuronidase (bp 646 to 666) or E. coli β-galactosidase (bp 1152-1172). The eGFP hairpins were also cloned into the Ad shuttle plasmid containing the commercially available CMV promoter and polyA cassette from SV40 large T antigen (pCMVsiGFPx). Shuttle plasmids were co-transfected into HEK293 cells along with the adenovirus backbones for generation of full-length Ad genomes. Viruses were harvested 6-10 days after transfection and amplified and purified as described (Anderson, R. D., et al., Gene Ther. 7:1034-1038 (2000)).

Northern Blotting.

Total RNA was isolated from HEK293 cells transfected by plasmids or infected by adenoviruses using TRIZOL® Reagent (Invitrogen™ Life Technologies, Carlsbad, Calif.) according to the manufacturer's instruction. RNAs (30 µg) were separated by electrophoresis on 15% (wt/vol) polyacrylamide-urea gels to detect transcripts, or on 1% agarose-formaldehyde gel for target mRNAs analysis. RNAs were transferred by electroblotting onto hybond N+ membrane (Amersham Pharmacia Biotech). Blots were probed with $^{32}$P-labeled sense (5'-CACAAGCTGGAGTACAACTAC-3' (SEQ ID NO:5)) or antisense (5'-GTACTTGTACTCCAGCTTTGTG-3' (SEQ ID NO:6)) oligonucleotides at 37° C. for 3 h for evaluation of siRNA transcripts, or probed for target mRNAs at 42° C. overnight. Blots were washed using standard methods and exposed to film overnight. In vitro studies were performed in triplicate with a minimum of two repeats.

In Vivo Studies and Tissue Analyses.

All animal procedures were approved by the University of Iowa Committee on the Care and Use of Animals. Mice were injected into the tail vein (n=10 per group) or into the brain (n=6 per group) as described previously (Stein, C. S., et al., J. Virol. 73:3424-3429 (1999)) with the virus doses indicated. Animals were sacrificed at the noted times and tissues harvested and sections or tissue lysates evaluated for β-glucuronidase expression, eGFP fluorescence, or β-galactosidase activity using established methods (Xia, H. et al., Nat. Biotechnol. 19:640-644 (2001)). Total RNA was harvested from transduced liver using the methods described above.

Cell Lines.

PC12 tet off cell lines (Clontech Inc., Palo Alto, Calif.) were stably transfected with a tetracycline regulatable plasmid into which was cloned GFPQ19 or GFPQ80 (Chai, Y. et al., J. Neurosci. 19:10338-10347 (1999)). For GFP-Q80, clones were selected and clone 29 chosen for regulatable properties and inclusion formation. For GFP-Q19 clone 15 was selected for uniformity of GFP expression following gene expression induction. In all studies 1.5 µg/ml dox was used to repress transcription. All experiments were done in triplicate and were repeated 4 times.

Results and Discussion

To accomplish intracellular expression of siRNA, a 21-bp hairpin representing sequences directed against eGFP was constructed, and its ability to reduce target gene expression in mammalian cells using two distinct constructs was tested.

Figure 1C:
Figure 1D:
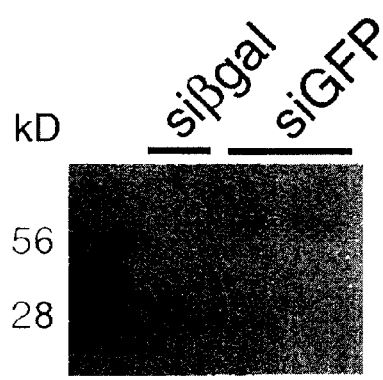
Figure 1E:
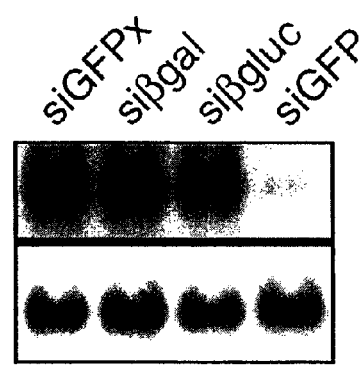

Initially, the siRNA hairpin targeted against eGFP was placed under the control of the CMV promoter and contained a full-length SV-40 polyadenylation (polyA) cassette (pCMVsiGFPx). In the second construct, the hairpin was juxtaposed almost immediate to the CMV transcription start site (within 6 bp) and was followed by a synthetic, minimal polyA cassette (FIG. 1A, pmCMVsiGFPmpA) (Experimental Protocols), because we reasoned that functional siRNA would require minimal to no overhangs (Caplan, N. J., et al., *Proc. Natl. Acad. Sci. U.S.A.* 98:9742-9747 (2001); Nykanen, A., et al., *Cell* 107:309-321 (2001)). Co-transfection of pmCMVsiGFPmpA with pEGFPN1 (Clontech Inc) into HEK293 cells markedly reduced eGFP fluorescence (FIG. 1C). pmCMVsiGFPmpA transfection led to the production of an approximately 63 bp RNA specific for eGFP (FIG. 1D), consistent with the predicted size of the siGFP hairpin-containing transcript. Reduction of target mRNA and eGFP protein expression was noted in pmCMVsiGFPmpA-transfected cells only (FIG. 1E, F). In contrast, eGFP RNA, protein and fluorescence levels remained unchanged in cells transfected with pEGFPN1 and pCMVsiGFPx (FIG. 1E, G), pEGFPN1 and pCMVsiβglucmpA (FIG. 1E, F, H), or pEGFPN1 and pCMVsiβgalmpA, the latter expressing siRNA against *E. coli* β-galactosidase (FIG. 1E). These data demonstrate the specificity of the expressed siRNAs.

Constructs identical to pmCMVsiGFPmpA, except that a spacer of 9, 12 and 21 nucleotides was present between the transcription start site and the 21 bp hairpin, were also tested. In each case, there was no silencing of eGFP expression (data not shown). Together the results indicate that the spacing of the hairpin immediate to the promoter can be important for functional target reduction, a fact supported by recent studies in MCF-7 cells (Brummelkamp, T. R., et al., *Science* 296:550-553 (2002)).

Figure 1I:
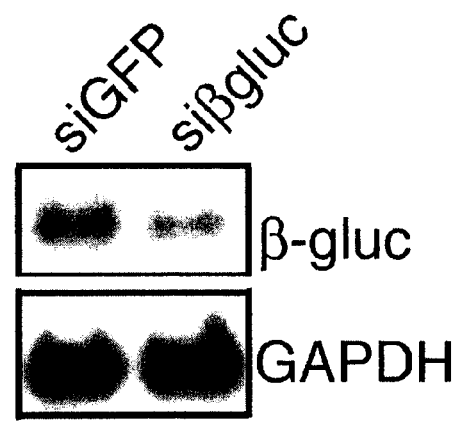
Figure 1J:
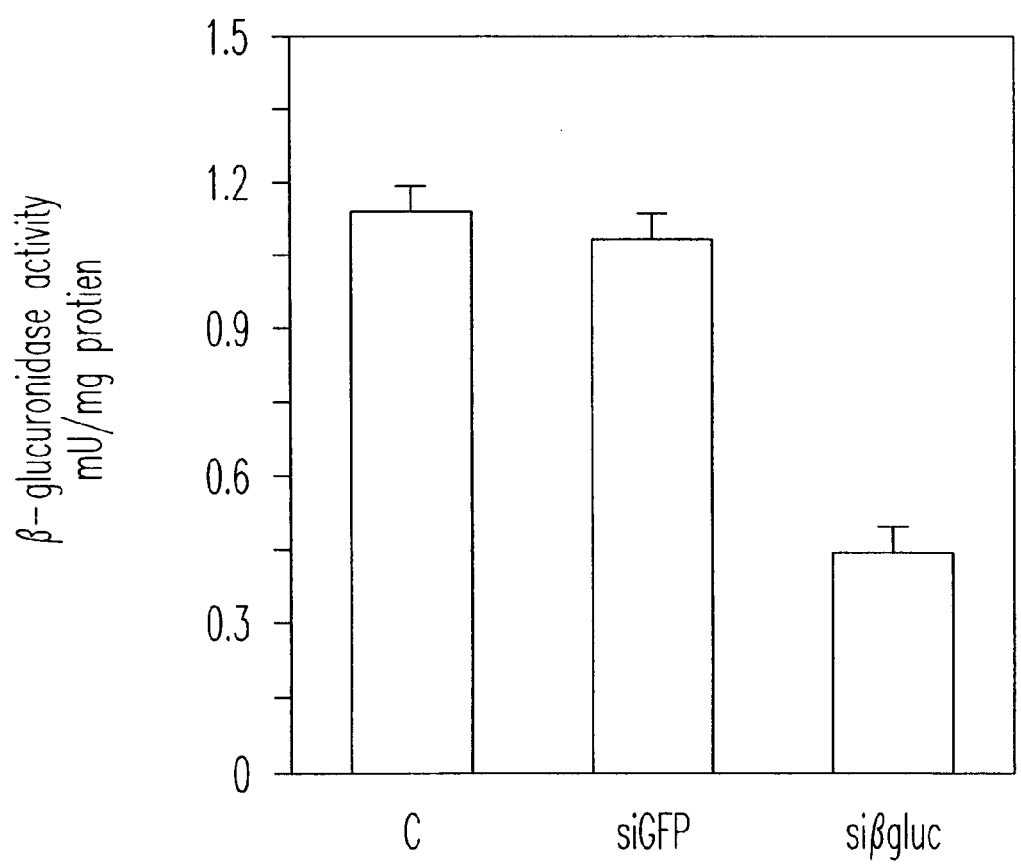

Recombinant adenoviruses were generated from the siGFP (pmCMVsiGFPmpA) and siβgluc (pmCMVsiβglucmpA) plasmids (Xia, H., et al., *Nat. Biotechnol.* 19:640-644 (2001); Anderson, R. D., et al., *Gene Ther.* 7:1034-1038 (2000)) to test the hypothesis that virally expressed siRNA allows for diminished gene expression of endogenous targets in vitro and in vivo. HeLa cells are of human origin and contain moderate levels of the soluble lysosomal enzyme β-glucuronidase. Infection of HeLa cells with viruses expressing siβgluc caused a specific reduction in human β-glucuronidase mRNA (FIG. 1I) leading to a 60% decrease in β-glucuronidase activity relative to siGFP or control cells (FIG. 1J). Optimization of siRNA sequences using methods to refine target mRNA accessible sequences (Lee, N. S., et al., *Nat. Biotechnol.* 19:500-505 (2002)) could improve further the diminution of β-glucuronidase transcript and protein levels.

The results in FIG. 1 are consistent with earlier work demonstrating the ability of synthetic 21-bp double stranded RNAs to reduce expression of target genes in mammalian cells following transfection, with the important difference that in the present studies the siRNA was synthesized intracellularly from readily available promoter constructs. The data support the utility of regulatable, tissue or cell-specific promoters for expression of siRNA when suitably modified for close juxtaposition of the hairpin to the transcriptional start site and inclusion of the minimal polyA sequence containing cassette (see, Methods above).

Figure 2B:

To evaluate the ability of virally expressed siRNA to diminish target-gene expression in adult mouse tissues in vivo, transgenic mice expressing eGFP (Okabe, M. et al., *FEBS Lett.* 407:313-319 (1997)) were injected into the striatal region of the brain with $1 \times 10^7$ infectious units of recombinant adenovirus vectors expressing siGFP or control siβgluc. Viruses also contained a dsRed expression cassette in a distant region of the virus for unequivocal localization of the injection site. Brain sections evaluated 5 days after injection by fluorescence (FIG. 2A) or western blot assay (FIG. 2B) demonstrated reduced eGFP expression. Decreased eGFP expression was confined to the injected hemisphere (FIG. 2B). The in vivo reduction is promising, particularly since transgenically expressed eGFP is a stable protein, making complete reduction in this short time frame unlikely. Moreover, evaluation of eGFP levels was done 5 days after injection, when inflammatory changes induced by the adenovirus vector likely enhance transgenic eGFP expression from the CMV enhancer (Ooboshi, H., et al., *Arterioscler. Thromb. Vasc. Biol.* 17:1786-1792 (1997)).

Figure 2C:
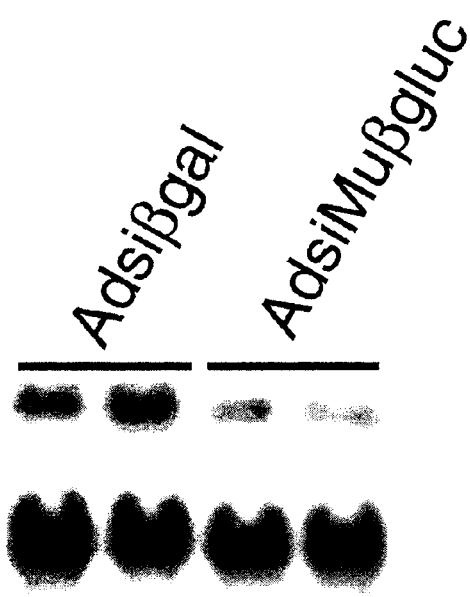

It was next tested whether virus mediated siRNA could decrease expression from endogenous alleles in vivo. Its ability to decrease β-glucuronidase activity in the murine liver, where endogenous levels of this relatively stable protein are high, was evaluated. Mice were injected via the tail vein with a construct expressing murine-specific siβgluc (AdsiMuβgluc), or the control viruses Adsiβgluc (specific for human β-glucuronidase) or Adsiβgal. Adenoviruses injected into the tail vein transduced hepatocytes as shown previously (Stein, C. S., et al., *J. Virol.* 73:3424-3429 (1999)). Liver tissue harvested 3 days later showed specific reduction of target β-glucuronidase RNA in AdsiMuβgluc treated mice only (FIG. 2C). Fluorometric enzyme assay of liver lysates confirmed these results, with a 12% decrease in activity from liver harvested from AdsiMuβgluc injected mice relative to Adsiβgal and Adsiβgluc treated ones (p<0.01; n=10). Interestingly, sequence differences between the murine and human siRNA constructs are limited, with 14 of 21 bp being identical. These results confirm the specificity of virus mediated siRNA, and indicate that allele-specific applications are possible. Together, the data are the first to demonstrate the utility of siRNA to diminish target gene expression in brain and liver tissue in vivo, and establish that allele-specific silencing in vivo is possible with siRNA.

Figure 3D:
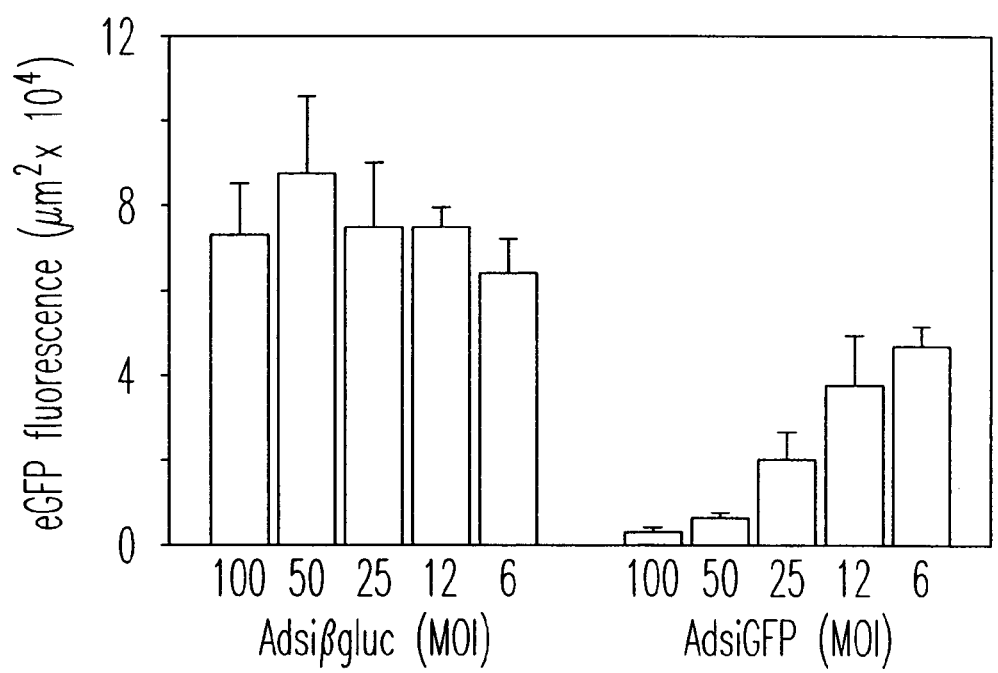

One powerful therapeutic application of siRNA is to reduce expression of toxic gene products in dominantly inherited diseases such as the polyglutamine (polyQ) neurodegenerative disorders (Margolis, R. L. & Ross, C. A. *Trends Mol. Med.* 7:479-482 (2001)). The molecular basis of polyQ diseases is a novel toxic property conferred upon the mutant protein by polyQ expansion. This toxic property is associated with disease protein aggregation. The ability of virally expressed siRNA to diminish expanded polyQ protein expression in neural PC-12 clonal cell lines was evaluated. Lines were developed that express tetracycline-repressible eGFP-polyglutamine fusion proteins with normal or expanded glutamine of 19 (eGFP-Q19) and 80 (eGFP-Q80) repeats, respectively. Differentiated, eGFP-Q19-expressing PC12 neural cells infected with recombinant adenovirus expressing siGFP demonstrated a specific and dose-dependent decrease in eGFP-Q19 fluorescence (FIG. 3A, C) and protein levels (FIG. 3B). Application of Adsiβgluc as a control had no effect (FIG. 3A-C). Quantitative image analysis of eGFP fluorescence demonstrated that siGFP reduced GFPQ19 expression by greater than 96% and 93% for 100 and 50 MOI respectively, relative to control siRNA (FIG. 3C). The multiplicity of infection (MOI) of 100 required to achieve maximal inhibition of eGFP-Q19 expression results largely from the inability of PC12 cells to be infected by adenovirus-based vectors. This barrier can be overcome using AAV- or lentivirus-based expression systems (Davidson, B. L., et al., *Proc. Natl. Acad. Sci. U.S.A.* 97:3428-3432 (2000); Brooks, A. I., et al, *Proc. Natl. Acad. Sci. U.S.A.* 99:6216-6221 (2002)).

Figure 4A:
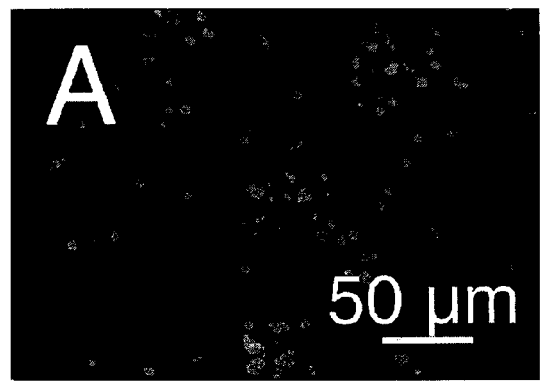
FIGS. 4A-4G. siRNA mediated reduction of expanded polyglutamine protein levels and intracellular aggregates. PC12 cells expressing tet-repressible eGFP-Q80 fusion proteins were washed to remove doxycycline and adenovirus vectors expressing siRNA were applied 3 days later. (A-D) Representative punctate eGFP fluorescence of aggregates in mock-infected cells (A), or those infected with 100 MOI of Adsiβgluc (B), AdsiGFPx (C) or Adsiβgal (D). (E) Three days after infection of dox-free eGFP-Q80 PC12 cells with AdsiGFP, aggregate size and number are notably reduced. (F) Western blot analysis of eGFP-Q80 aggregates (arrowhead) and monomer (arrow) following Adsiβgluc or AdsiGFP infection at the indicated MOIs demonstrates dose dependent siGFP-mediated reduction of GFP-Q80 protein levels. (G) Quantification of the total area of fluorescent inclusions measured in 4 independent fields/well 3 days after virus was applied at the indicated MOIs. The data are mean±standard deviation.
Figure 4B:
Figure 4C:
Figure 4D:
Figure 4E:
Figure 4F:
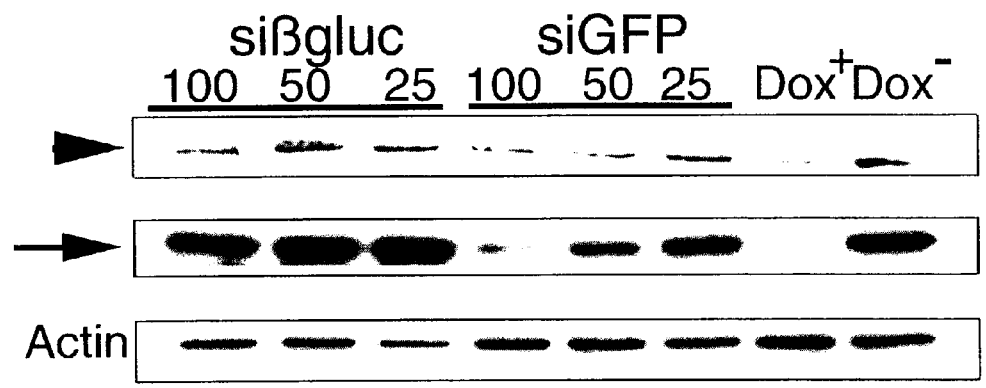
Figure 4G:
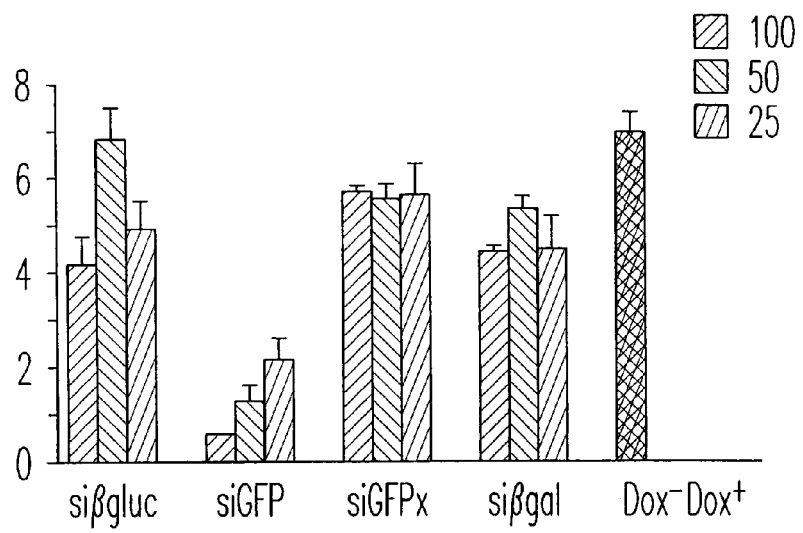

To test the impact of siRNA on the size and number of aggregates formed in eGFP-Q80 expressing cells, differentiated PC-12/eGFP-Q80 neural cells were infected with AdsiGFP or Adsiβgluc 3 days after doxycycline removal to induce GFP-Q80 expression. Cells were evaluated 3 days later. In mock-infected control cells (FIG. 4A), aggregates were very large 6 days after induction as reported by others (Chai, Y., et al., *J. Neurosci.* 19:10338-10347 (1999; Moulder, K. L., et al., *J. Neurosci.* 19:705-715 (1999)). Large aggregates were also seen in cells infected with Adsiβgluc (FIG. 4B), AdsiGFPx, (FIG. 4C, siRNA expressed from the normal CMV promoter and containing the SV40 large T antigen polyadenylation cassette), or Adsiβgal (FIG. 4D). In contrast, polyQ aggregate formation was significantly reduced in AdsiGFP infected cells (FIG. 4E), with fewer and smaller inclusions and more diffuse eGFP fluorescence. AdsiGFP-mediated reduction in aggregated and monomeric GFP-Q80 was verified by Western blot analysis (FIG. 4F), and quantitation of cellular fluorescence (FIG. 4G). AdsiGFP caused a dramatic and specific, dose-dependent reduction in eGFP-Q80 expression (FIG. 4F, G).

It was found that transcripts expressed from the modified CMV promoter and containing the minimal polyA cassette were capable of reducing gene expression in both plasmid and viral vector systems (FIGS. 1-4). The placement of the hairpin immediate to the transcription start site and use of the minimal polyadenylation cassette was of critical importance. In plants and *Drosophila*, RNA interference is initiated by the ATP-dependent, processive cleavage of long dsRNA into 21-25 bp double-stranded siRNA, followed by incorporation of siRNA into a RNA-induced silencing complex that recognizes and cleaves the target (Nykänen, A., et al., *Cell* 107:309-321 (2001); Zamore, P D., et al., *Cell* 101:25-33 (2000); Bernstein, E., et al., *Nature* 409:363-366 (2001); Hamilton, A. J. & Baulcombe, D. C. *Science* 286: 950-952 (1999); Hammond, S. M. et al., *Nature* 404:293-296 (2000)). Viral vectors expressing siRNA are useful in determining if similar mechanisms are involved in target RNA cleavage in mammalian cells in vivo.

In summary, these data demonstrate that siRNA expressed from viral vectors in vitro and in vivo specifically reduce expression of stably expressed plasmids in cells, and endogenous transgenic targets in mice. Importantly, the application of virally expressed siRNA to various target alleles in different cells and tissues in vitro and in vivo was demonstrated. Finally, the results show that it is possible to reduce polyglutamine protein levels in neurons, which is the cause of at least nine inherited neurodegenerative diseases, with a corresponding decrease in disease protein aggregation. The ability of viral vectors based on adeno-associated virus (Davidson, B. L., et al., *Proc. Natl. Acad. Sci. U.S.A.* 97:3428-3432 (2000)) and lentiviruses (Brooks, A. I., et al., *Proc. Natl. Acad. Sci. U.S.A.* 99:6216-6221 (2002)) to efficiently transduce cells in the CNS, coupled with the effectiveness of virally-expressed siRNA demonstrated here, extends the application of siRNA to viral-based therapies and to basic research, including inhibiting novel ESTs to define gene function.

Example 2 siRNA Suppression of Genes Involved in MJD/SCA3 and FTDP-17

Modulation of gene expression by endogenous, noncoding RNAs is increasingly appreciated to play a role in eukaryotic development, maintenance of chromatin structure and genomic integrity. Recently, techniques have been developed to trigger RNA interference (RNAi) against specific targets in mammalian cells by introducing exogenously produced or intracellularly expressed siRNAs. These methods have proven to be quick, inexpensive and effective for knockdown experiments in vitro and in vivo. The ability to accomplish selective gene silencing has led to the hypothesis that siRNAs might be employed to suppress gene expression for therapeutic benefit.

Dominantly inherited diseases are ideal candidates for siRNA-based therapy. To explore the utility of siRNA in inherited human disorders, the inventors employed cellular models to test whether we could target mutant alleles causing two classes of dominantly inherited, untreatable neurodegenerative diseases: polyglutamine (polyQ) neurodegeneration in MJD/SCA3 and frontotemporal dementia with parkinsonism linked to chromosome 17 (FTDP-17). The polyQ neurodegenerative disorders consist of at least nine diseases caused by CAG repeat expansions that encode polyQ in the disease protein. PolyQ expansion confers a dominant toxic property on the mutant protein that is associated with aberrant accumulation of the disease protein in neurons. In FTDP-17, Tau mutations lead to the formation of neurofibrillary tangles accompanied by neuronal dysfunction and degeneration. The precise mechanisms by which these mutant proteins cause neuronal injury are unknown, but considerable evidence suggests that the abnormal proteins themselves initiate the pathogenic process. Accordingly, eliminating expression of the mutant protein by siRNA or other means should, in principle, slow or even prevent disease. However, because many dominant disease genes may also encode essential proteins, the inventors sought to develop siRNA-mediated approaches that selectively inactivate mutant alleles while allowing continued expression of the wild type protein.

Methods siRNA Synthesis.

In vitro siRNA synthesis was previously described (Donze 2000). Reactions were performed with desalted DNA oligonucleotides (IDT Coralville, Iowa) and the AmpliScribeT7 High Yield Transcription Kit (Epicentre Madison, Wis.). Yield was determined by absorbance at 260 nm. Annealed siRNAs were assessed for double stranded character by agarose gel (1% w/v) electrophoresis and ethidium bromide staining. Note that for all siRNAs generated in this study the most 5' nucleotide in the targeted cDNA sequence is referred to as position 1 and each subsequent nucleotide is numbered in ascending order from 5' to 3'.

Plasmid Construction.

The human ataxin-3 cDNA was expanded to 166 CAG's by PCR (Laccone 1999). PCR products were digested at BamHI and KpnI sites introduced during PCR and ligated into BglII and KpnI sites of pEGFP-N1 (Clontech) resulting in full-length expanded ataxin-3 fused to the N-terminus of EGFP. Untagged Ataxin-3-Q166 was constructed by ligating a PpuMI-NotI ataxin-3 fragment (3' of the CAG repeat) into Ataxin-3-Q166-GFP cut with PpuMI and NotI to remove EGFP and replace the normal ataxin-3 stop codon. Ataxin-3-Q28-GFP was generated as above from pcDNA3.1-ataxin-3-Q28. Constructs were sequence verified to ensure that no PCR mutations were present. Expression was verified by Western blot with anti-ataxin-3 (Paulson 1997) and GFP antibodies (MBL). The construct encoding a flag tagged, 352 residue tau isoform was previously described (Leger 1994). The pEGFP-tau plasmid was constructed by ligating the human tau cDNA into pEGFP-C2 (Clontech) and encodes tau with EGFP fused to the amino terminus. The pEGFP-tauV337M plasmid was derived using site-directed mutagenesis (QuikChange Kit, Stratagene) of the pEFGP-tau plasmid.

Cell Culture and Transfections.

Culture of Cos-7 and HeLa cells has been described (Chai 1999b). Transfections with plasmids and siRNA were performed using Lipofectamine Plus (LifeTechnologies) according to the manufacturer's instructions. For ataxin-3 expression 1.5 µg plasmid was transfected with 5 µg in vitro synthesized siRNAs. For Tau experiments 1 µg plasmid was transfected with 2.5 µg siRNA. For expression of hairpin siRNA from the phU6 constructs, 1 µg ataxin-3 expression plasmid was transfected with 4 µg phU6-siC10i or phU6-siG10i. Cos-7 cells infected with siRNA-expressing adenovirus were transfected with 0.5 µg of each expression plasmid.

Stably transfected, doxycycline-inducible cell lines were generated in a subclone of PC12 cells, PC6-3, because of its strong neural differentiation properties (Pittman 19938). A PC6-3 clone stably expressing Tet repressor plasmid (provided by S. Strack, Univ. of Iowa), was transfected with pcDNA5/TO-ataxin-3(Q28) or pcDNA5/TO-ataxin-3(Q166) (Invitrogen). After selection in hygromycin, clones were characterized by Western blot and immunofluorescence. Two clones, PC6-3-ataxin3(Q28)#33 and PC6-3-ataxin3(Q166)#41, were chosen because of their tightly inducible, robust expression of ataxin-3.

siRNA Plasmid and Viral Production.

Plasmids expressing ataxin-3 shRNAs were generated by insertion of head-to-head 21 bp hairpins in phU6 that corresponded to siC10 and siG10 (Xia 2002).

Recombinant adenovirus expressing ataxin-3 specific shRNA were generated from phU6-C10i (encoding C10 hairpin siRNA) and phU6si-G10i (encoding G10 hairpin siRNA) as previously described (Xia 2002, Anderson 2000).

Western Blotting and Immunofluorescence.

Cos-7 cells expressing ataxin-3 were harvested 24-48 hours after transfection (Chai 1999b). Stably transfected, inducible cell lines were harvested 72 hours after infection with adenovirus. Lysates were assessed for ataxin-3 expression by Western blot analysis as previously described (Chai 1999b), using polyclonal rabbit anti-ataxin-3 antisera at a 1:15,000 dilution or 1C2 antibody specific for expanded polyQ tracts (Trottier 1995) at a 1:2,500 dilution. Cells expressing Tau were harvested 24 hours after transfection. Protein was detected with an affinity purified polyclonal antibody to a human tau peptide (residues 12-24) at a 1:500 dilution. Anti-alpha-tubulin mouse monoclonal antibody (Sigma St. Louis, Mo.) was used at a 1:10,000 dilution and GAPDH mouse monoclonal antibody (Sigma St. Louis, Mo.) was used at a 1:1,000 dilution.

Immunofluorescence for ataxin-3 (Chai 1999b) was carried out using 1C2 antibody (Chemicon International Temecula, Calif.) at 1:1,000 dilution 48 hours after transfection. Flag-tagged, wild type tau was detected using mouse monoclonal antibody (Sigma St. Louis, Mo.) at 1:1,000 dilution 24 hours after transfection. Both proteins were detected with rhodamine conjugated secondary antibody at a 1:1,000 dilution.

Fluorescent Imaging and Quantification.

Fixed samples were observed with a Zeiss Axioplan fluorescence microscope. Digital images were collected on separate red, green and blue fluorescence channels using a SPOT digital camera. Images were assembled and overlaid using Adobe Photoshop 6.0. Live cell images were collected with a Kodak MDS 290 digital camera mounted to an Olympus (Tokyo, Japan) CK40 inverted microscope. Fluorescence was quantitated by collecting 3 non-overlapping images per well at low power (10×). Pixel count and intensity for each image was determined using Bioquant Nova Prime software (BIOQUANT Image Analysis Corporation). Background was subtracted by quantitation of images from cells of equivalent density under identical fluorescent illumination. Mock transfected cells were used to assess background fluorescence for all experiments and were stained with appropriate primary and secondary antibodies for simulated heterozygous experiments. Average fluorescence is reported from 2 to 3 independent experiments. The mean of 2 to 3 independent experiments for cells transfected with the indicated expression plasmid and siMiss was set at one. Errors bars depict variation between experiments as standard error of the mean. In simulated heterozygous experiments, a blinded observer scored cells with a positive fluorescence signal for expression of wild type, mutant or both proteins in random fields at high power for two independent experiments. More than 100 cells were scored in each experiment and reported as number of cells with co-expression divided by total number of transfected cells.

Results

Direct Silencing of Expanded Alleles.

Figure 5A:
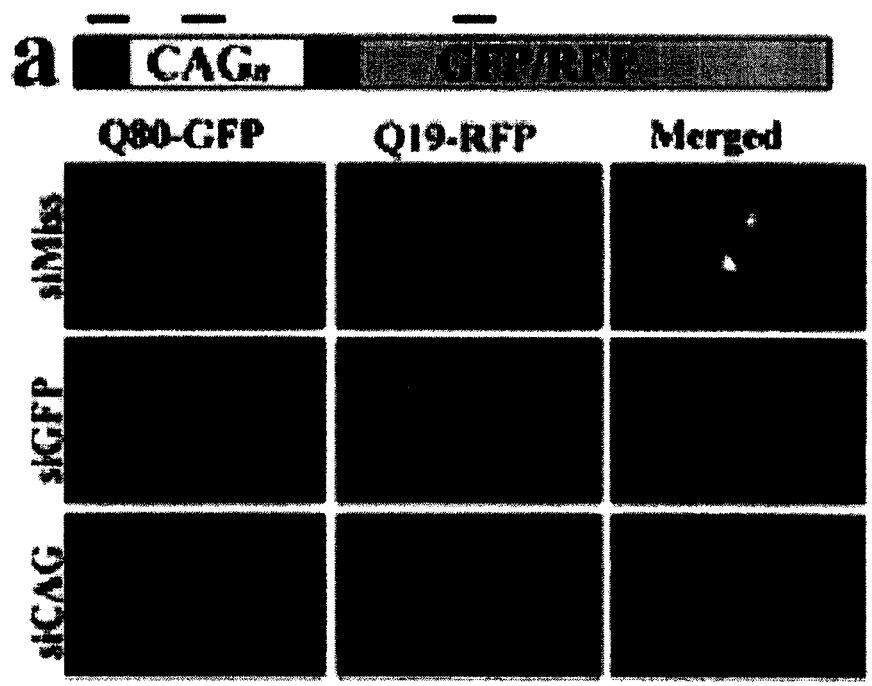
FIGS. 5A-5F. RNAi-mediated suppression of expanded CAG repeat containing genes. Expanded CAG repeats are not direct targets for preferential inactivation (A), but a linked SNP can be exploited to generate siRNA that selectively silences mutant ataxin-3 expression (B-F). (A) Schematic of cDNA encoding generalized polyQ-fluorescent protein fusions. Bars indicate regions targeted by siRNAs. HeLa cells co-transfected with Q80-GFP, Q19-RFP and the indicated siRNA. Nuclei are visualized by DAPI staining (blue) in merged images. (B) Schematic of human ataxin-3 cDNA with bars indicating regions targeted by siRNAs. The targeted SNP (G987C) is shown in color. In the displayed siRNAs, red or blue bars denote C or G respectively. In this Figure, AGCAGCAGCAGGGGGACCTATCAGGAC is SEQ ID NO:7, and CAGCAGCAGCAGCGGGAC-CTATCAGGAC is SEQ ID NO:8. (C) Quantitation of fluorescence in Cos-7 cells transfected with wild type or mutant ataxin-3-GFP expression plasmids and the indicated siRNA. Fluorescence from cells co-transfected with siMiss was set at one. Bars depict mean total fluorescence from three independent experiments +/−standard error of the mean (SEM). (D) Western blot analysis of cells co-transfected with the indicated ataxin-3 expression plasmids (top) and siRNAs (bottom). Appearance of aggregated, mutant ataxin-3 in the stacking gel (seen with siMiss and siG10) is prevented by siRNA inhibition of the mutant allele. (E) Allele specificity is retained in the simulated heterozygous state. Western blot analysis of Cos-7 cells cotransfected with wild-type (atx-3-Q28-GFP) and mutant (atx-Q166) expression plasmids along with the indicated siRNAs. (Mutant ataxin-3 detected with 1C2, an antibody specific for expanded polyQ, and wild-type ataxin-3 detected with anti-ataxin-3 antibody.) (F) Western blot of Cos-7 cells transfected with Atx-3-GFP expression plasmids and plasmids encoding the indicated shRNA. The negative control plasmid, phU6-LacZi, encodes siRNA specific for LacZ. Both normal and mutant protein were detected with anti-ataxin-3 antibody. Tubulin immunostaining shown as a loading control in panels (D)-(F).

The inventors first attempted suppression of mutant polyQ expression using siRNA complementary to the CAG repeat and immediately adjacent sequences to determine if the expanded repeat differentially altered the susceptibility of the mutant allele to siRNA inhibition (FIG. 6). HeLa cells were transfected with various in vitro synthesized siRNAs (Danze 2002) and plasmids encoding normal or expanded polyQ fused to red or green fluorescent protein, respectively (Q19-RFP and Q80-GFP) (FIG. 5a). In negative control cells transfected with Q80-GFP, Q19-RFP and a mistargeted siRNA (siMiss), Q80-GFP formed aggregates (Onodera 1997) which recruited the normally diffuse Q19-RFP (FIG. 5a). When the experiment was performed with siRNA targeted to GFP as a positive control for allele specific silencing, Q80-GFP expression was nearly abolished while Q19-RFP continued to be expressed as a diffusely distributed protein (FIG. 5a). When Q19-RFP and Q80-GFP were co-transfected with siRNA directly targeting the CAG repeat (siCAG) (FIG. 5a) or an immediately adjacent 5' region (data not shown), expression of both proteins was efficiently suppressed.

Figure 5B:
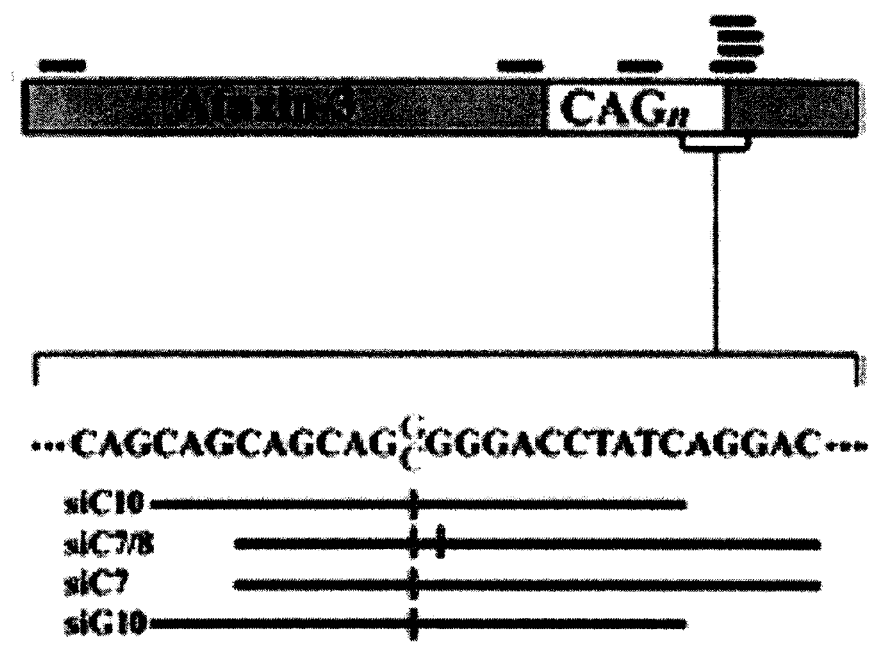

To test whether siRNA could selectively silence expression of a full-length polyQ disease protein, siRNAs were designed that target the transcript encoding ataxin-3, the disease protein in Machado-Joseph Disease, also known as Spinocerebellar Ataxia Type 3 (MJD/SCA3) (Zoghbi 2000) (FIG. 5b). In transfected cells, siRNA directed against three separate regions—the CAG repeat, a distant 5' site, or a site just 5' to the CAG repeat (siN'CAG)—resulted in efficient, but not allele-specific, suppression of ataxin-3 containing normal or expanded repeats (data not shown). Consistent with an earlier study using longer dsRNA (Caplen 2002) the present results show that expanded CAG repeats and adjacent sequences, while accessible to RNAi, may not be preferential targets for silencing.

Allele-Specific Silencing of the Mutant PolyQ Gene in MJD/SCA3.

Figure 5C:
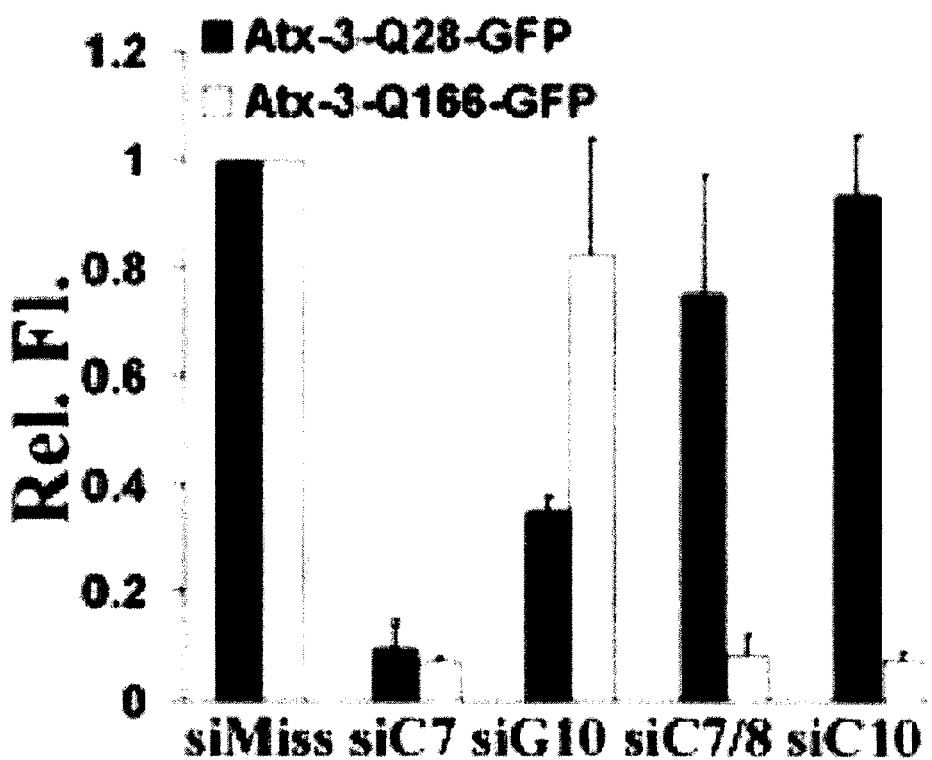
Figure 5D:
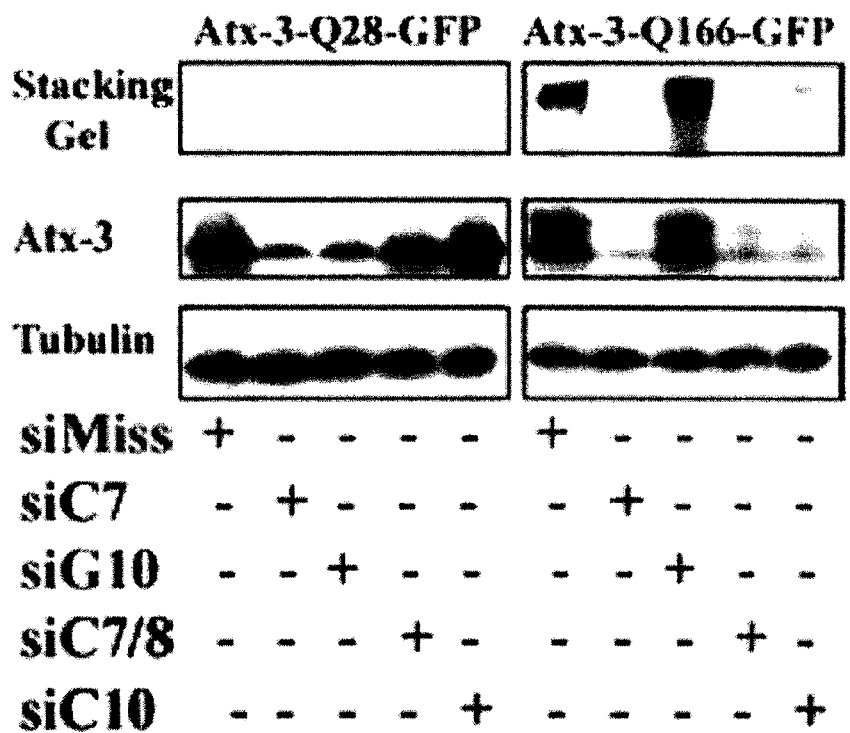

In further efforts to selectively inactivate the mutant allele the inventors took advantage of a SNP in the MJD1 gene, a G to C transition immediately 3' to the CAG repeat (G987C) (FIG. 5b). This SNP is in linkage disequilibrium with the disease-causing expansion, in most families segregating perfectly with the disease allele. Worldwide, 70% of disease chromosomes carry the C variant (Gaspar 2001). The present ataxin-3 expression cassettes, which were generated from patients (Paulson 1997), contain the C variant in all expanded ataxin-3 constructs and the G variant in all normal ataxin-3 constructs. To test whether this G-C mismatch could be distinguished by siRNA, siRNAs were designed that included the last 2 CAG triplets of the repeat followed by the C variant at position 7 (siC7) (FIG. 6 and FIG. 5b), resulting in a perfect match only for expanded alleles. Despite the presence of a single mismatch to the wild type allele, siC7 strongly inhibited expression of both alleles (FIG. 5c,d). A second G-C mismatch was then introduced at position 8 such that the siRNA contained two mismatches as compared to wild type and only one mismatch as compared to mutant alleles (siC7/8). The siC7/8 siRNA effectively suppressed mutant ataxin-3 expression, reducing total fluorescence to an average 8.6% of control levels, with only modest effects on wild type ataxin-3 (average 75.2% of control). siC7/8 also nearly eliminated the accumulation of aggregated mutant ataxin-3, a pathological hallmark of disease (Chan 2000) (FIG. 5d).

Figure 7A:
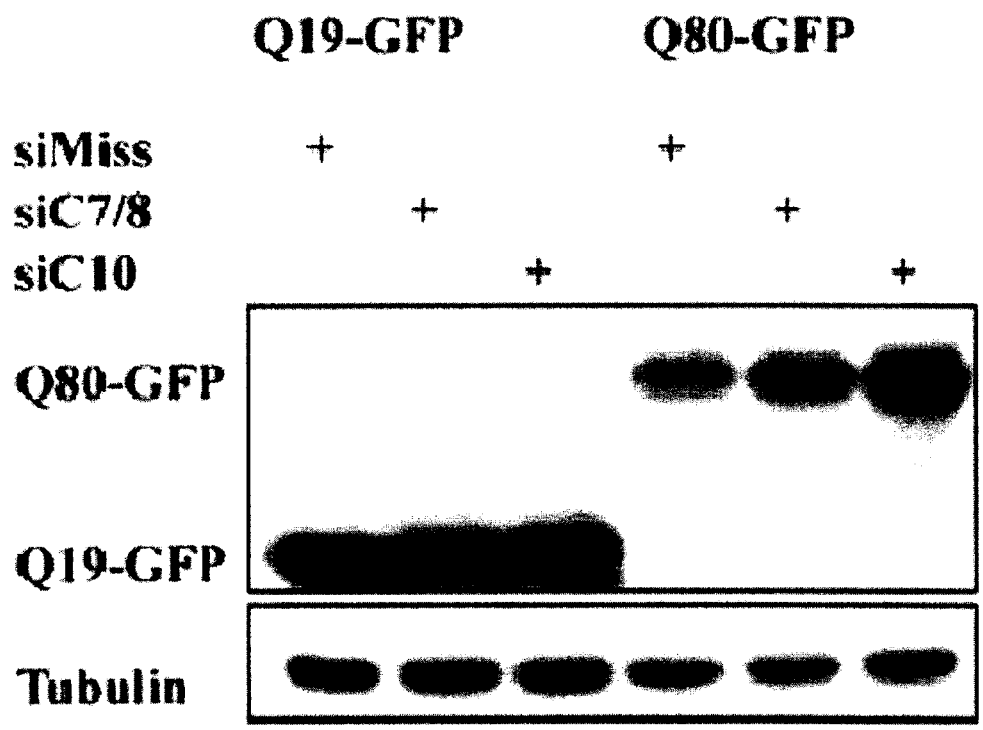
FIGS. 7A-7B. Inclusion of either two (siC7/8) or three (siC10) CAG triplets at the 5' end of ataxin-3 siRNA does not inhibit expression of unrelated CAG repeat containing genes. (A) Western blot analysis of Cos-7 cells transfected with CAG repeat-GFP fusion proteins and the indicated siRNA. Immunostaining with monoclonal anti-GFP antibody (MBL) at 1:1000 dilution. (B) Western blot analysis of Cos-7 cells transfected with Flag-tagged ataxin-1-Q30, which is unrelated to ataxin-3, and the indicated siRNA. Immunostaining with anti-Flag monoclonal antibody (Sigma St. Louis, Mo.) at 1:1000 dilution. In panels (A) and (B), lysates were collected 24 hours after transfection. Tubulin immunostaining shown as a loading control.
Figure 7B:
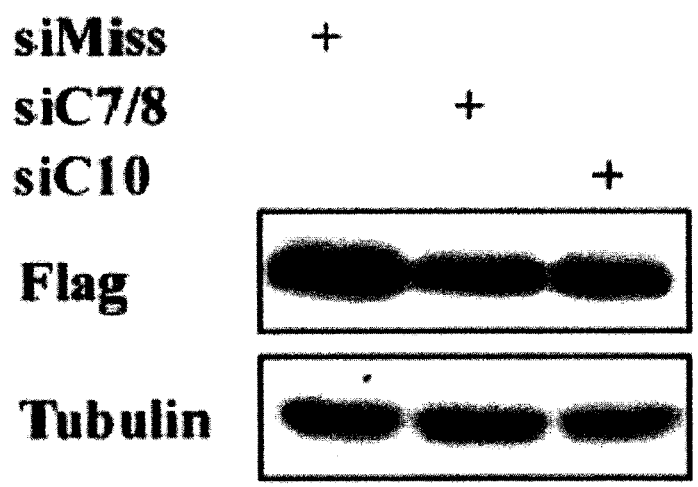

To optimize differential suppression, siRNAs were designed containing a more centrally placed mismatch. Because the center of the antisense strand directs cleavage of target mRNA in the RNA Induced Silencing Complex (RISC) complex (Elbashir 2001c), it was reasoned that central mismatches might more efficiently discriminate between wild type and mutant alleles. siRNAs were designed that place the C of the SNP at position 10 (siC10), preceded by the final three triplets in the CAG repeat (FIG. 6 and FIG. 5b). In transfected cells, siC10 caused allele-specific suppression of the mutant protein (FIG. 5c,d). Fluorescence from expanded Atx-3-Q166-GFP was dramatically reduced (7.4% of control levels), while fluorescence of Atx-3-Q28-GFP showed minimal change (93.6% of control; FIG. 5c,d). Conversely, siRNA engineered to suppress only the wild type allele (siG10) inhibited wild type expression with little effect on expression of the mutant allele (FIG. 5c,d). Inclusion of three CAG repeats at the 5' end of the siRNA did not inhibit expression of Q19-GFP, Q80-GFP, or full-length ataxin-1-Q30 proteins that are each encoded by CAG repeat containing transcripts (FIG. 7).

Figure 5E:
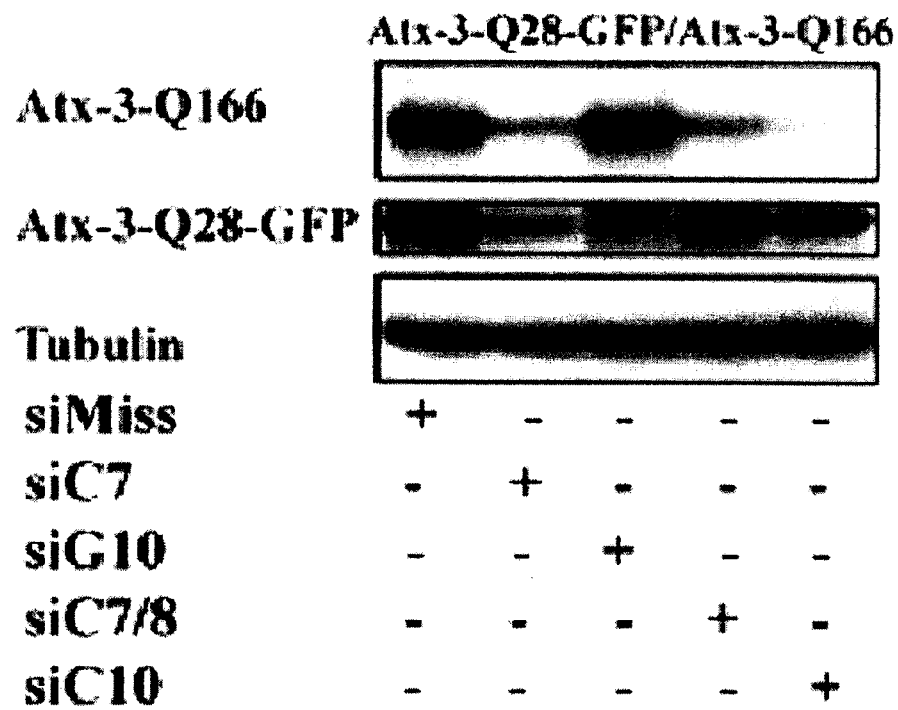

In the disease state, normal and mutant alleles are simultaneously expressed. In plants and worms, activation of RNAi against one transcript results in the spread of silencing signals to other targets due to RNA-dependent RNA polymerase (RDRP) activity primed by the introduced RNA (Fire 1998, Tang 2003). Although spreading has not been detected in mammalian cells and RDRP activity is not required for effective siRNA inhibition (Chiu 2002, Schwarz 2002, Martinez 2002), most studies have used cell-free systems in which a mammalian RDRP could have been inactivated. If triggering the mammalian RNAi pathway against one allele activates cellular mechanisms that also silence the other allele, then siRNA applications might be limited to non-essential genes. To test this possibility, the heterozygous state was simulated by co-transfecting Atx-3-Q28-GFP and Atx-3-Q166 and analyzing suppression by Western blot. As shown in FIG. 5e each siRNA retained the specificity observed in separate transfections: siC7 inhibited both alleles, siG10 inhibited only the wild type allele, and siC7/8 and siC10 inhibited only mutant allele expression.

Figure 5F:
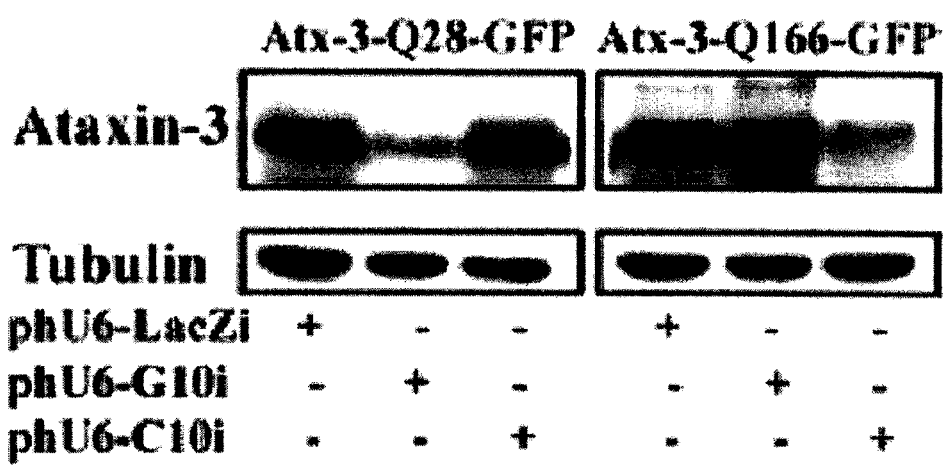

Effective siRNA therapy for late onset disease will likely require sustained intracellular expression of the siRNA. Accordingly, the present experiments were extended to two intracellular methods of siRNA production and delivery: expression plasmids and recombinant virus (Brummelkamp 2002, Xia 2002). Plasmids were constructed expressing siG10 or siC10 siRNA from the human U6 promoter as a hairpin transcript that is processed intracellularly to produce siRNA (Brummelkamp 2002, Xia 2002). When co-transfected with ataxin-3-GFP expression plasmids, phU6-G10i and phU6-C10i-siRNA plasmids specifically suppressed wild type or mutant ataxin-3 expression, respectively (FIG. 5f).

Figure 8A:
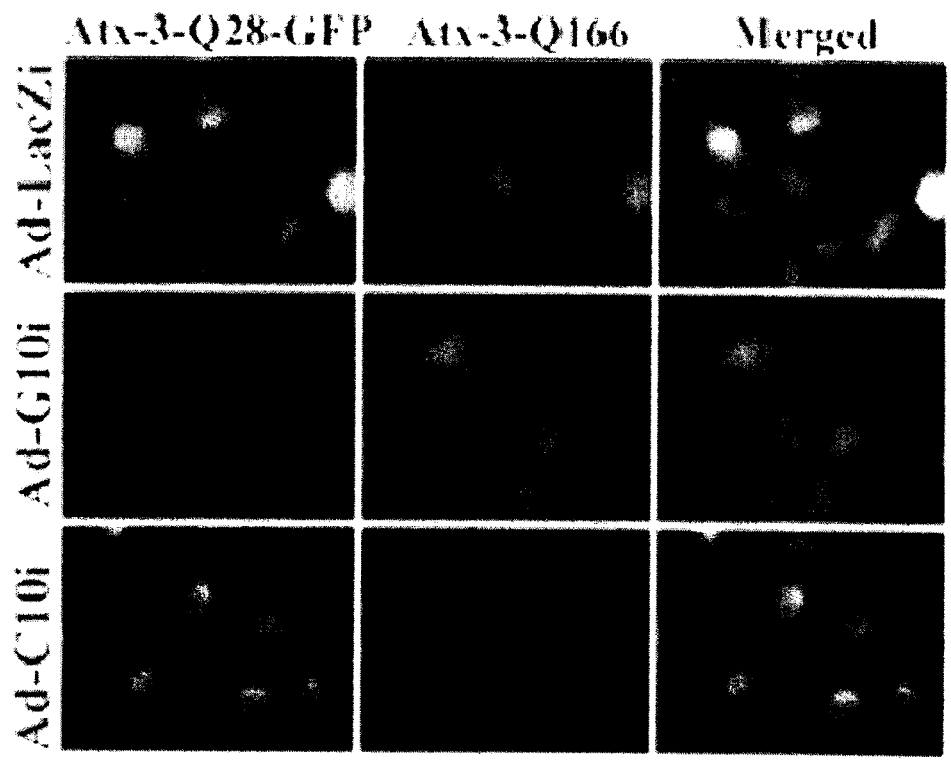
FIGS. 8A-8D. shRNA-expressing adenovirus mediates allele-specific silencing in transiently transfected Cos-7 cells simulating the heterozygous state. (A) Representative images of cells cotransfected to express wild type and mutant ataxin-3 and infected with the indicated adenovirus at 50 multiplicities of infection (MOI). Atx-3-Q28-GFP (green) is directly visualized and Atx-3-Q166 (red) is detected by immunofluorescence with 1C2 antibody. Nuclei visualized with DAPI stain in merged images. An average of 73.1% of cells co-expressed both ataxin-3 proteins with siMiss. (B) Quantitation of mean fluorescence from 2 independent experiments performed as in (A). (C) Western blot analysis of viral-mediated silencing in Cos-7 cells expressing wild type and mutant ataxin-3 as in (A). Mutant ataxin-3 detected with 1C2 antibody and wild-type human and endogenous primate ataxin-3 detected with anti-ataxin-3 antibody. (D) shRNA-expressing adenovirus mediates allele-specific silencing in stably transfected neural cell lines. Differentiated PC12 neural cells expressing wild type (left) or mutant (right) ataxin-3 were infected with adenovirus (100 MOI) engineered to express the indicated hairpin siRNA. Shown are Western blots immunostained for ataxin-3 and GAPDH as loading control.
Figure 8B:
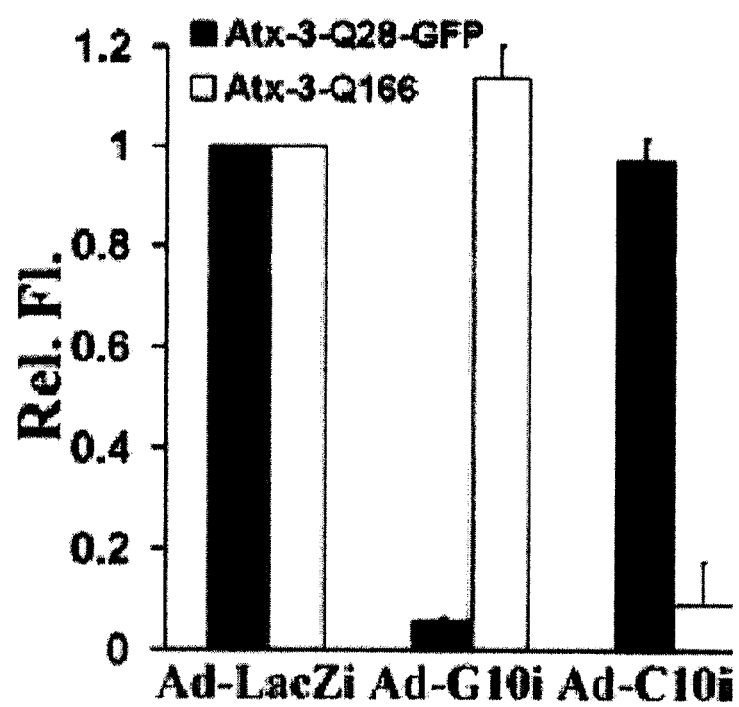
Figure 8C:
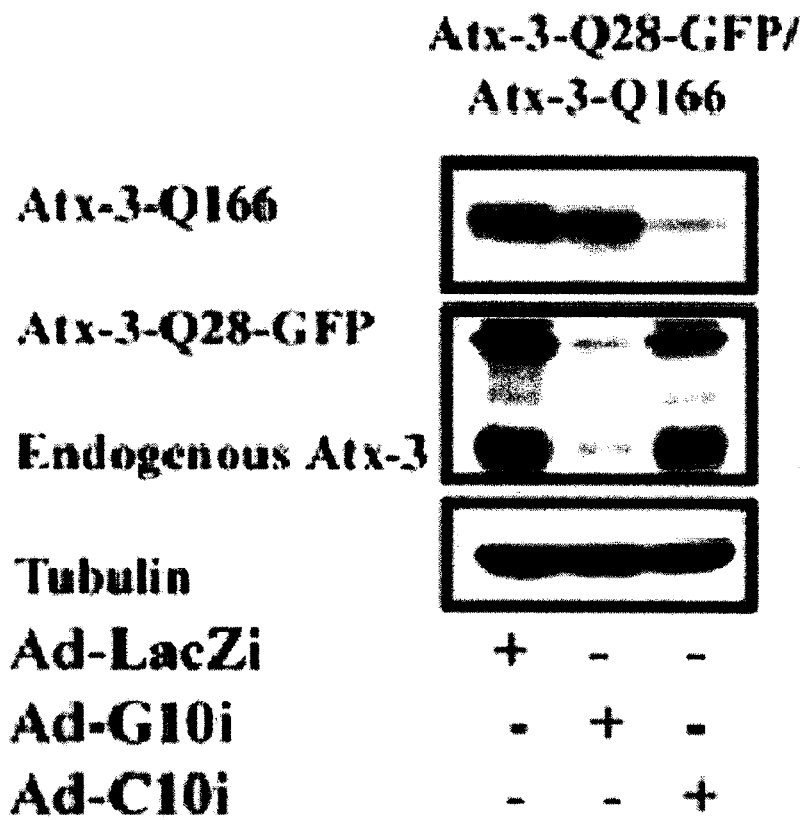

This result encouraged the inventors to engineer recombinant adenoviral vectors expressing allele-specific siRNA (Xia 2002). Viral-mediated suppression was tested in Cos-7 cells transiently transfected with both Atx-3-Q28-GFP and Atx-3-Q166 to simulate the heterozygous state. Cos-7 cells infected with adenovirus encoding siG10, siC10 or negative control siRNA (Ad-G10i, Ad-C10i, and Ad-LacZi respectively) exhibited allele-specific silencing of wild type ataxin-3 expression with Ad-G10i and of mutant ataxin-3 with Ad-C10i (FIG. 8a,b,c). Quantitation of fluorescence (FIG. 8b) showed that Ad-G10i reduced wild type ataxin-3 to 5.4% of control levels while mutant ataxin-3 expression remained unchanged. Conversely, Ad-C10i reduced mutant ataxin-3 fluorescence levels to 8.8% of control and retained 97.4% of wild type signal. These results were confirmed by Western blot where it was further observed that Ad-G10i virus decreased endogenous (primate) ataxin-3 while Ad-C10i did not (FIG. 8c).

Figure 8D:
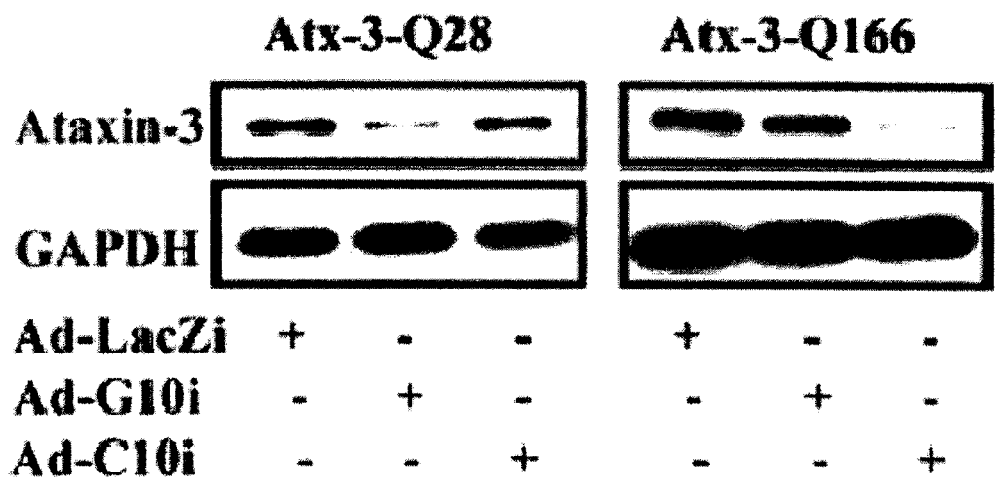

Viral mediated suppression was also assessed in differentiated PC12 neural cell lines that inducibly express normal (Q28) or expanded (Q166) mutant ataxin-3. Following infection with Ad-G10i, Ad-C10i, or Ad-LacZi, differentiated neural cells were placed in doxycycline for three days to induce maximal expression of ataxin-3. Western blot analysis of cell lysates confirmed that the Ad-G10i virus suppressed only wild type ataxin-3, Ad-C10i virus suppressed only mutant ataxin-3, and Ad-LacZi had no effect on either normal or mutant ataxin-3 expression (FIG. 8d). Thus, siRNA retains its efficacy and selectivity across different modes of production and delivery to achieve allele-specific silencing of ataxin-3.

Allele-Specific Silencing of a Missense Tau Mutation.

Figure 9A:
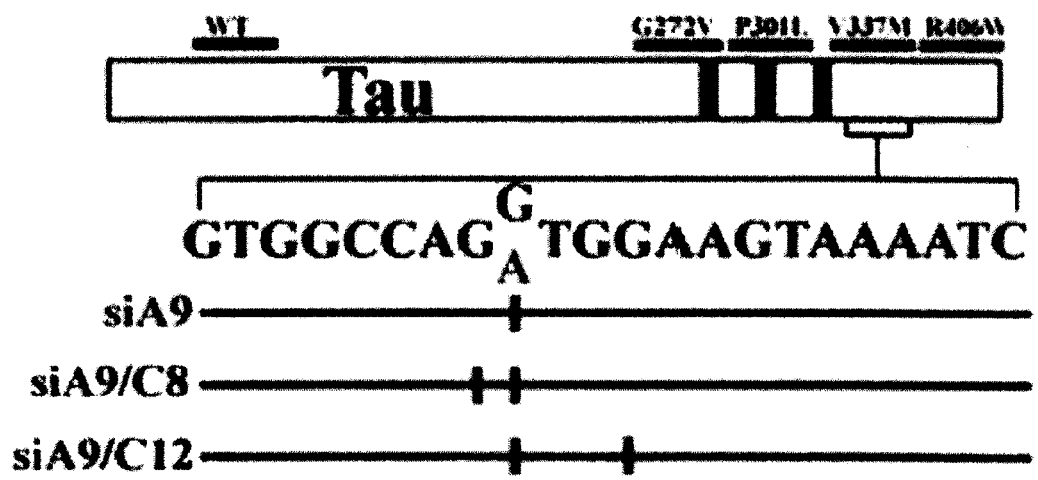
FIGS. 9A-C. Allele-specific siRNA suppression of a missense Tau mutation. (A) Schematic of human tau cDNA with bars indicating regions and mutations tested for siRNA suppression. Of these, the V337M region showed effective suppression and was further studied. Vertical bars represent microtubule binding repeat elements in Tau. In the displayed siRNAs, blue and red bars denote A and C respectively. In this Figure, GTGGCCAGATGGAAGTAAAATC is SEQ ID NO:35, and GTGGCCAGGTGGAAGTAAAATC is SEQ ID NO:41. (B) Western blot analysis of cells co-transfected with WT or V337M Tau-EGFP fusion proteins and the indicated siRNAs. Cells were lysed 24 hr after transfection and probed with anti-tau antibody. Tubulin immunostaining is shown as loading control. (C) Quantitation of fluorescence in Cos-7 cells transfected with wild type tau-EGFP or mutant V337M tau-EGFP expression plasmids and the indicated siRNAs. Bars depict mean fluorescence and SEM from three independent experiments. Fluorescence from cells co-transfected with siMiss was set at one.
Figure 9B:
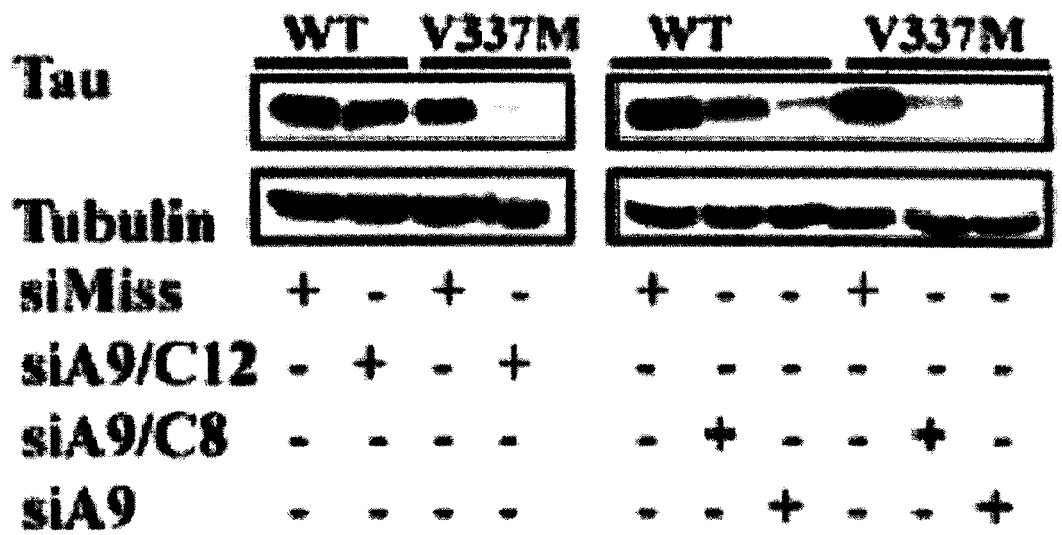
Figure 9C:
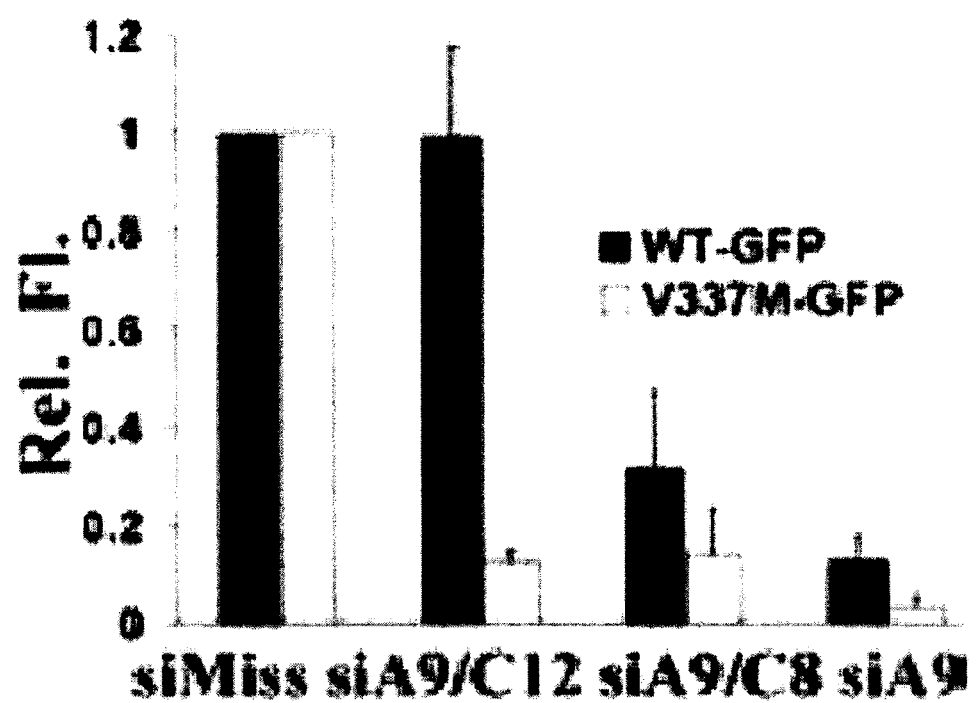

The preceding results indicate that, for DNA repeat mutations in which the repeat itself does not present an effective target, an associated SNP can be exploited to achieve allele-specific silencing. To test whether siRNA works equally well to silence disease-causing mutations directly, the inventors targeted missense Tau mutations that cause FTDP-17 (Poorkaj 1998, Hutton 1998). A series of 21-24 nt siRNAs were generated in vitro against four missense FTDP-17 mutations: G272V, P301L, V337M, and R406W (FIG. 6 and FIG. 9a). In each case the point mutation was placed centrally, near the likely cleavage site in the RISC complex (position 9, 10 or 11) (Laccone 1999). A fifth siRNA designed to target a 5' sequence in all Tau transcripts was also tested. To screen for siRNA-mediated suppression, the inventors co-transfected GFP fusions of mutant and wild type Tau isoforms together with siRNA into Cos-7 cells. Of the five targeted sites, the inventors obtained robust suppression with siRNA corresponding to V337M (FIG. 6 and FIG. 9A) (Poorkaj 1998, Hutton 1998), and thus focused further analysis on this mutation. The V337M mutation is a G to A base change in the first position of the codon (GTG to ATG), and the corresponding V337M siRNA contains the A missense change at position 9 (siA9). This intended V337M-specific siRNA preferentially silenced the mutant allele but also caused significant suppression of wild type Tau (FIG. 9b,c).

Figure 10A:
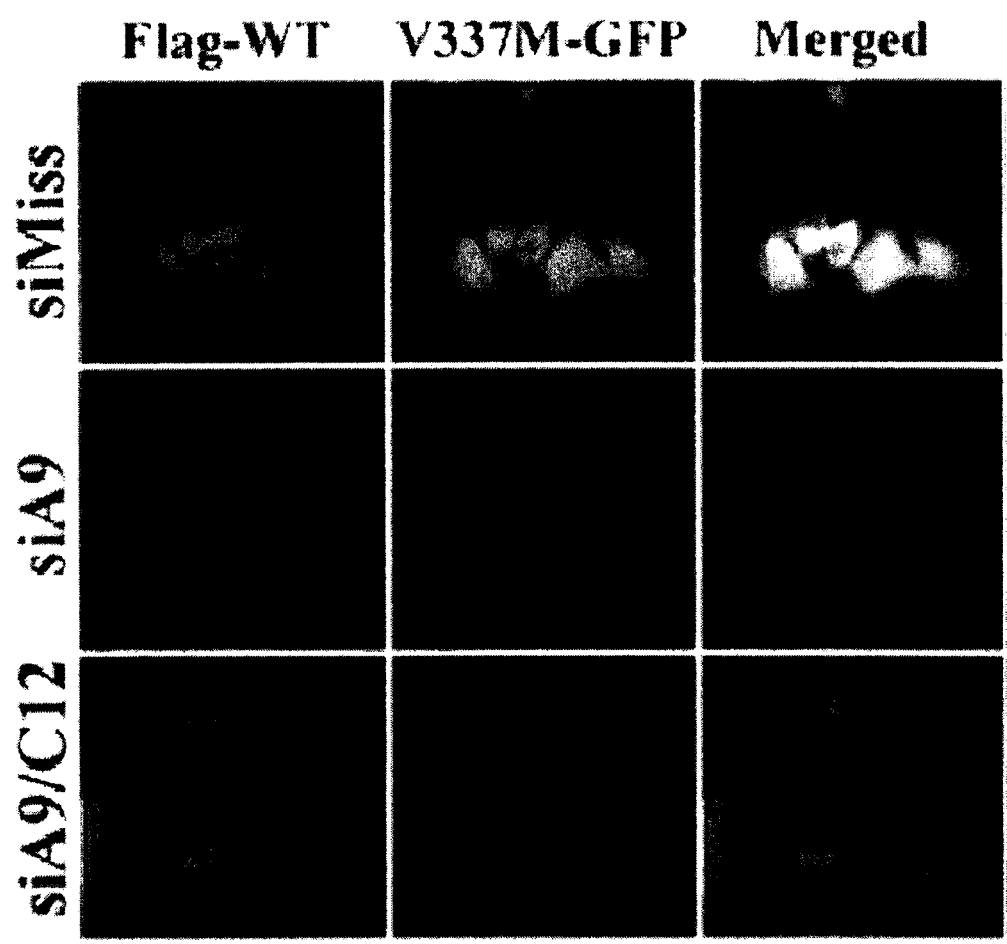
FIGS. 10A-10C. Allele-specific silencing of Tau in cells simulating the heterozygous state. (A) Representative fluorescent images of fixed Hela cells co-transfected with flag-tagged WT-Tau (red), V337M-Tau-GFP (green), and the indicated siRNAs. An average of 73.7% of cells co-expressed both Tau proteins with siMiss. While siA9 suppresses both alleles, siA9/C12 selectively decreased expression of mutant Tau only. Nuclei visualized with DAPI stain in merged images. (B) Quantitation of mean fluorescence from 2 independent experiments performed as in (A). (C) Western blot analysis of cells co-transfected with Flag-WT-Tau and V337M-Tau-EGFP fusion proteins and the indicated siRNAs. Cells were lysed 24 hr after transfection and probed with anti-tau antibody. V337M-GFP Tau was differentiated based on reduced electrophoretic mobility due to the addition of GFP. Tubulin immunostaining is shown as a loading control.
Figure 10B:
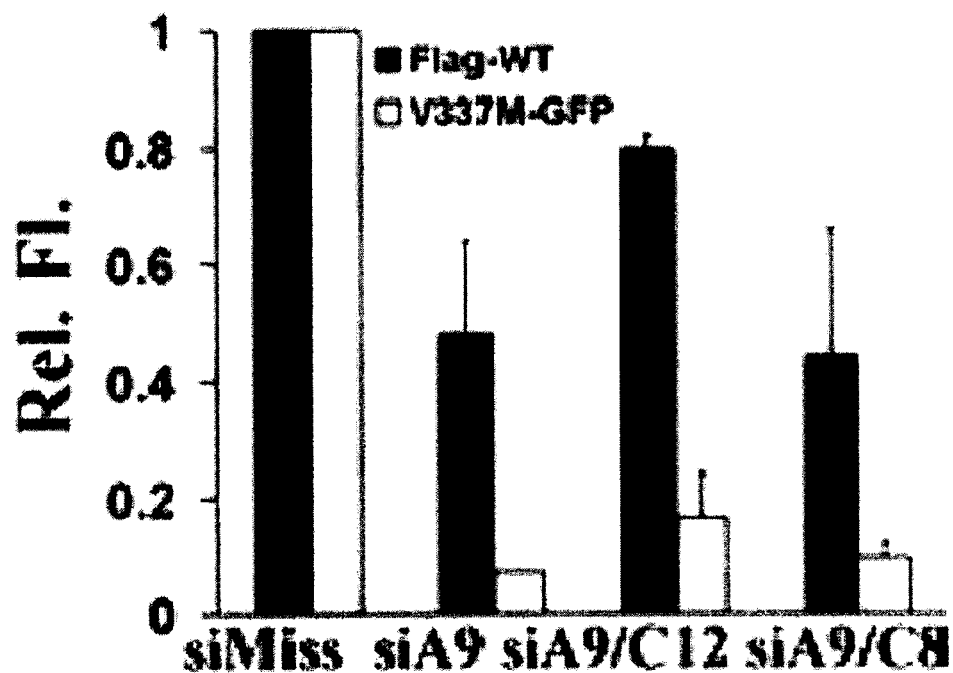
Figure 10C:
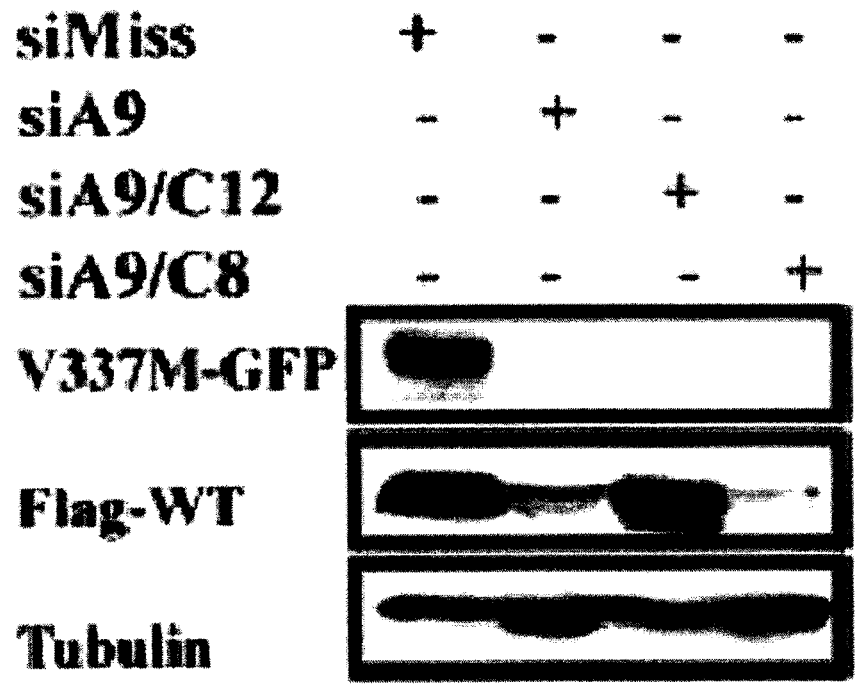

Based on the success of this approach with ataxin-3, the inventors designed two additional siRNAs that contained the V337M (G to A) mutation at position 9 as well as a second introduced G-C mismatch immediately 5' to the mutation (siA9/C8) or three nucleotides 3' to the mutation (siA9/C12), such that the siRNA now contained two mismatches to the wild type but only one to the mutant allele. This strategy resulted in further preferential inactivation of the mutant allele. One siRNA, siA9/C12, showed strong selectivity for the mutant tau allele, reducing fluorescence to 12.7% of control levels without detectable loss of wild type Tau (FIG. 9b,c). Next, we simulated the heterozygous state by co-transfecting V337M-GFP and flag-tagged WT-Tau expression plasmids (FIG. 10). In co-transfected HeLa cells, siA9/C12 silenced the mutant allele (16.7% of control levels) with minimal alteration of wild type expression assessed by fluorescence (FIG. 10a) and Western blot (FIG. 10b). In addition, siA9 and siA9/C8 displayed better allele discrimination than we had observed in separate transfections, but continued to suppress both wild type and mutant tau expression (FIG. 10a,b,c).

Discussion

Despite the rapidly growing siRNA literature, questions remain concerning the design and application of siRNA both as a research tool and a therapeutic strategy. The present study, demonstrating allele-specific silencing of dominant disease genes, sheds light on important aspects of both applications.

Because many disease genes encode essential proteins, development of strategies to exclusively inactivate mutant alleles is important for the general application of siRNA to dominant diseases. The present results for two unrelated disease genes demonstrate that in mammalian cells it is possible to silence a single disease allele without activating pathways analogous to those found in plants and worms that result in the spread of silencing signals (Fire 1998, Tang 2003).

In summary, siRNA can be engineered to silence expression of disease alleles differing from wild type alleles by as little as a single nucleotide. This approach can directly target missense mutations, as in frontotemporal dementia, or associated SNPs, as in MJD/SCA3. The present stepwise strategy for optimizing allele-specific targeting extends the utility of siRNA to a wide range of dominant diseases in which the disease gene normally plays an important or essential role. One such example is the polyglutamine disease, Huntington disease (HD), in which normal HD protein levels are developmentally essential (Nasir 1995). The availability of mouse models for many dominant disorders, including MJD/SCA3 (Cemal 2002), HD (Lin 2001), and FTDP-17 (Tanemura 2002), allows for the in vivo testing of siRNA-based therapy for these and other human diseases.

Example 3

Therapy for DYT1 Dystonia: Allele-Specific Silencing of Mutant TorsinA

DYT1 dystonia is the most common cause of primary generalized dystonia. A dominantly inherited disorder, DYT1 usually presents in childhood as focal dystonia and progresses to severe generalized disease. With one possible exception, all cases of DYT1 result from a common GAG deletion in TOR1A, eliminating one of two adjacent glutamic acids near the C-terminus of the protein TorsinA (TA). Although the precise cellular function of TA is unknown, it seems clear that mutant TA (TAmut) acts through a dominant-negative or dominant-toxic mechanism. The dominant nature of the genetic defect in DYT1 dystonia suggests that efforts to silence expression of TAmut should have potential therapeutic benefit.

Several characteristics of DYT1 make it an ideal disease in which to explore siRNA-mediated gene silencing as potential therapy. Of greatest importance, the dominant nature of the disease suggests that a reduction in mutant TA, whatever the precise pathogenic mechanism proves to be, will be helpful. Moreover, the existence of a single common mutation that deletes a full three nucleotides suggests it may be feasible to design siRNA that will specifically target the mutant allele and will be applicable to all affected persons. Finally, there is no effective therapy for DYT1, a relentless and disabling disease. Thus, any therapeutic approach with promise needs to be explored. Because TAwt may be an essential protein, however, it is critically important that efforts be made to silence only the mutant allele.

In the studies reported here, the inventors explored the utility of siRNA for DYT1. As outlined in the strategy in FIG. 11, the inventors sought to develop siRNA that would specifically eliminate production of protein from the mutant allele. By exploiting the three base pair difference between wild type and mutant alleles, the inventors successfully silenced expression of TAmut without interfering with expression of the wild type protein (TAwt).

Methods siRNA Design and Synthesis

Small-interfering RNA duplexes were synthesized in vitro according to a previously described protocol (Donze 2002), using AmpliScribeT7 High Yield Transcription Kit (Epicentre Technologies) and desalted DNA oligonucleotides (IDT). siRNAs were designed to target different regions of human TA transcript: 1) an upstream sequence common to both TAwt and TAmut (com-siRNA); 2) the area corresponding to the mutation with either the wild type sequence (wt-siRNA) or the mutant sequence positioned at three different places (mutA-siRNA, mutB-siRNA, mutC-siRNA); and 3) a negative control siRNA containing an irrelevant sequence that does not target any region of TA (mis-siRNA). The design of the primers and targeted sequences are shown schematically in FIG. 12. After in vitro synthesis, the double stranded structure of the resultant RNA was confirmed in 1.5 agarose gels and RNA concentration determined with a SmartSpect 3000 UV Spectrophotometer (BioRad).

Plasmids pcDNA3 containing TAwt or TAmut cDNA were kindly provided by Xandra Breakefield (Mass General Hospital, Boston, Mass.). This construct was produced by cloning the entire coding sequences of human TorsinA (1-332), both wild-type and mutant (GAG deleted), into the mammalian expression vector, pcDNA3 (Clontech, Palo Alto, Calif.). Using PCR based strategies, an N-terminal hemagglutinin (HA) epitope tag was inserted into both constructs. pEGFP-C3-TAwt was kindly provided by Pullanipally Shashidharan (Mt Sinai Medical School, NY). This construct was made by inserting the full-length coding sequence of wild-type TorsinA into the EcoRI and BamHI restriction sites of the vector pEGFP-C3 (Clontech). This resulted in a fusion protein including eGFP, three "stuffer" amino acids and the 331 amino acids of TorsinA. HA-tagged TAmut was inserted into the ApaI and SalI restriction sites of pEGFP-C1 vector (Clontech), resulting in a GFP-HA-TAmut construct.

Cell Culture and Transfections

Methods for cell culture of Cos-7 have been described previously (Chai 1999b). Transfections with DNA plasmids and siRNA were performed using Lipofectamine Plus (LifeTechnologies) according to the manufacturer's instructions in six or 12 well plates with cells at 70-90% confluence. For single plasmid transfection, 1 μg of plasmid was transfected with 5 μg of siRNA. For double plasmid transfection, 0.75 μg of each plasmid was transfected with 3.75 fig of siRNA.

Western Blotting and Fluorescence Microscopy.

Cells were harvested 36 to 48 hours after transfection and lysates were assessed for TA expression by Western Blot analysis (WB) as previously described (Chai 1999b). The antibody used to detect TA was polyclonal rabbit antiserum generated against a TA-maltose binding protein fusion protein (kindly provided by Xandra Breakefield) at a 1:500 dilution. Additional antibodies used in the experiments described here are the anti-HA mouse monoclonal antibody 12CA5 (Roche) at 1:1,000 dilution, monoclonal mouse anti-GFP antibody (MBL) at 1:1,000 dilution, and for loading controls, anti α-tubulin mouse monoclonal antibody (Sigma) at 1:20,000 dilution.

Fluorescence visualization of fixed cells expressing GFP-tagged TA was performed with a Zeiss Axioplan fluorescence microscope. Nuclei were visualized by staining with 5 μg/ml DAPI at room temperature for 10 minutes. Digital images were collected on separate red, green and blue fluorescence channels using a Diagnostics SPOT digital camera. Live cell images were collected with a Kodak MDS 290 digital camera mounted on an Olympus CK40 inverted microscope equipped for GFP fluorescence and phase contrast microscopy. Digitized images were assembled using Adobe Photoshop 6.0.

Western Blot and Fluorescence Quantification.

For quantification of WB signal, blots were scanned with a Hewlett Packard ScanJet 5100C scanner. The pixel count and intensity of bands corresponding to TA and α-tubulin were measured and the background signal subtracted using Scion Image software (Scion Corporation). Using the α-tubulin signal from control lanes as an internal reference, the TA signals were normalized based on the amount of protein loaded per lane and the result was expressed as percentage of TA signal in the control lane. Fluorescence quantification was determined by collecting three non-overlapping images per well at low power (10×), and assessing the pixel count and intensity for each image with Bioquant Nova Prime software (BIOQUANT Image Analysis Corporation). Background fluorescence, which was subtracted from experimental images, was determined by quantification of fluorescence images of untransfected cells at equivalent confluence, taken under identical illumination and exposure settings.

Results

Expression of Tagged TorsinA Constructs.

To test whether allele-specific silencing could be applied to DYT1, a way to differentiate TAwt and TAmut proteins needed to be developed. Because TAwt and TAmut display identical mobility on gels and no isoform-specific antibodies are available, amino-terminal epitope-tagged TA constructs and GFP-TA fusion proteins were generated that would allow distinguishingTAwt and TAmut. The use of GFP-TA fusion proteins also facilitated the ability to screen siRNA suppression because it allowed visualization of TA levels in living cells over time.

In transfected Cos-7 cells, epitope-tagged TA and GFP-TA fusion protein expression was confirmed by using the appropriate anti-epitope and anti-TA antibodies. Fluorescence microscopy in living cells showed that GFP-TAwt and GFP-TAmut fusion proteins were expressed diffusely in the cell, primarily in the cytoplasm, although perinuclear inclusions were also seen. It is important to note that these construct were designed to express reporter proteins in order to assess allele-specific RNA interference rather than to study TA function. The N-terminal epitope and GFP domains likely disrupt the normal signal peptide-mediated translocation of TA into the lumen of the endoplasmic reticulum, where TA is thought to function. Thus, while these constructs facilitated expression analysis in the studies described here, they are of limited utility for studying TA function.

Silencing TorsinA with siRNA.

Figure 12:
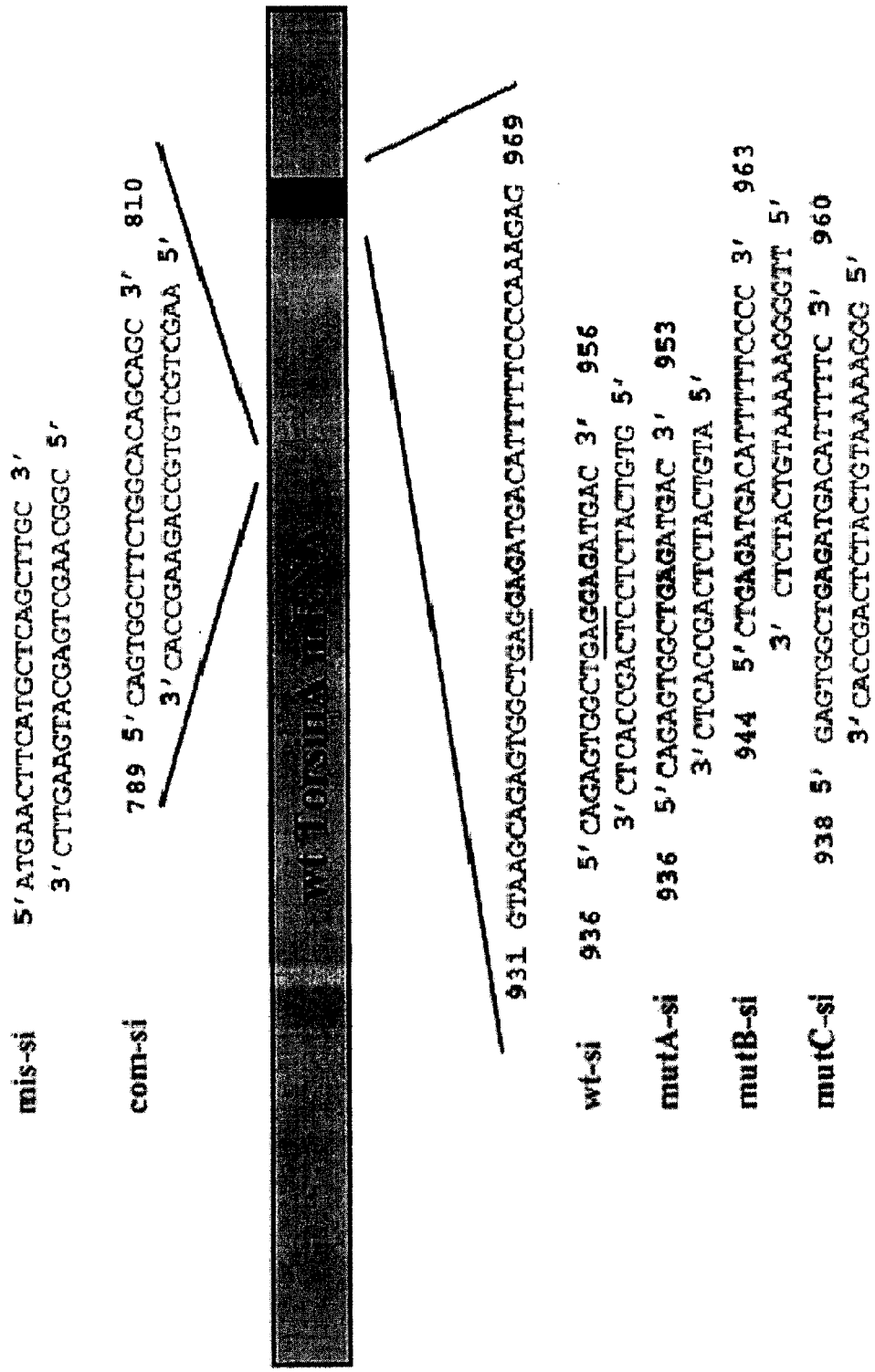
FIG. 12. Design and targeted sequences of siRNAs. Shown are the relative positions and targeted mRNA sequences for each primer used in this study. Mis-siRNA (negative control; SEQ ID NOs:42-43) does not target TA; com-siRNA (SEQ ID NOs:44-45) targets a sequence present in wild type and mutant TA; wt-siRNA (SEQ ID NOs:47-48) targets only wild type TA; and three mutant-specific siRNAs (Mut A (SEQ ID NOs:49-50), B (SEQ ID NOs:51-52), C (SEQ ID NOs:53-54)) preferentially target mutant TA. The pair of GAG codons near the c-terminus of wild type mRNA (SEQ ID NO:46) are shown in underlined gray and black, with one codon deleted in mutant mRNA.
Figure 13A:
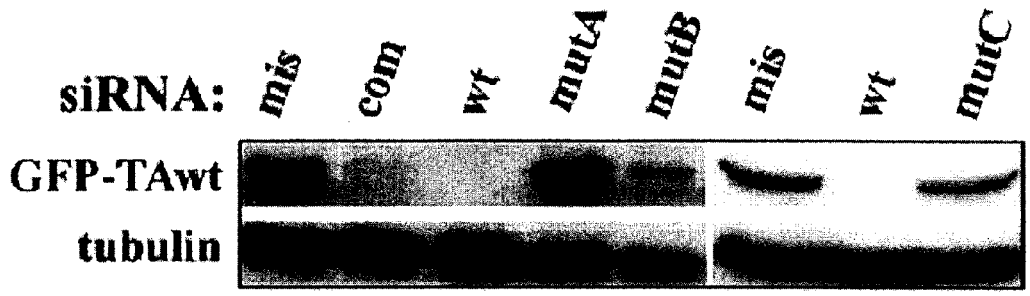
FIGS. 13A-13E. siRNA silencing of TAwt and TAmut in Cos-7 cells. (A) Western blot results showing the effect of different siRNAs on GFP-TAwt expression levels. Robust suppression is achieved with wt-siRNA and com-siRNA, while the mutant-specific siRNAs MutA, (B) and (C) have modest or no effect on GFP-TAwt expression. Tubulin loading controls are also shown. (B) Similar experiments with cells expressing HA-TAmut, showing significant suppression by mutant-specific siRNAs and com-siRNA but no suppression by the wild type-specific siRNA, wt-siRNA. (C) Quantification of results from at least three separate experiments as in A and B. (D) Cos-7 cells transfected with GFP-TAwt or GFP-TAmut and different siRNAs visualized under fluorescence microscopy (200×). Representative fields are shown indicating allele-specific suppression. (E) Quantification of fluorescence signal from two different experiments as in D.
Figure 13B:
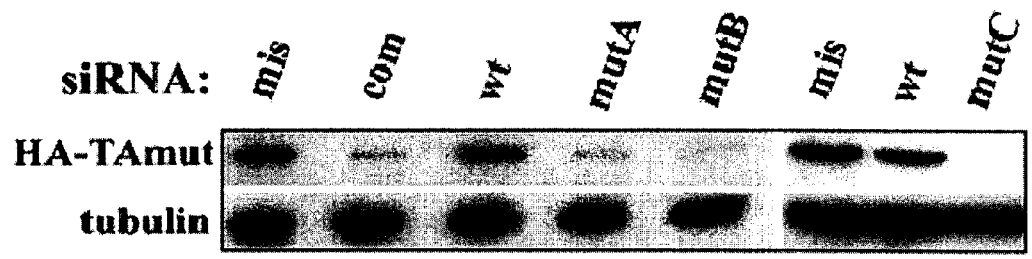
Figure 13C:
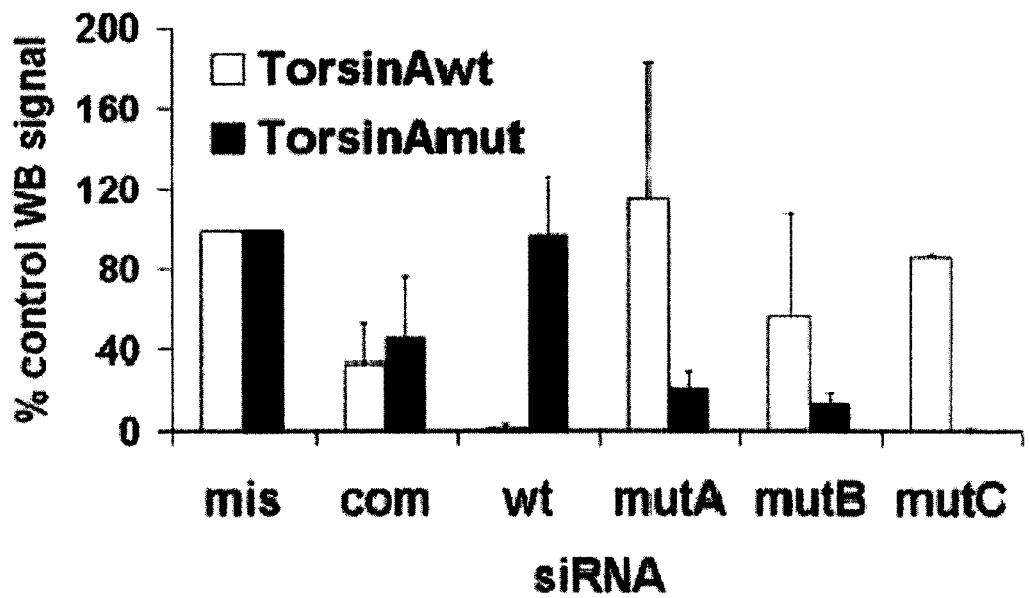
Figure 13D:
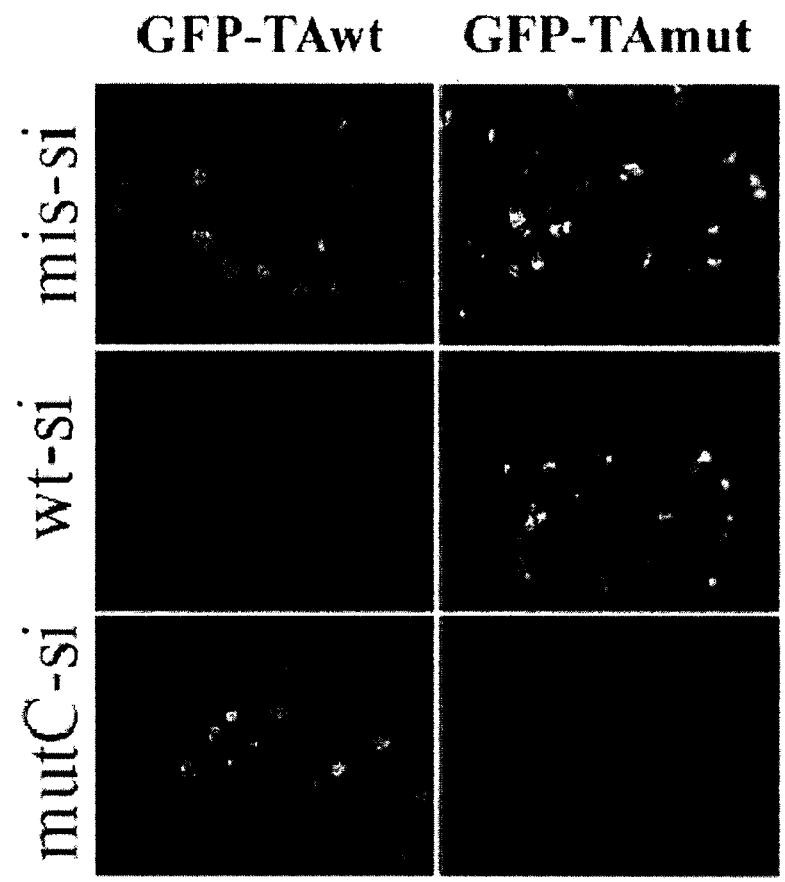
Figure 13E:
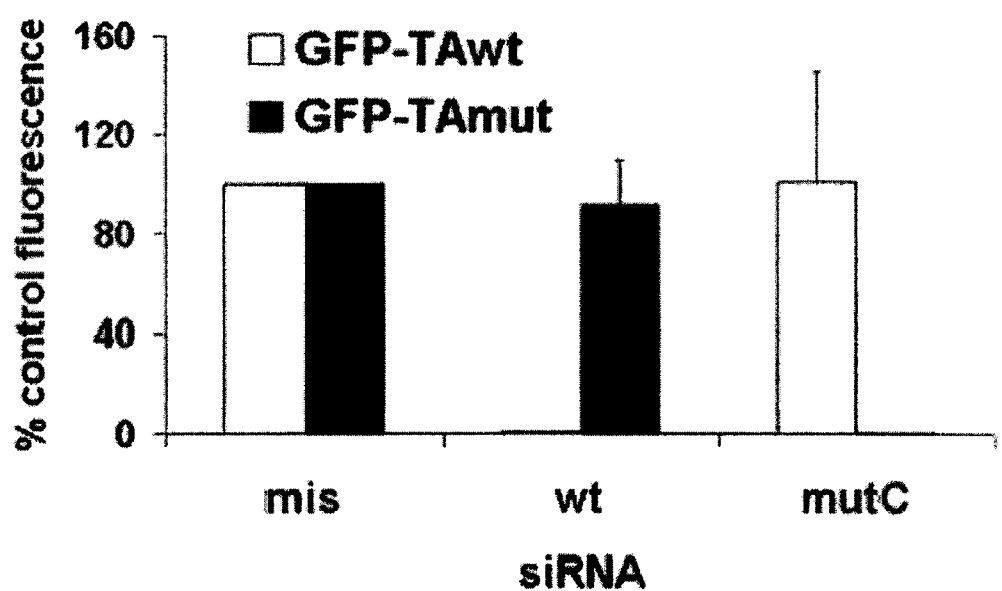

Various siRNAs were designed to test the hypothesis that siRNA-mediated suppression of TA expression could be achieved in an allele-specific manner (FIG. 12). Because siRNA can display exquisite sequence specificity, the three base pair difference between mutant and wild type TOR1A alleles might be sufficient to permit the design of siRNA that preferentially recognizes mRNA derived from the mutant allele. Two siRNAs were initially designed to target TAmut (mutA-siRNA and mutB-siRNA) and one to target TAwt (wt-siRNA). In addition, a positive control siRNA was designed to silence both alleles (com-siRNA) and a negative control siRNA of irrelevant sequence (mis-siRNA) was designed. Cos-7 cells were first cotransfected with siRNA and plasmids encoding either GFP-TAwt or untagged TAwt at a siRNA to plasmid ratio of 5:1. With wt-siRNA, potent silencing of TAwt expression was observed to less than 1% of control levels, based on western blot analysis of cell lysates (FIGS. 13A and 13C). With com-siRNA, TAwt expression was suppressed to ~30% of control levels. In contrast, mutA-siRNA did not suppress TAwt and mutB-siRNA suppressed TAwt expression only modestly. These results demonstrate robust suppression of TAwt expression by wild type-specific siRNA but not mutant-specific siRNA.

To assess suppression of TAmut, the same siRNAs were cotransfected with plasmids encoding untagged or HA-tagged TAmut. With mutA-siRNA or mutB-siRNA, marked, though somewhat variable, suppression of TAmut expression was observed as assessed by western blot analysis of protein levels (FIGS. 13B and 13C). With com-siRNA, suppression of TAmut expression was observed similar to what was observed with TAwt expression. In contrast, wt-siRNA did not suppress expression of TAmut. Thus differential suppression of TAmut expression was observed by allele-specific siRNA in precisely the manner anticipated by the inventors.

To achieve even more robust silencing of TAmut, a third siRNA was engineered to target TAmut (mutC-siRNA, FIG. 12). MutC-siRNA places the GAG deletion more centrally in the siRNA duplex. Because the central portion of the antisense strand of siRNA guides mRNA cleavage, it was reasoned that placing the GAG deletion more centrally might enhance specific suppression of TAmut. As shown in FIG. 13, mutC-siRNA suppressed TAmut expression more specifically and robustly than the other mut-siRNAs tested. In transfected cells, mutC-siRNA suppressed TAmut to less than 0.5% of control levels, and had no effect on the expression of TAwt.

To confirm allele-specific suppression by wt-siRNA and mutC-siRNA, respectively, the inventors cotransfected cells with GFP-TAwt or GFP-TAmut together with mis-siRNA, wt-siRNA or mutC-siRNA. Levels of TA expression were assessed 24 and 48 hours later by GFP fluorescence, and quantified the fluorescence signal from multiple images was quantified. The results (FIGS. 13D and 13E) confirmed the earlier western blots results in showing potent, specific silencing of TAwt and TAmut by wt-siRNA and mutC-siRNA, respectively, in cultured mammalian cells.

Allele-Specific Silencing in Simulated Heterozygous State.

Figure 14A:
FIGS. 14A-14B. Allele-specific silencing by siRNA in the simulated heterozygous state. Cos-7 cells were cotransfected with plasmids encoding differentially tagged TAwt and TAmut, together with the indicated siRNA. (A) Western blot results analysis showing selective suppression of the targeted allele by wt-siRNA or mutC-siRNA. (B) Quantification of results from three experiments as in (A).
Figure 14B:
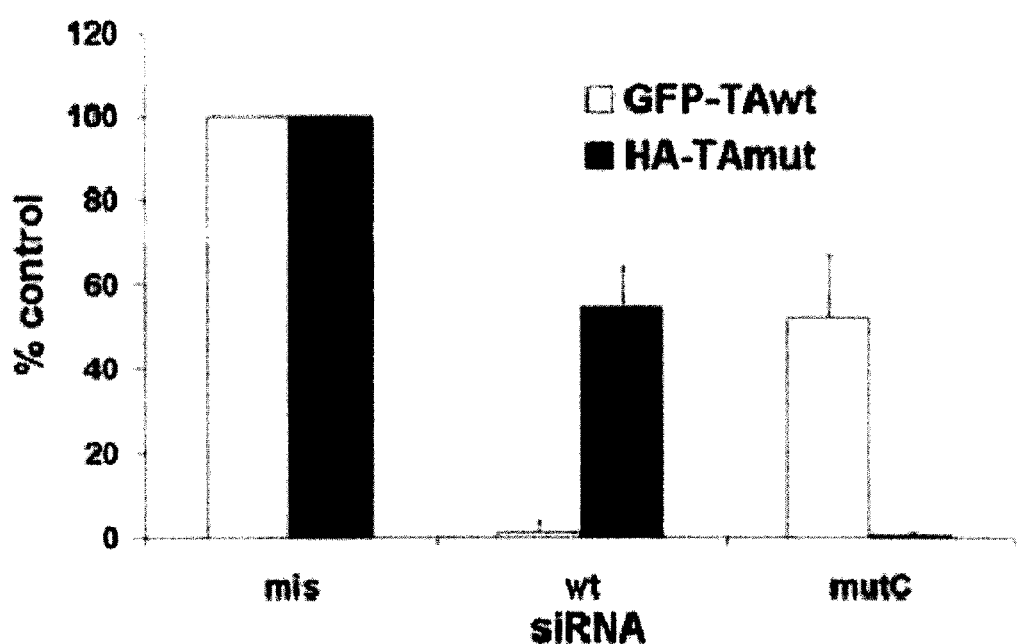

In DYT1, both the mutant and wild type alleles are expressed. Once the efficacy of siRNA silencing was established, the inventors sought to confirm siRNA specificity for the targeted allele in cells that mimic the heterozygous state of DYT1. In plants and *Caenorhabditis elegans*, RNA-dependent RNA polymerase activity primed by introduction of exogenous RNA can result in the spread of silencing signals along the entire length of the targeted mRNA (Fire 1998, Tang 2003). No evidence for such a mechanism has been discovered in mammalian cells (Schwarz 2002, Chiu 2002). Nonetheless it remained possible that silencing of the mutant allele might activate cellular processes that would also inhibit expression from the wild type allele. To address this possibility, Cos-7 cells were cotransfected with both GFP-TAwt and HA-TAmut, and suppression by mis-siRNA, wt-siRNA or mutC-siRNA was assessed. As shown in FIG. 14, potent and specific silencing of the targeted allele (either TAmut or TAwt) to levels less than 1% of controls was observed, with only slight suppression in the levels of the non-targeted protein. Thus, in cells expressing mutant and wild type forms of the protein, siRNA can suppress TAmut while sparing expression of TAwt.

Discussion

In this study the inventors succeeded in generating siRNA that specifically and robustly suppresses mutant TA, the defective protein responsible for the most common form of primary generalized dystonia. The results have several implications for the treatment of DYT1 dystonia. First and foremost, the suppression achieved was remarkably allele-specific, even in cells simulating the heterozygous state. In other words, efficient suppression of mutant TA occurred without significant reduction in wild type TA. Homozygous TA knockout mice die shortly after birth, while the heterozygous mice are normal (Goodchild 2002), suggesting an essential function for TA. Thus, therapy for DYT1 needs to eliminate the dominant negative or dominant toxic properties of the mutant protein while sustaining expression of the normal allele in order to prevent the deleterious consequences of loss of TA function. Selective siRNA-mediated suppression of the mutant allele fulfills these criteria without requiring detailed knowledge of the pathogenic mechanism.

An appealing feature of the present siRNA therapy is applicable to all individuals afflicted with DYT1. Except for one unusual case (Leung 2001, Doheny 2002, Klein 2002b), all persons with DYT1 have the same (GAG) deletion mutation (Ozelius 1997, Ozelius 1999). This obviates the need to design individually tailored siRNAs. In addition, the fact that the DYT1 mutation results in a full three base pair difference from the wild type allele suggests that siRNA easily distinguishes mRNA derived from normal and mutant TOR1A alleles.

It is important to recognize that DYT1 is not a fully penetrant disease (Fahn 1998, Klein 2002a). Even when expressed maximally, mutant TA causes significant neurological dysfunction less than 50% of the time. Thus, even partial reduction of mutant TA levels might be sufficient to lower its pathological brain activity below a clinically detectable threshold. In addition, the DYT1 mutation almost always manifests before age 25, suggesting that TAmut expression during a critical developmental window is required for symptom onset. This raises the possibility that suppressing TAmut expression during development might be sufficient to prevent symptoms throughout life. Finally, unlike many other inherited movement disorders DYT1 is not characterized by progressive neurodegeneration. The clinical phenotype must result primarily from neuronal dysfunction rather than neuronal cell death (Hornykiewicz 1986, Walker 2002, Augood 2002, Augood 1999). This suggests the potential reversibility of DYT1 by suppressing TAmut expression in overtly symptomatic persons.

Example 4 siRNA Specific for Huntington's Disease

The present inventors have developed huntingtin siRNA focused on two targets. One is non-allele specific (siH-Dexon2), the other is targeted to the exon 58 codon deletion, the only known common intragenic polymorphism in linkage dysequilibirum with the disease mutation (Ambrose et al, 1994). Specifically, 92% of wild type huntingtin alleles have four GAGs in exon 58, while 38% of HD patients have 3 GAGs in exon 58. To assess a siRNA targeted to the intragenic polymorphism, PC6-3 cells were transfected with a full-length huntingtin containing the exon 58 deletion. Specifically, PC6-3 rat pheochromocytoma cells were co-transfected with CMV-human Htt (37Qs) and U6 siRNA hairpin plasmids. Cell extracts were harvested 24 hours later and western blots were performed using 15 μg total protein extract. Primary antibody was an anti-huntingtin monoclonal antibody (MAB2166, Chemicon) that reacts with human, monkey, rat and mouse Htt proteins.

As seen in FIG. 15, the siRNA lead to silencing of the disease allele. As a positive control, a non-allele specific siRNA targeted to exon 2 of the huntingtin gene was used. siRNA directed against GFP was used as a negative control. Note that only siEx58#2 is functional.

Example 5

Targeting Alzheimer's Disease Genes with RNA Interference

Introduction

RNA interference (RNAi) plays an important role in diverse aspects of biology (McManus et al., 2002). Techniques that exploit the power of RNAi to suppress target genes have already become indispensable tools in research and are therapeutically useful (McManus et al., 2002; Song et al., 2003). In particular, the production of small interfering RNAs (siRNAs) that silence specific disease-related genes have wide-ranging therapeutic applications.

One promising therapeutic role for siRNA is the silencing of genes that cause dominantly inherited disease. The present inventors and others recently established the feasibility of this approach, and demonstrated that it is possible to engineer siRNAs that selectively silence mutant alleles while retaining expression of normal alleles (Miller et al., 2003; Gonzalez-Alegre et al., 2003; Ding et al., 2003; Abdelgany et al., 2003; Martinez et al. 2002a). Such allele-specific suppression is important for disorders in which the defective gene normally plays an important or essential role.

Generating effective siRNAs for target genes is not always straightforward, however, particularly when designing siRNAs that selectively target mutant alleles (Miller et al. 2003; Ding et al. 2003). Here the present inventors describe a simple, novel approach for producing siRNAs that should facilitate the development of gene and allele-specific siRNAs. Using this strategy, the inventors then created allele-specific siRNA for mutations in two important neurodegenerative disease genes, the genes encoding amyloid precursor protein (APP) and tau.

Recently the inventors demonstrated allele-specific silencing for tau and two other dominant neurogenetic disease genes (see examples above; Miller et al., 2003; Gonzalez-Alegre et al., 2003). But due to constraints imposed by the method of siRNA production, the inventors could not systematically analyze the effect of positioning mutations at each point along the antisense guide strand that mediates siRNA silencing. Here, the inventors have developed an efficient strategy to produce and screen siRNAs. Using this approach with APP and tau as model target genes, the inventors demonstrate that allele specificity of siRNA targeting is optimal when mutations are placed centrally within the 21-nucleotide siRNA.

Materials and Methods:

siRNA Synthesis.

In vitro synthesis of siRNA was done using a previously described protocol (Miller et al., 2003; Donze et al., 2002). Desalted DNA oligonucleotides (Integrated DNA Technologies, Coralville, Iowa) encoding sense and antisense target sequences were used with the AmpliScribeT7 high-yield transcription kit (Epicentre Technologies, Madison, Wis.) to generate siRNA duplexes (FIG. 16). After measuring reaction yields through absorbance at 260 nm, double-stranded nature was confirmed by agarose gel (1% wt/vol) electrophoresis and ethidium bromide staining. Note that for all siRNAs used in this study the most 5' nucleotide in the targeted cDNA sequence is referred to as position 1 and each subsequent nucleotide is numbered in ascending order from 5' to 3'.

Plasmids.

The plasmid used for GFP expression was pEGFP-C1 (BD Biosciences Clontech, Palo Alto, Calif.). Gloria Lee (University of Iowa, Iowa City, Iowa) kindly provided the constructs encoding human flag-tagged tau and V337M-GFP tau (Miller et al., 2003). Constructs encoding APP and APPsw mutant proteins were kindly provided by R. Scott Turner (University of Michigan, Ann Arbor, Mich.).

shRNA Plasmid Construction.

The tRNA-valine vector was constructed by annealing two primers, (forward 5'-CAGGACTAGTCTTTTAGGT-CAAAAAGAAGAAGCTTTGTAACCGTTGGTTTCCG-TAGTGTA-3' (SEQ ID NO:56) and reverse 5'-CTTC-GAACCGGGGACCTTTCGCGTGTTAGGCGA-ACGTGATAACCACTACACTACGGAAACCAAC-3' (SEQ ID NO:57)), extending the primers with PCR, and cloning them into pCR 2.1-TOPO vector using the TOPO TA Cloning Kit (Invitrogen Life Technologies, Carlsbad, Calif.) (Koseki et al., 1999; Kawasaki et al., 2003). Head-to-head 21 bp shRNA fragments were PCR amplified using as a template the resulting tRNA-valine vector, the forward primer above, and the reverse primers below. Each shRNA fragment was subsequently cloned into pCR 2.1-TOPO vector. Reverse primers used for generation of tRNA-valine driven shRNA are as follows:

tau:
tvTau:
(SEQ ID NO: 58)
AAAAAAGTGGCCAGGTGGAAGTAAAATCCAAGCTTCGATTTTACTTCCA
CCTGGCCACCTTCGAACCGGGGACCTTTCG tvA10:
(SEQ ID NO: 59)
AAAAAAGGTGGCCAGATGGAAGTAAACCAAGCTTCGTTTACTTCCATCT
GGCCACCCTTCGAACCGGGGACCTTTCG APP:
tvAPP
(SEQ ID NO: 60)
AAAAAATGAAGTGAAGATGGATGCAGCCAAGCTTCGCTGCATCCATCTT
CACTTCACTTCGAACCGGGGACCTTTCG tvT10/C11
(SEQ ID NO: 61)
AAAAAATGAAGTGAATCTGGATGCAGCCAAGCTTCGCTGCATCCAGATT
CACTTCACTTCGAACCGGGGACCTTTCG Cell Culture and Transfections.

Methods for culturing Cos-7 and HeLa cells have been described previously (Chai et al., 1999b). Plasmids and siRNAs were transiently transfected with Lipofectamine Plus (Invitrogen) in 12-well plates with cells plated at 70-90% confluency. For siRNA experiments, a 5:1 ratio of siRNA to expression plasmid was transfected into cells, while for tRNA-valine shRNA experiments, a 10:1 ratio of shRNA plasmid to expression plasmid was transfected into cells (Miller et al., 2003).

Western Blot Analysis.

Lysates from Cos-7 cells expressing GFP and tau constructs were harvested 24 h after transfection, while APP and APPsw expressing cell lysates were harvested at 48 h. Lysates from HeLa cells expressing endogenous lamin were harvested at 72 h after transfection of anti-lamin siRNA. Lysates were analyzed by Western blot as reported previously (Chai et al., 1999b). GFP and lamin were detected with anti-GFP mouse monoclonal antibody (1:1000 dilution; Medical and Biological Laboratories, Naka-ku Nagoya, Japan) and anti-lamin goat polyclonal antibody (1:25 dilution; Santa Cruz Biotechnology, Santa Cruz, Calif.) respectively. Additional antibodies used in this study include anti-tau mouse monoclonal antibody at 1:500 dilution (Calbiochem, San Diego, Calif.), 22C11 anti-APP mouse monoclonal antibody at 1:500 dilution (Chemicon International, Temecula, Calif.), and as a loading control, mouse monoclonal antibody to α-tubulin at 1:20,000 dilution (Sigma, St. Louis, Mo.). Secondary antibodies were peroxidase-conjugated donkey anti-goat or peroxidase-conjugated donkey anti-mouse (Jackson ImmunoResearch Laboratories, West Grove, Pa.) at 1:15,000 dilution.

Immunofluorescence.

48 hours after transfection, Cos-7 cells were fixed with 4% paraformaldehyde/PBS. APP and APPsw expression were detected with 22C11 at 1:1000 dilution, followed by fluorescein (FITC)-conjugated donkey anti-mouse secondary antibody (Jackson Labs) at 1:2,000 dilution. Nuclei were stained with 5 µg/ml 4',6-diamidine-2-phenylindole HCl (DAPI) at room temperature for 10 minutes. Fluorescence was visualized with a Zeiss (Thornwood, N.Y.) Axioplan fluorescence microscope. All images were captured digitally with a Zeiss MRM AxioCam camera and assembled in Photoshop 6.0 (Adobe Systems, Mountain View, Calif.).

Results

An Approach to In Vitro Transcription of siRNA that Eliminates Priming Constraints of T7 RNA Polymerase.

Figure 17A:
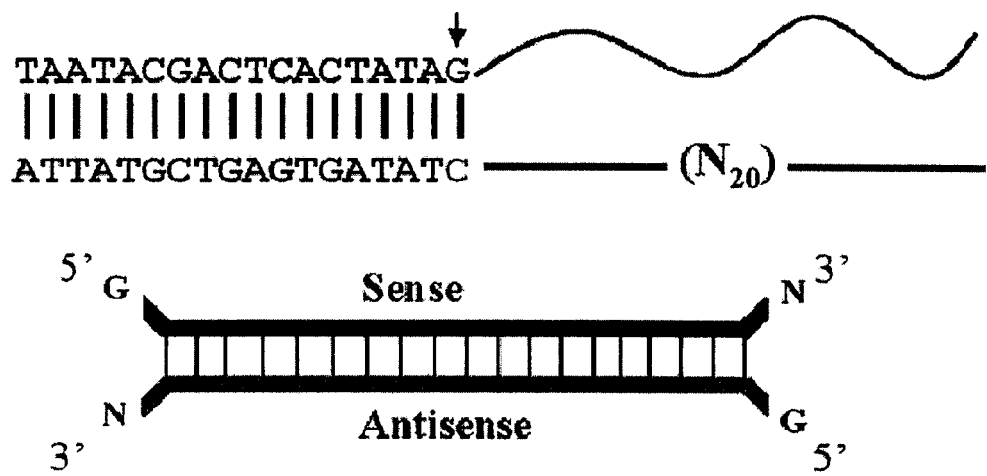
FIGS. 17A-17D. siRNA+G duplexes silence endogenous and reporter genes. (A) Schematic of siRNA synthesis depicting DNA template and structure of synthesized duplexes (SEQ ID NOs:10 and 62). Blue indicates the RNA product synthesized from the DNA template (upper). For the siRNA duplex, gray indicates the region with perfect complementarity to the intended target while black depicts the antisense sequence and additional non-complementary nucleotides added by the synthesis method. N represents any ribonucleotide. (B) Comparison of GFP silencing by perfectly complementary siRNA versus siRNA of the "+G" design. Images depict Cos-7 transfected with a GFP expression construct and the indicated siRNA. Images of GFP fluorescence are merged with images of the same field showing DAPI-stained nuclei. Shown on the left are results with negative control, mistargeted siRNAs (siMiss and siMiss+G respectively), which fail to silence GFP expression. On the right, GFP expression is efficiently suppressed by siRNA of both configurations. (C) Western blot analysis of lysates from the same experiment as in B. Tubulin staining is shown as a loading control. (D) Efficient silencing of endogenous lamin gene expression with siRNA+G duplexes. HeLa cells were transfected with the indicated siRNA and expression of lamin A/C was evaluated by western blot 72 hr later. The siRNA+G against human lamin markedly decreased protein levels relative to the mistargeted control siRNA.

An efficient way to create siRNAs against a gene of interest is to produce short RNA duplexes complementary to the target gene in in vitro transcription reactions employing T7 RNA polymerase. However, the priming requirements for T7 polymerase dictate that a G be the priming nucleotide initiating transcription (Kato et al., 2001). This limits the nucleotide positions in a target gene to which corresponding in vitro transcribed RNA duplexes can be generated. To overcome this restriction imposed by T7 RNA polymerase, siRNAs were designed that contained a noncomplementary G nucleotide at the 5' ends. The resulting siRNA contains 20 complementary nucleotides on the antisense strand with a single 5' mismatch to the target (FIG. 16 and FIG. 17A). This incorporation of an initiating G allows dsRNAs to be generated in vitro against any twenty nucleotide segment of a targeted gene.

Figure 17B:
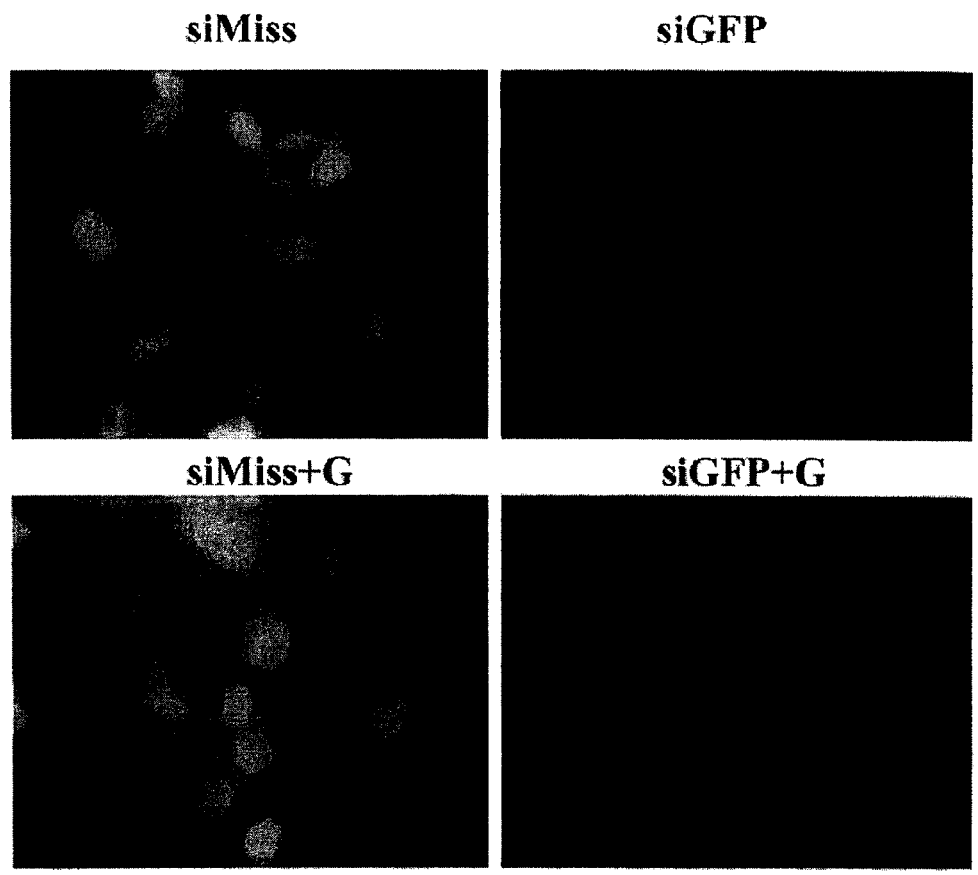
Figure 17C:
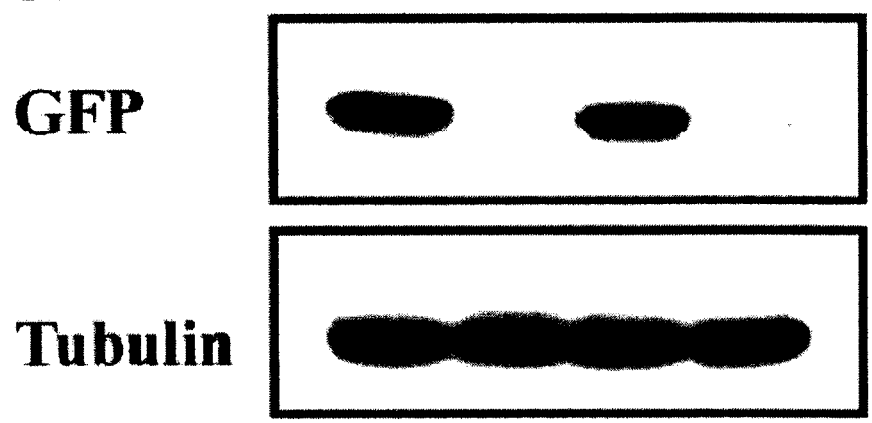
Figure 17D:
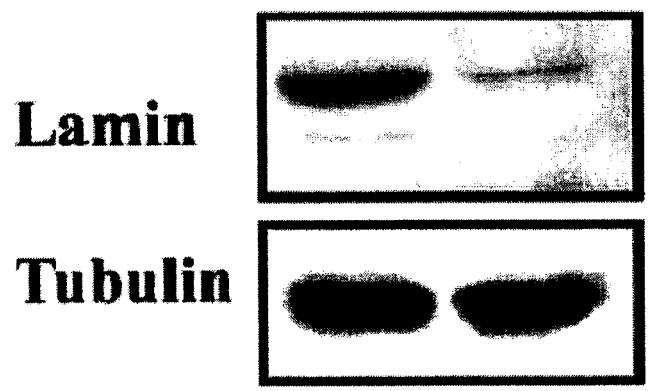

To determine whether adding this noncomplementary G still produced effective siRNAs, the inventors compared the silencing capability of this novel "+G" configuration to in vitro synthesized siRNA that was perfectly complementary to the target. The inventors assessed suppression of a reporter gene product, green fluorescent protein (GFP), and of an endogenous gene product, lamin (FIG. 17B, 17C, 17D). Cos-7 cells were co-transfected with a plasmid encoding GFP and siRNAs containing either a perfect match to the GFP mRNA or the single 5' G mismatch. siRNAs containing multiple mismatches were used as negative controls for any non-specific effects of the transfection or siRNA. As assessed by fluorescence microscopy and Western blot (FIG. 17B, 17C), the 5' mismatched siRNA displayed silencing efficiency similar to that of the perfectly matched siRNA targeted to the same region of the GFP mRNA.

The inventors next investigated the ability of these novel siRNAs to inhibit expression of an endogenous gene product, lamin. The inventors transfected HeLa cells with a negative control siRNA (siMiss) or a siRNA directed against endogenous lamin (Elbashir et al., 2001), and assessed expression 72 hr after transfection. Lamin expression was markedly reduced in cells transfected with siLamin+G, but remained robust in cells transfected with siMiss+G (FIG. 17D). Thus, "+G" siRNA remains an effective trigger of RNA interference.

Optimizing Allele-Specific Inhibition of Mutant Tau

In a previous study of the FTDP-17 tau mutant (V337M) (see Example 2 above), the inventors succeeded in engineering siRNA duplexes that preferentially silenced the mutant allele (Miller et al., 2003). Placing the mismatch near the center of the siRNA was most effective for allele discrimination, but due to the constraints imposed by T7 polymerase the inventors could not place the mutation precisely at the center of the siRNA. To enhance allele specificity in this earlier study, it was thus needed to introduce additional mismatches into the siRNA such that it contained two mismatches versus wild type alleles but only a single mismatch versus the mutant tau allele (Miller et al., 2003). Although this improved preferential suppression of the mutant allele, recent data suggest that siRNAs with multiple internal mismatches may act by inhibiting translation (via a microRNA-like mechanism) rather than by cleaving the targeted mRNA (Zeng et al., 2003; Doench et al., 2003). Accordingly, the inventors took advantage of the new siRNA synthesis strategy in an effort to improve allele-specific silencing with the single mismatch.

The inventors systematically tested the effect of placing the single nucleotide mismatch at each position near the predicted RISC cleavage site. Through this, it was hoped to identify siRNAs that would maximize allele specificity for V337M tau. The inventors co-transfected Cos-7 cells with flag epitope-tagged wild type tau, GFP-tagged mutant tau (V337M) and siRNAs in which the mutation had been placed at positions 9 through 12 of the targeted sequence. When the mismatch was placed at position 10 (siA10), the mutant allele was strongly suppressed (FIG. 18A). In contrast, placement of the mismatch more toward the 5' or 3' end of the target sequence resulted in siRNAs that poorly discriminated between alleles (FIG. 18A). It is important to note that although silencing of the mutant allele was strongly preferred with more centrally located mismatches, no siRNA was completely inactive against the wild type allele. Even with the mismatch optimally placed at position 10, some residual activity was still observed against the wild type allele. These results support the inventors' previous work (Miller et al., 2003; Gonzalez-Alegre et al., 2003) and results from other laboratories (Ding et al., 2003; Abdelgany et al., 2003; Martinez et al., 2002a) indicating that central mismatches at or near the RISC cleavage site are best at discriminating between alleles. However, specificity will also be determined in part by the precise nucleotide change (Ding et al., 2003). For some mutations, introducing additional mismatches at other sites in the siRNA may be required to obtain optimal specificity.

Therapeutic applications of siRNA to neurodegenerative diseases may require sustained intracellular production of siRNA. Accordingly, the inventors next constructed and tested shRNA expression plasmids against tau that were based on the inventors' most effective in vitro synthesized duplexes. Expression was driven by the tRNA-valine promoter (Kawasaki et al., 2003). The inventors again co-transfected flag-WT-tau and V337M-GFP mutant tau together with shRNA plasmids designed to target either wild type or mutant tau. The tvA10 plasmid, based on the siA10 siRNA, showed strong silencing of the mutant allele with only slight inhibition of wild type expression. An shRNA directed against the wild type allele silenced wild type tau expression but also produced some suppression of the mutant allele (FIG. 18B).

Thus, multiple siRNA designs can rapidly be generated and screened by the method described here in order to identify the best target sequence with which to create successful shRNA expression vectors. Once validated, these shRNAs can be incorporated into recombinant viral vectors for in vivo testing (Miller et al., 2003; Xia et al., 2002).

Allele-Specific Silencing of APP

Figure 19A:
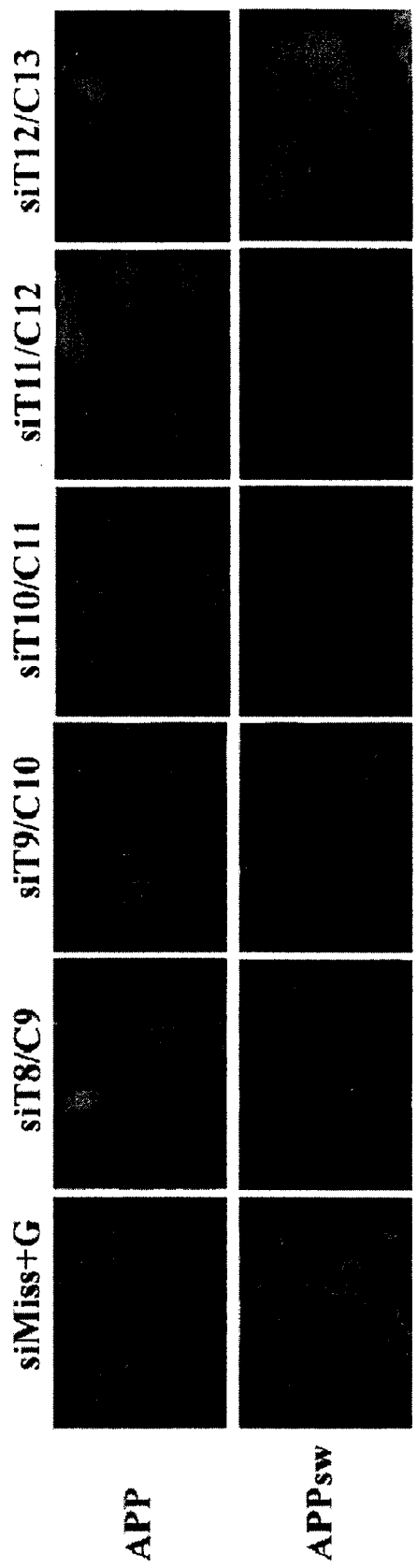

Next the inventors chose to test this approach with a second gene implicated in age-related dementia, the APP gene. Many mutations have been identified in APP that cause early onset, dominantly inherited AD (Alzheimer Disease Mutations Database: http://molgen-www.uia.ac.be/ADMutations/ and references therein). The inventors sought to suppress expression of wild type APP and the Swedish double APP mutation (K670N/M671L), or APPsw, a tandem nucleotide missense mutation that is widely employed in mouse models of AD (Mullan et al., 1992; Lewis et al., 2001; Oddo et al., 2003). The inventors systematically placed the tandem mismatch at each point in the central region of the siRNA duplexes to define the optimal placement for allele-specific suppression. APP silencing was assessed in Cos-7 cells cotransfected with constructs encoding wild type APP and APPsw together with the in vitro synthesized siRNAs. Similar to the results with tau, allelic discrimination was conferred only when the mismatches were placed centrally, as shown by APP immunofluorescence 48 hr after transfection (FIG. 19A). The inventors confirmed these results by Western blot analysis, which revealed highly specific silencing of APPsw with siT10/C11, the siRNA in which the double mismatch is placed immediately across from the presumed RISC cleavage site (FIG.

Figure 19B:
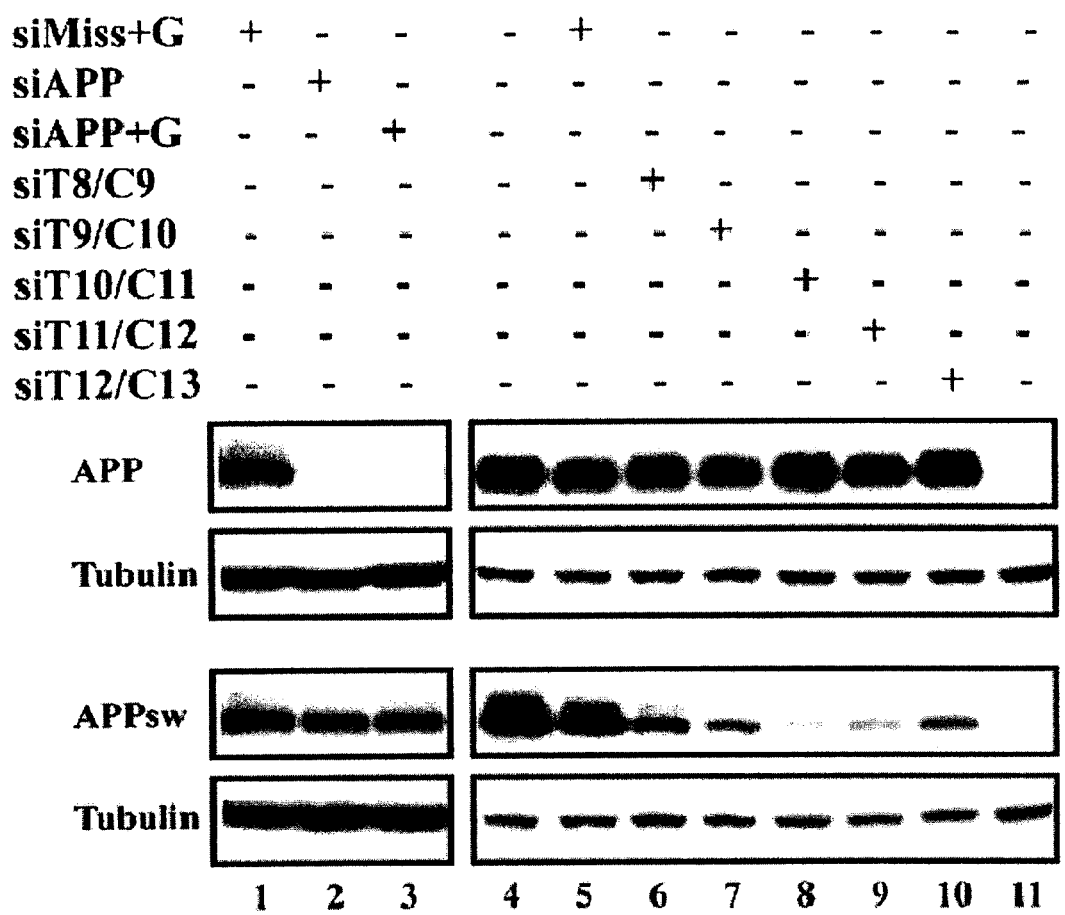

19B, lanes 5-10). The corresponding wild type-specific siRNA led to robust suppression of wild type APP (FIG. 19B, lanes 2-3).

Next, the inventors engineered plasmids expressing anti-APP shRNAs based on our most effective in vitro duplex sequences. As shown in FIG. 18C, shRNA designed to target the wild type sequence silenced only wild type APP expression, whereas shRNA designed to target APPsw specifically suppressed the mutant allele. These results describe novel and important reagents for functional studies of APP.

Discussion: Efficient siRNA Design for any Target Sequence

RNAi holds promise as a potential therapy for human diseases. Yet a limitation to successfully developing gene-specific or allele-specific siRNAs is the selection and design of siRNAs with the desired silencing characteristics. Individual siRNAs targeted to different regions of a transcript often display striking differences in efficacy and specificity (Miller et al., 2003; Ding et al., 2003). Typically, several target sites and designs need to be tested before optimal silencing is achieved (Miller et al., 2003). Here the inventors have described a simple method that not only circumvents the time and cost disadvantages of chemically synthesizing siRNA duplexes but also removes the sequence restrictions imposed by in vitro transcription with T7 polymerase.

The insertion of a single G mismatch at the 5' of the siRNA duplex permitted efficient priming by T7 polymerase without compromising the silencing efficacy of the resultant siRNA. Such "+G" siRNAs can rapidly be generated to essentially any point in a targeted gene and tested for efficacy. This approach to siRNA design facilitates the in vitro generation of effective siRNAs. As demonstrated here for two important disease targets, tau and APP, these in vitro transcribed duplexes can then serve as guides for producing shRNA plasmids that retain silencing capability and allele specificity. This approach represents an improved, stepwise method for optimized silencing of essentially any gene of interest.

Indeed, based on new insights into RISC assembly, manipulating the 5' terminal nucleotide of the guide strand in this way may be highly advantageous. Schwarz et al. (Schwarz et al., 2003) recently discovered marked asymmetry in the rate at which each strand of an RNA duplex enters the RISC complex. Preferential entry of the guide, or antisense, strand into RISC can be achieved by introducing 5' mismatches in the antisense strand while maintaining perfect base pairing at the 5' terminus of the sense strand. This maximizes entry of the antisense strand into the RISC complex, while also reducing potential off-target inhibition by the sense strand. The "+G" approach to siRNA design is perfectly suited to engineering dsRNAs based on this principle that should display preferred RISC entry of the guide strand.

Central Placement of Mismatches are Required for Allelic Discrimination

Using the present approach to in vitro siRNA production, the inventors were able to systematically test the effect of placing mismatches at each point along the guide strand of the siRNA. For tau and APP, central placement of mismatches resulted in optimal allele-specific silencing of mutant alleles. With the APPsw double mutation, for example, the inventors found that placing the two mismatches immediately across from the predicted RISC cleavage site resulted in highly specific allele discrimination. These results demonstrate the importance of central placement of mutations for successful allele-specific silencing.

For tau, however, siRNAs with centrally placed mismatches still retained some activity against the wild type allele. This suggests that both the position of the mismatch along the guide strand and the chemical nature of the mismatch are important for determining whether RISC associated nucleases will cleave a given mRNA. For example, in RNAi studies targeting a single nucleotide change in the polyglutamine disease gene MJD1, a G-G clash between the antisense strand of the siRNA and the target mRNA resulted in a complete inability to silence the wild type allele while the mutant allele was strongly suppressed (Miller et al., 2003). In contrast, even with the tau (V337M) mutation optimally placed centrally in the siRNA, some silencing of wild type tau was observed (Miller et al., 2003). This suggests that the less disruptive G-U clash in the case of the tau mutation does not allow for complete allelic discrimination by siRNA. In such cases additional mismatches may need to be incorporated into the siRNA.

Experimental and Therapeutic Implications

The RNAi reagents developed here against tau and APP constitute an experimental and potential therapeutic advance for AD and related dementias. Although abnormal deposition of tau and the APP cleavage product Aβ are central to AD pathogenesis, the precise roles of these proteins in the brain remain to be elucidated (hardy et al., 2002; Lee et al., 2001). These siRNA reagents, which can be used to selectively silence expression of mutant or wild type tau and APP, should facilitate loss of function experiments aimed at identifying the neuronal functions of these proteins.

For potential therapeutic applications of siRNA, the inventors have established expression vectors that silence mutant or wild type forms of tau and APP. For individuals with dominantly inherited AD or tauopathy, selective removal of the mutant protein might ameliorate or even prevent disease. The demonstration of specific silencing of mutant alleles extends the potential utility of the approach to genes with important or essential functions. For APP, specific silencing of either the widely studied Swedish double mutant or wild type APP was achieved. Reagents that suppress APPsw are useful in testing RNAi therapy in mouse models of AD, and reduction of wild type APP also has therapeutic potential for the common, sporadic form of AD. Based on the amyloid cascade hypothesis of AD, the most selective intervention would be a reagent that suppresses APP protein production with minimal effects on unintended targets (Hardy et al., 2002). Aβ production requires cleavage of APP by two proteases, the β site APP-cleaving enzyme BACE and the γ-secretase complex, which contains presenilin (Sisodia et al., 2002). Thus, additional gene targets in AD include BACE and, for most familial AD, dominantly acting presenilin mutations.

A major challenge in applying siRNA therapy to the nervous system is achieving sustained, effective delivery of siRNA to the correct target cells in the brain. These data, combined with in vivo results from other groups (Xia et al., 2002; Rubinson et al., 2003), suggest that siRNA will effectively suppress expression of the targeted gene, provided that it can be delivered efficiently to the appropriate neurons. Hope is offered by the observation here and elsewhere that sustained intracellular production of siRNA can be achieved with expression plasmids. These plasmids retain their silencing characteristics when incorporated into viral vectors that are known to transduce CNS neurons (Davidson et al., 2003).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

CITATIONS

Abdelgany et al., *Hum. Mol Genet.*, 12, 2637-3644 (2003).
Adelman et al., *DNA*, 2, 183 (1983).
Alisky et al., *Hum Gen Ther*, 11, 2315 (2000b).
Alisky et al., *NeuroReport*, 11, 2669 (2000a).
Altschul et al., *JMB*, 215, 403 (1990).
Altschul et al., *Nucleic Acids Res.* 25, 3389 (1997).
Ambrose et al, *Somat Cell Mol Genet.* 20, 27-38 (1994)
Anderson et al., *Gene Ther.*, 7(12), 1034-8 (2000).
Andreason and Evans, *Biotechniques*, 6, 650 (1988).
Augood et al., *Neurology*, 59, 445-8 (2002).
Augood et al., *Ann. Neurol.*, 46, 761-769 (1999).
Bass, *Nature*, 411, 428 (2001).
Batzer et al., *Nucl. Acids Res.*, 19, 508 (1991).
Baulcombe, *Plant Mol. Biol.*, 32, 79 (1996).
Behr et al., *Proc. Natl. Acad. Sci. USA*, 86, 6982 (1989).
Bernstein et al., *Nature*, 409, 363 (2001).
Bledsoe et al., *NatBiot*, 18, 964 (2000).
Brantl, *Biochemica and Biophysica Acta*, 1575, 15 (2002).
Brash et al., *Molec. Cell. Biol.*, 7, 2031 (1987).
Breakefield et al., *Neuron*, 31, 9-12 (2001).
Brooks et al., *Proc. Natl. Acad. Sci. U.S.A.*, 99, 6216 (2002).
Brummelkamp, T. R. et al., *Science* 296:550-553 (2002).
Capecchi, *Cell*, 22, 479 (1980).
Caplan et al., *Proc. Natl. Acad. Sci. U.S.A.*, 98, 9742 (2001).
Caplen et al., *Hum. Mol. Genet.*, 11(2), 175-84 (2002).
Cemal et al., *Hum. Mol. Genet.*, 11(9), 1075-94 (2002).
Chai et al., *Hum. Mol. Genet.*, 8, 673-682 (1999b).
Chai et al., *J. Neurosci.*, 19, 10338 (1999).
Chan et al., *Hum Mol Genet.*, 9(19), 2811-20 (2000).
Chiu and Rana, *Mol. Cell.*, 10(3), 549-61 (2002).
Cogoni et al., *Antonie Van Leeuwenhoek*, 65, 205 (1994).
Corpet et al., *Nucl. Acids Res.*, 16, 10881 (1988).
Crea et al., *Proc. Natl. Acad. Sci. U.S.A.*, 75, 5765 (1978).
Cullen, *Nat. Immunol.*, 3, 597-9 (2002).
Davidson et al., *Proc. Natl. Acad. Sci. U.S.A.*, 97, 3428 (2000).
Davidson et al., *Nat Rev Neurosci.*, 4(5) 353-64 (2003).
Dayhoff et al., *Atlas of Protein Sequence and Structure* (Natl. Biomed. Res. Found. 1978).
Ding et al., *Aging Cell.*, 2, 209-217 (2003).
Doench et al., *Genes Dev.*, 17(4), 438-42 (2003).
Doheny et al., *Neurology*, 59, 1244-1246 (2002).
Donze and Picard, *Nucleic Acids Res.*, 30(10), e46 (2002).
Elbashir et al., *EMBO J.*, 20(23), 6877-88 (2001c).
Elbashir et al., *Genes and Development*, 15, 188 (2001).
Elbashir et al., *Nature*, 411, 494 (2001).
Fahn et al., *Adv. Neurol.*, 78, 1-10 (1998).
Feigner et al., *Proc. Natl. Acad. Sci.*, 84, 7413 (1987).
Fire et al., *Nature*, 391(6669), 806-11 (1998).
Gaspar et al., *Am. J. Hum. Genet.*, 68(2), 523-8 (2001).
Gelfand, *PCR Strategies*, Academic Press (1995).
Gitlin et al., *Nature*, 418(6896), 430-4 (2002).
Goeddel et al., *Nucleic Acids Res.*, 8, 4057 (1980).
Gonzalez-Alegre et al., *Ann Neurol.*, 53, 781-787 (2003).
Goodchild et al., *Mov. Disord.*, 17(5), 958, Abstract (2002).
Hamilton and Baulcombe, *Science*, 286, 950 (1999).
Hammond et al., *Nature*, 404, 293 (2000).
Hardy et al., *Science*, 297(5580), 353-6 (2002).
Hewett et al., *Hum. Mol. Gen.*, 9, 1403-1413 (2000).
Higgins et al., *CABIOS*, 5, 151 (1989).
Higgins et al., *Gene*, 73, 237 (1988).
Hilberg et al., *Proc. Natl. Acad. Sci. USA*, 84, 5232 (1987).
Holland et al., *Proc. Natl. Acad. Sci. USA*, 84, 8662 (1987).
Hornykiewicz et al., *N. Engl. J. Med.*, 315, 347-353 (1986).
Houlden et al., *Neurology*, 56(12), 1702-6 (2001).
Huang et al., *CABIOS*, 8, 155 (1992).
Hutton et al., *Nature*, 393, 702-705 (1998).
Innis and Gelfand, *PCR Methods Manual*, Academic Press (1999).
Innis et al., *PCR Protocols*, Academic Press (1995).
Jacque et al., *Nature*, 418(6896), 435-8 (2002).
Johnston, *Nature*, 346, 776 (1990).
Karlin and Altschul, *Proc. Natl. Acad. Sci. USA*, 87, 2264 (1990).
Karlin and Altschul, *Proc. Natl. Acad. Sci. USA*, 90, 5873 (1993).
Kato et al., *J Biol Chem.*, 76(24), 21809-20 (2001).
Kawasaki et al., *Nucleic Acids Res.*, 31(2), 700-7 (2003).
Kennerdell and Carthew, *Cell*, 95, 1017 (1998).
Kitabwalla and Ruprecht, *N. Engl. J. Med.*, 347, 1364-1367 (2002).
Klein et al., *Ann. Neurol.*, 52, 675-679 (2002).
Klein et al., *Curr. Opin. Neurol.*, 4, 491-7 (2002).
Konakova et al., *Arch. Neurol.*, 58, 921-927 (2001).
Koseki et al., *J. Virol.*, 73, 1868-1877 (1999).
Krichevsky and Kosik, *Proc. Natl. Acad. Sci. U.S.A.*, 99(18), 11926-9 (2002).
Kriegler, M. Gene Transfer and Expression, A Laboratory Manual, W.H. Freeman Co, New York, (1990).
Kunkel et al., *Meth. Enzymol.*, 154, 367 (1987).
Kunkel, *Proc. Natl. Acad. Sci. USA*, 82, 488 (1985).
Kustedjo et al., *J. Biol. Chem.*, 275, 27933-27939 (2000).
Laccone et al., *Hum. Mutat.*, 13(6), 497-502 (1999).
Lai et al., *Proc. Natl. Acad. Sci. USA*, 86, 10006 (1989).
Larrick, J. W. and Burck, K. L., Gene Therapy. Application of Molecular Biology, Elsevier Science Publishing Co., Inc., New York, p. 71-104 (1991).
Lawn et al., *Nucleic Acids Res.*, 9, 6103 (1981).
Lee, N. S., et al., *Nat. Biotechnol.* 19:500-505 (2002).
Lee et al., *Annu Rev Neurosci.*, 24, 1121-59 (2001).
Leger et al., *J. Cell. Sci.*, 107, 3403-12 (1994).
Leung et al., *Neurogenetics*, 3, 133-43 (2001).
Lewis et al., *Science*, 293(5534), 1487-91 (2001).
Lin et al., *Hum. Mol. Genet.*, 10(2), 137-44 (2001).
Loeffler et al., *J. Neurochem.*, 54, 1812 (1990).
Manche et al., *Mol. Cell Biol.*, 12, 5238 (1992).
Margolis and Ross, Trends *Mol. Med.*, 7, 479 (2001).
Martinez et al., *Cell*, 110(5), 563-74 (2002).
Martinez et al., *Proc. Natl. Acad. Sci. USA*, 99, 14849-54 (2002a).
McCaffrey et al., *Nature*, 418(6893), 38-9 (2002).
McManus and Sharp, *Nat. Rev. Genet.* 3(10), 737-47 (2002).
Meinkoth and Wahl, *Anal. Biochem.*, 138, 267 (1984).
Methods in Molecular Biology, 7, Gene Transfer and Expression Protocols, Ed. E. J. Murray, Humana Press (1991).
Miller, et al., *Mol. Cell. Biol.*, 10, 4239 (1990).
Miller et al., *Proc. Natl. Acad. Sci USA*, 100, 7195-7200 (2003).
Minks et al., *J. Biol. Chem.*, 254, 10180 (1979).
Miyagishi, M. & Taira, K. *Nat. Biotechnol.* 19:497-500 (2002).
Moulder et al., *J. Neurosci.*, 19, 705 (1999).
Mullan et al., *Nature Genetics*, 1, 345-347 (1992).
Murray, E. J., ed. Methods in Molecular Biology, Vol. 7, Humana Press Inc., Clifton, N.J., (1991).
Myers and Miller, *CABIOS*, 4, 11 (1988).

Nasir et al., *Cell*, 81, 811-823 (1995).
Needleman and Wunsch, *JMB*, 48, 443 (1970).
Nykänen et al., *Cell*, 107, 309 (2001).
Oddo et al., *Neuron.*, 39(3), 409-21 (2003).
Ogura and Wilkinson, *Genes Cells*, 6, 575-97 (2001).
Ohtsuka et al., *JBC*, 260, 2605 (1985).
Okabe et al., *FEBS Lett.*, 407, 313 (1997).
Ooboshi et al., *Arterioscler. Thromb. Vasc. Biol.*, 17, 1786 (1997).
Ozelius et al., *Genomics*, 62, 377-84 (1999).
Ozelius et al., *Nature Genetics*, 17, 40-48 (1997).
Paul, C. P., et al., *Nat. Biotechnol.* 19:505-508 (2002).
Paulson et al., *Ann. Neurol.*, 41(4), 453-62 (1997).
Pearson and Lipman, *Proc. Natl. Acad. Sci. USA*, 85, 2444 (1988).
Pearson et al., *Meth. Mol. Biol.*, 24, 307 (1994).
Pittman et al., *J. Neurosci.*, 13(9), 3669-80 (1993).
Poorkaj et al., *Ann. Neurol.*, 43, 815-825 (1998).
Quantin, B., et al., *Proc. Natl. Acad. Sci. USA*, 89, 2581 (1992).
Rosenfeld, M. A., et al., *Science*, 252, 431 (1991).
Rossolini et al., *Mol. Cell. Probes*, 8, 91 (1994).
Rubinson et al., *Nat Genet.*, 33(3), 401-6 (2003).
Sambrook and Russell, *Molecular Cloning: A Laboratory Manual*, Cold Spring Harbor Laboratory Press Cold Spring Harbor, N.Y. (2001).
Scharfmann et al., *Proc. Natl. Acad. Sci. USA*, 88, 4626 (1991).
Schwarz et al., *Mol. Cell.*, 10(3), 537-48 (2002).
Schwarz et al., *Cell*, 115(2), 199-208 (2003).
Shipley et al., *J. Biol. Chem.*, 268, 12193 (1993).
Sisodia et al., *Nat Rev Neurosci.*, 3(4), 281-90 (2002).
Smith et al., *Adv. Appl. Math.*, 2, 482 (1981).
Song et al., *Nat. Med.*, 9, 347-51 (2003).
Stein et al., *J. Virol.*, 73, 3424 (1999).
Stein et al., *RNA*, 9(2), 187-192 (2003).
Svoboda et al., *Development*, 127, 4147 (2000).
Tanemura et al., *J. Neurosci.*, 22(1), 133-41 (2002).
Tang et al., *Genes Dev.*, 17(1), 49-63 (2003).
Terpin, H., "Retrovirus vectors for gene transfer", in Gene Transfer, Kucherlapati R, Ed., pp 149-187, Plenum, (1986).
Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, New York (1993).
Timmons and Fire, *Nature*, 395, 854 (1998).
Trottier et al., *Nature*, 378(6555), 403-6 (1995).
Turner et al., *Mol. Biotech.*, 3, 225 (1995).
Tuschl, *Nat. Biotechnol.*, 20, 446-8 (2002).
Valerio et al., *Gene*, 84, 419 (1989).
Viera et al., *Meth. Enzymol.*, 153, 3 (1987).
Walker and Gaastra, *Techniques in Mol. Biol.* (MacMillan Publishing Co. (1983).
Walker et al., *Neurology*, 58, 120-4 (2002).
Waterhouse et al., *Proc. Natl. Acad. Sci. U.S.A.*, 95, 13959 (1998).
Wianny and Zernicka-Goetz, *Nat. Cell Biol.*, 2, 70 (2000).
Xia et al., *Nat. Biotechnol.*, 19, 640 (2001).
Xia et al., *Nat. Biotechnol.*, 20(10), 1006-10 (2002).
Yamamoto et al., *Cell*, 101(1), 57-66 (2000).
Yang et al., *Mol. Cell Biol.*, 21, 7807 (2001).
Zamore et al., *Cell*, 101, 25 (2000).
Zeng et al., *Proc Natl Acad Sci USA*, 100(17), 9779-84 (2003).
Zoghbi and Orr, *Annu. Rev. Neurosci.*, 23, 217-47 (2000).

---

What is claimed is:

1. A mammalian cell comprising
a first strand of RNA of 15 to 30 nucleotides in length having a 5' end and a 3' end, wherein the first strand is complementary to at least 15 nucleotides of a mutant Ataxin-3 transcript encoded by siC7 (5'-CTGTCCT-GATAGGTCCCGCTGC-3' SEQ ID NO: 16), siG10 (5'-CTGATAGGTCCCCCTGCTGC-3' SEQ ID NO:18), siC7/8 (5'-CTGTCCTGATAGGTCCG-GCTGC-3' SEQ ID NO:20), or siC10 (5'-CTGATAG-GTCCCGCTGCTGC-3' SEQ ID NO:22), and wherein the 5' end of the first strand of RNA is operably linked to a G nucleotide to form a first segment of RNA, and
a second strand of RNA of 15 to 30 nucleotides in length having a 5' end and a 3' end,
wherein at least 12 nucleotides of the first and second strands are complementary to each other and form a small interfering RNA (siRNA) duplex under physiological conditions, and wherein the siRNA silences only one allele of the targeted gene in the cell.

2. The cell of claim 1, wherein the first strand and the second strand are operably linked by means of an RNA loop strand to form a hairpin structure comprising a duplex structure and a loop structure.

3. The cell of claim 2, wherein the loop structure contains from 4 to 10 nucleotides.

4. An isolated RNA duplex comprising a first strand of RNA having a 5' end and a 3' end, and a second strand of RNA, wherein the first strand comprises 22 nucleotides complementary to mutant Ataxin-3 transcript encoded by siC7 (5'-CTGTCCTGATAGGTCCCGCTGC-3' SEQ ID NO: 16), siG10 (5'-CTGATAGGTCCCCCTGCTGC-3' SEQ ID NO:18), siC7/8 (5'-CTGTCCTGATAGGTCCGGCTGC-3' SEQ ID NO:20), or siC10 (5'-CTGATAGGTCCCGCT-GCTGC-3' SEQ ID NO:22), wherein the 5' end of the first strand of RNA is operably linked to a G nucleotide to form a first segment of RNA, and wherein the second strand is complementary to all the nucleotides of the first strand.

5. The RNA duplex of claim 4, wherein the first strand and the second strand are operably linked by means of an RNA loop strand to form a hairpin structure comprising a duplex structure and a loop structure.

6. The RNA duplex of claim 4, wherein the loop structure contains from 4 to 10 nucleotides.

7. An expression cassette comprising a nucleic acid encoding at least one strand of the RNA duplex of claim 4.

8. A vector comprising the expression cassette of claim 7.

9. A vector comprising two expression cassettes, a first expression cassette comprising a nucleic acid encoding the first strand of the RNA duplex of claim 4 and a second expression cassette comprising a nucleic acid encoding the second strand of the RNA duplex of claim 4.

10. A cell comprising the expression cassette of claim 7.

11. An isolated RNA duplex comprising a first strand of RNA having a 5' end and a 3' end, and a second strand of RNA, wherein the first strand comprises 22 nucleotides complementary to mutant APP transcript encoded by siT8/C9 (5'-ATTCTGCATCCAGATTCACT-3' SEQ ID NO: 83), siT9/C10 (5'-TTCTGCATCCAGATTCACTT-3' SEQ ID NO:85), siT10/C11 (5'-TCTGCATCCAGATTCACTTC-3' SEQ ID NO:86), siT11/C12 (5'-TGCATCCAGATTCACT-TCA-3' SEQ ID NO:88), or siT12/C13 (5'-TGCATCCA-GATTCACTTCAG-3' SEQ ID NO: 90), wherein the 5' end of the first strand of RNA is operably linked to a G nucleotide to form a first segment of RNA, and wherein the second strand is complementary to all the nucleotides of the first strand.

12. The RNA duplex of claim 11, wherein the first strand and the second strand are operably linked by means of an RNA loop strand to form a hairpin structure comprising a duplex structure and a loop structure.

13. The RNA duplex of claim 11, wherein the loop structure contains from 4 to 10 nucleotides.

14. An expression cassette comprising a nucleic acid encoding at least one strand of the RNA duplex of claim 11.

15. A vector comprising the expression cassette of claim 14.

16. A vector comprising two expression cassettes, a first expression cassette comprising a nucleic acid encoding the first strand of the RNA duplex of claim 14 and a second expression cassette comprising a nucleic acid encoding the second strand of the RNA duplex of claim 14.

17. A cell comprising the expression cassette of claim 14.

18. A mammalian cell comprising
an isolated first strand of RNA of 15 to 30 nucleotides in length having a 5' end and a 3' end, wherein the first strand is complementary to at least 15 nucleotides of mutant APP transcript encoded by siT8/C9 (5'-ATTCT-GCATCCAGATTCACT-3' SEQ ID NO: 83), siT9/C10 (5'-TTCTGCATCCAGATTCACTT-3' SEQ ID NO:85), siT10/C11 (5'-TCTGCATCCAGAT-TCACTTC-3' SEQ ID NO:86), siT11/C12 (5'-TG-CATCCAGATTCACTTCA-3' SEQ ID NO:88), or siT12/C13 (5'-TGCATCCAGATTCACTTCAG-3' SEQ ID NO: 90), and wherein the 5' end of the first strand of RNA is operably linked to a G nucleotide to form a first segment of RNA, and
an isolated second strand of RNA of 15 to 30 nucleotides in length having a 5' end and a 3' end,
wherein at least 12 nucleotides of the first and second strands are complementary to each other and form a small interfering RNA (siRNA) duplex under physiological conditions, and wherein the siRNA silences only one allele of the targeted gene in the cell.

19. The cell of claim 18, wherein the first strand and the second strand are operably linked by means of an RNA loop strand to form a hairpin structure comprising a duplex structure and a loop structure.

20. The cell of claim 19, wherein the loop structure contains from 4 to 10 nucleotides.

* * * * *

UNITED STATES PATENT AND TRADEMARK OFFICE
CERTIFICATE OF CORRECTION

PATENT NO. : 9,487,779 B2  
APPLICATION NO. : 14/297378  
DATED : November 8, 2016  
INVENTOR(S) : Beverly L. Davidson et al.

Page 1 of 1

It is certified that error appears in the above-identified patent and that said Letters Patent is hereby corrected as shown below:

On the Title Page

Item (63), Related U.S. Application Data, please delete "PCT/US03/16887, filed on May 6, 2003" and insert -- PCT/US03/16887, filed on May 26, 2003 --;

In the Claims

Column 93, Line 30, Claim 1, please delete "Ataxin-3" and insert -- *Ataxin-3* --;

Column 93, Line 55, Claim 4, please delete "Ataxin-3" and insert -- *Ataxin-3* --;

Column 94, Line 39, Claim 11, please delete "APP" and insert -- *APP* --;

Column 95, Line 5, Claim 18, please delete "APP" and insert -- *APP* -- therefor.

Signed and Sealed this  
Seventeenth Day of October, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 90

<210> SEQ ID NO 1
<211> LENGTH: 40
<212> TYPE: DNA
<213> ORGANISM: Artificial Sequence
<220> FEATURE:
<223> OTHER INFORMATION: A synthetic primer

<400> SEQUENCE: 1
aaggtaccag atcttagtta ttaatagtaa tcaattacgg                              40

<210> SEQ ID NO 2
<211> LENGTH: 43
<212> TYPE: DNA
<213> ORGANISM: Artificial Sequence
<220> FEATURE:
<223> OTHER INFORMATION: A synthetic primer

<400> SEQUENCE: 2
gaatcgatgc atgcctcgag acggttcact aaaccagctc tgc                         43

<210> SEQ ID NO 3
<211> LENGTH: 69
<212> TYPE: DNA
<213> ORGANISM: Artificial Sequence
<220> FEATURE:
<223> OTHER INFORMATION: A synthetic oligonucleotide used with SEQ ID
      NO:4 to form a minimal polyA
```

-continued

<400> SEQUENCE: 3
ctagaactag taataaagga tcctttattt tcattggatc cgtgtgttgg ttttttgtgt    60
gcggccgcg                                                            69

<210> SEQ ID NO 4
<211> LENGTH: 69
<212> TYPE: DNA
<213> ORGANISM: Artificial Sequence
<220> FEATURE:
<223> OTHER INFORMATION: A synthetic oligonucleotide used with SEQ ID
      NO:3 to form a minimal polyA

<400> SEQUENCE: 4
tcgacgcggc cgcacacaaa aaaccaacac acggatccaa tgaaaataaa ggatccttta    60
ttactagtt                                                            69

<210> SEQ ID NO 5
<211> LENGTH: 21
<212> TYPE: DNA
<213> ORGANISM: Artificial Sequence
<220> FEATURE:
<223> OTHER INFORMATION: A synthetic P32 labeled sense oligonucleotide
      used to probe a blot

<400> SEQUENCE: 5
cacaagctgg agtacaacta c                                              21

<210> SEQ ID NO 6
<211> LENGTH: 22
<212> TYPE: DNA
<213> ORGANISM: Artificial Sequence
<220> FEATURE:
<223> OTHER INFORMATION: A synthetic P32 labeled antisense
      oligonucleotide used to probe a blot

<400> SEQUENCE: 6
gtacttgtac tccagctttg tg                                             22

<210> SEQ ID NO 7
<211> LENGTH: 28
<212> TYPE: DNA
<213> ORGANISM: Homo sapiens

<400> SEQUENCE: 7
cagcagcagc aggggggacct atcaggac                                      28

<210> SEQ ID NO 8
<211> LENGTH: 28
<212> TYPE: DNA
<213> ORGANISM: Homo sapiens

<400> SEQUENCE: 8
cagcagcagc agcgggacct atcaggac                                       28

<210> SEQ ID NO 9
<211> LENGTH: 17
<212> TYPE: DNA
<213> ORGANISM: Artificial Sequence
<220> FEATURE:
<223> OTHER INFORMATION: A synthetic T7 promoter sequence

<400> SEQUENCE: 9
tatagtgagt cgtatta                                                   17

<210> SEQ ID NO 10
<211> LENGTH: 18
<212> TYPE: DNA
<213> ORGANISM: Artificial Sequence
<220> FEATURE:
<223> OTHER INFORMATION: A synthetic primer annealed to all oligos to
      synthesize siRNAs

<400> SEQUENCE: 10
taatacgact cactatag                                                    18

<210> SEQ ID NO 11
<211> LENGTH: 22
<212> TYPE: DNA
<213> ORGANISM: Homo sapiens

<400> SEQUENCE: 11
cggcaagctg cgcatgaagt tc                                               22

<210> SEQ ID NO 12
<211> LENGTH: 22
<212> TYPE: DNA
<213> ORGANISM: Homo sapiens

<400> SEQUENCE: 12
atgaacttca tgctcagctt gc                                               22

<210> SEQ ID NO 13
<211> LENGTH: 22
<212> TYPE: DNA
<213> ORGANISM: Homo sapiens

<400> SEQUENCE: 13
atgaacttca gggtcagctt gc                                               22

<210> SEQ ID NO 14
<211> LENGTH: 22
<212> TYPE: DNA
<213> ORGANISM: Homo sapiens

<400> SEQUENCE: 14
cggcaagctg accctgaagt tc                                               22

<210> SEQ ID NO 15
<211> LENGTH: 22
<212> TYPE: DNA
<213> ORGANISM: Homo sapiens

<400> SEQUENCE: 15
cagcagcggg acctatcagg ac                                               22

<210> SEQ ID NO 16
<211> LENGTH: 22
<212> TYPE: DNA
<213> ORGANISM: Homo sapiens

<400> SEQUENCE: 16
ctgtcctgat aggtcccgct gc                                               22

<210> SEQ ID NO 17
<211> LENGTH: 20
<212> TYPE: DNA
<213> ORGANISM: Homo sapiens

<400> SEQUENCE: 17
cagcagcagg gggacctatc                                           20

<210> SEQ ID NO 18
<211> LENGTH: 20
<212> TYPE: DNA
<213> ORGANISM: Homo sapiens

<400> SEQUENCE: 18
ctgataggtc cccctgctgc                                           20

<210> SEQ ID NO 19
<211> LENGTH: 22
<212> TYPE: DNA
<213> ORGANISM: Homo sapiens

<400> SEQUENCE: 19
cagcagccgg acctatcagg ac                                        22

<210> SEQ ID NO 20
<211> LENGTH: 22
<212> TYPE: DNA
<213> ORGANISM: Homo sapiens

<400> SEQUENCE: 20
ctgtcctgat aggtccggct gc                                        22

<210> SEQ ID NO 21
<211> LENGTH: 20
<212> TYPE: DNA
<213> ORGANISM: Homo sapiens

<400> SEQUENCE: 21
cagcagcagc gggacctatc                                           20

<210> SEQ ID NO 22
<211> LENGTH: 20
<212> TYPE: DNA
<213> ORGANISM: Homo sapiens

<400> SEQUENCE: 22
ctgataggtc ccgctgctgc                                           20

<210> SEQ ID NO 23
<211> LENGTH: 21
<212> TYPE: DNA
<213> ORGANISM: Homo sapiens

<400> SEQUENCE: 23
ttgaaaaaca gcagcaaaag c                                         21

<210> SEQ ID NO 24
<211> LENGTH: 21
<212> TYPE: DNA
<213> ORGANISM: Homo sapiens

<400> SEQUENCE: 24
ctgcttttgc tgctgttttt c                                         21

<210> SEQ ID NO 25
<211> LENGTH: 22
<212> TYPE: DNA

```
<213> ORGANISM: Homo sapiens

<400> SEQUENCE: 25
cagcagcagc agcagcagca gc                                              22

<210> SEQ ID NO 26
<211> LENGTH: 22
<212> TYPE: DNA
<213> ORGANISM: Homo sapiens

<400> SEQUENCE: 26
ctgctgctgc tgctgctgct gc                                              22

<210> SEQ ID NO 27
<211> LENGTH: 22
<212> TYPE: DNA
<213> ORGANISM: Homo sapiens

<400> SEQUENCE: 27
tcgaagtgat ggaagatcac gc                                              22

<210> SEQ ID NO 28
<211> LENGTH: 22
<212> TYPE: DNA
<213> ORGANISM: Homo sapiens

<400> SEQUENCE: 28
cagcgtgatc ttccatcact tc                                              22

<210> SEQ ID NO 29
<211> LENGTH: 22
<212> TYPE: DNA
<213> ORGANISM: Homo sapiens

<400> SEQUENCE: 29
cagccgggag tcgggaaggt gc                                              22

<210> SEQ ID NO 30
<211> LENGTH: 22
<212> TYPE: DNA
<213> ORGANISM: Homo sapiens

<400> SEQUENCE: 30
ctgcaccttc ccgactcccg gc                                              22

<210> SEQ ID NO 31
<211> LENGTH: 24
<212> TYPE: DNA
<213> ORGANISM: Homo sapiens

<400> SEQUENCE: 31
acgtcctcgg cggcggcagt gtgc                                            24

<210> SEQ ID NO 32
<211> LENGTH: 24
<212> TYPE: DNA
<213> ORGANISM: Homo sapiens

<400> SEQUENCE: 32
ttgcacactg ccgcctccgc ggac                                            24

<210> SEQ ID NO 33
<211> LENGTH: 21
```

```
<212> TYPE: DNA
<213> ORGANISM: Homo sapiens

<400> SEQUENCE: 33
acgtctccat ggcatctcag c                                              21

<210> SEQ ID NO 34
<211> LENGTH: 21
<212> TYPE: DNA
<213> ORGANISM: Homo sapiens

<400> SEQUENCE: 34
ttgctgagat gccatggaga c                                              21

<210> SEQ ID NO 35
<211> LENGTH: 22
<212> TYPE: DNA
<213> ORGANISM: Homo sapiens

<400> SEQUENCE: 35
gtggccagat ggaagtaaaa tc                                             22

<210> SEQ ID NO 36
<211> LENGTH: 22
<212> TYPE: DNA
<213> ORGANISM: Homo sapiens

<400> SEQUENCE: 36
cagattttac ttccatctgg cc                                             22

<210> SEQ ID NO 37
<211> LENGTH: 22
<212> TYPE: DNA
<213> ORGANISM: Homo sapiens

<400> SEQUENCE: 37
gtggccacat ggaagtaaaa tc                                             22

<210> SEQ ID NO 38
<211> LENGTH: 22
<212> TYPE: DNA
<213> ORGANISM: Homo sapiens

<400> SEQUENCE: 38
cagattttac ttccatgtgg cc                                             22

<210> SEQ ID NO 39
<211> LENGTH: 22
<212> TYPE: DNA
<213> ORGANISM: Homo sapiens

<400> SEQUENCE: 39
gtggccagat gcaagtaaaa tc                                             22

<210> SEQ ID NO 40
<211> LENGTH: 22
<212> TYPE: DNA
<213> ORGANISM: Homo sapiens

<400> SEQUENCE: 40
cagattttac ttgcatctgg cc                                             22

<210> SEQ ID NO 41
```

```
<211> LENGTH: 22
<212> TYPE: DNA
<213> ORGANISM: Homo sapiens

<400> SEQUENCE: 41
gtggccaggt ggaagtaaaa tc                                            22

<210> SEQ ID NO 42
<211> LENGTH: 22
<212> TYPE: DNA
<213> ORGANISM: Homo sapiens

<400> SEQUENCE: 42
atgaacttca tgctcagctt gc                                            22

<210> SEQ ID NO 43
<211> LENGTH: 22
<212> TYPE: DNA
<213> ORGANISM: Homo sapiens

<400> SEQUENCE: 43
cggcaagctg agcatgaagt tc                                            22

<210> SEQ ID NO 44
<211> LENGTH: 22
<212> TYPE: DNA
<213> ORGANISM: Homo sapiens

<400> SEQUENCE: 44
cagtggcttc tggcacagca gc                                            22

<210> SEQ ID NO 45
<211> LENGTH: 22
<212> TYPE: DNA
<213> ORGANISM: Homo sapiens

<400> SEQUENCE: 45
aagctgctgt gccagaagcc ac                                            22

<210> SEQ ID NO 46
<211> LENGTH: 42
<212> TYPE: DNA
<213> ORGANISM: Homo sapiens

<400> SEQUENCE: 46
gtaagcagag tggctgagga gatgacattt ttccccaaag ag                      42

<210> SEQ ID NO 47
<211> LENGTH: 21
<212> TYPE: DNA
<213> ORGANISM: Homo sapiens

<400> SEQUENCE: 47
cagagtggct gaggagatga c                                             21

<210> SEQ ID NO 48
<211> LENGTH: 21
<212> TYPE: DNA
<213> ORGANISM: Homo sapiens

<400> SEQUENCE: 48
gtgtcatctc ctcagccact c                                             21
```

```
<210> SEQ ID NO 49
<211> LENGTH: 18
<212> TYPE: DNA
<213> ORGANISM: Homo sapiens

<400> SEQUENCE: 49
cagagtggct gagatgac                                                 18

<210> SEQ ID NO 50
<211> LENGTH: 18
<212> TYPE: DNA
<213> ORGANISM: Homo sapiens

<400> SEQUENCE: 50
atgtcatctc agccactc                                                 18

<210> SEQ ID NO 51
<211> LENGTH: 20
<212> TYPE: DNA
<213> ORGANISM: Homo sapiens

<400> SEQUENCE: 51
ctgagatgac attttttcccc                                              20

<210> SEQ ID NO 52
<211> LENGTH: 20
<212> TYPE: DNA
<213> ORGANISM: Homo sapiens

<400> SEQUENCE: 52
ttggggaaaa atgtcatctc                                               20

<210> SEQ ID NO 53
<211> LENGTH: 23
<212> TYPE: DNA
<213> ORGANISM: Homo sapiens

<400> SEQUENCE: 53
gagtggctga gatgacattt ttc                                           23

<210> SEQ ID NO 54
<211> LENGTH: 23
<212> TYPE: DNA
<213> ORGANISM: Homo sapiens

<400> SEQUENCE: 54
gggaaaaatg tcatctcagc cac                                           23

<210> SEQ ID NO 55
<211> LENGTH: 39
<212> TYPE: DNA
<213> ORGANISM: Homo sapiens

<400> SEQUENCE: 55
gtaagcagag tggctgagat gacattttc cccaaagag                           39

<210> SEQ ID NO 56
<211> LENGTH: 60
<212> TYPE: DNA
<213> ORGANISM: Artificial Sequence
<220> FEATURE:
<223> OTHER INFORMATION: A synthetic primer

<400> SEQUENCE: 56
```
caggactagt cttttaggtc aaaaagaaga agctttgtaa ccgttggttt ccgtagtgta    60

<210> SEQ ID NO 57
<211> LENGTH: 64
<212> TYPE: DNA
<213> ORGANISM: Artificial Sequence
<220> FEATURE:
<223> OTHER INFORMATION: A synthetic primer

<400> SEQUENCE: 57
cttcgaaccg gggacctttc gcgtgttagg cgaacgtgat aaccactaca ctacggaaac    60
caac    64

<210> SEQ ID NO 58
<211> LENGTH: 79
<212> TYPE: DNA
<213> ORGANISM: Artificial Sequence
<220> FEATURE:
<223> OTHER INFORMATION: A synthetic primer

<400> SEQUENCE: 58
aaaaaagtgg ccaggtggaa gtaaaatcca agcttcgatt ttacttccac ctggccacct    60
tcgaaccggg gacctttcg    79

<210> SEQ ID NO 59
<211> LENGTH: 77
<212> TYPE: DNA
<213> ORGANISM: Artificial Sequence
<220> FEATURE:
<223> OTHER INFORMATION: A synthetic primer

<400> SEQUENCE: 59
aaaaaaggtg gccagatgga agtaaaccaa gcttcgttta cttccatctg gccacccttc    60
gaaccgggga cctttcg    77

<210> SEQ ID NO 60
<211> LENGTH: 77
<212> TYPE: DNA
<213> ORGANISM: Artificial Sequence
<220> FEATURE:
<223> OTHER INFORMATION: A synthetic primer

<400> SEQUENCE: 60
aaaaaatgaa gtgaagatgg atgcagccaa gcttcgctgc atccatcttc acttcacttc    60
gaaccgggga cctttcg    77

<210> SEQ ID NO 61
<211> LENGTH: 77
<212> TYPE: DNA
<213> ORGANISM: Artificial Sequence
<220> FEATURE:
<223> OTHER INFORMATION: A synthetic primer

<400> SEQUENCE: 61
aaaaaatgaa gtgaatctgg atgcagccaa gcttcgctgc atccagattc acttcacttc    60
gaaccgggga cctttcg    77

<210> SEQ ID NO 62
<211> LENGTH: 18
<212> TYPE: DNA
<213> ORGANISM: Artificial Sequence
<220> FEATURE:
<223> OTHER INFORMATION: A synthetic primer

<400> SEQUENCE: 62
ctatagtgag tcgtatta                                                      18

<210> SEQ ID NO 63
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 63
ggtggccaga tggaagtaaa                                                    20

<210> SEQ ID NO 64
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 64
tgaagtgaat ctggatgcag                                                    20

<210> SEQ ID NO 65
<211> LENGTH: 20
<212> TYPE: DNA
<213> ORGANISM: Artificial Sequence
<220> FEATURE:
<223> OTHER INFORMATION: A synthetic primer

<400> SEQUENCE: 65
aacttcaccc tgagcttgcc                                                    20

<210> SEQ ID NO 66
<211> LENGTH: 20
<212> TYPE: DNA
<213> ORGANISM: Artificial Sequence
<220> FEATURE:
<223> OTHER INFORMATION: A synthetic primer

<400> SEQUENCE: 66
cggcaagctc agggtgaagt                                                    20

<210> SEQ ID NO 67
<211> LENGTH: 20
<212> TYPE: DNA
<213> ORGANISM: Artificial Sequence
<220> FEATURE:
<223> OTHER INFORMATION: A synthetic primer

<400> SEQUENCE: 67
aacttcaggg tcagcttgcc                                                    20

<210> SEQ ID NO 68
<211> LENGTH: 20
<212> TYPE: DNA
<213> ORGANISM: Artificial Sequence
<220> FEATURE:
<223> OTHER INFORMATION: A synthetic primer

<400> SEQUENCE: 68
cggcaagctg accctgaagt                                                    20

<210> SEQ ID NO 69

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 69
aactggactt ccagaagaac                                          20

<210> SEQ ID NO 70
<211> LENGTH: 20
<212> TYPE: DNA
<213> ORGANISM: Artificial Sequence
<220> FEATURE:
<223> OTHER INFORMATION: A synthetic primer

<400> SEQUENCE: 70
tgttcttctg gaagtccagt                                          20

<210> SEQ ID NO 71
<211> LENGTH: 20
<212> TYPE: DNA
<213> ORGANISM: Artificial Sequence
<220> FEATURE:
<223> OTHER INFORMATION: A synthetic primer

<400> SEQUENCE: 71
gtggccagat ggaagtaaaa                                          20

<210> SEQ ID NO 72
<211> LENGTH: 20
<212> TYPE: DNA
<213> ORGANISM: Artificial Sequence
<220> FEATURE:
<223> OTHER INFORMATION: A synthetic primer

<400> SEQUENCE: 72
attttacttc catctggcca                                          20

<210> SEQ ID NO 73
<211> LENGTH: 20
<212> TYPE: DNA
<213> ORGANISM: Artificial Sequence
<220> FEATURE:
<223> OTHER INFORMATION: A synthetic primer

<400> SEQUENCE: 73
ttttacttcc atctggccac                                          20

<210> SEQ ID NO 74
<211> LENGTH: 20
<212> TYPE: DNA
<213> ORGANISM: Artificial Sequence
<220> FEATURE:
<223> OTHER INFORMATION: A synthetic primer

<400> SEQUENCE: 74
aggtggccag atggaagtaa                                          20

<210> SEQ ID NO 75
<211> LENGTH: 20
<212> TYPE: DNA
<213> ORGANISM: Artificial Sequence
<220> FEATURE:
<223> OTHER INFORMATION: A synthetic primer

<400> SEQUENCE: 75
```
tttacttcca tctggccacc                                               20

<210> SEQ ID NO 76
<211> LENGTH: 20
<212> TYPE: DNA
<213> ORGANISM: Artificial Sequence
<220> FEATURE:
<223> OTHER INFORMATION: A synthetic primer

<400> SEQUENCE: 76
gaggtggcca gatggaagta                                               20

<210> SEQ ID NO 77
<211> LENGTH: 20
<212> TYPE: DNA
<213> ORGANISM: Artificial Sequence
<220> FEATURE:
<223> OTHER INFORMATION: A synthetic primer

<400> SEQUENCE: 77
ttacttccat ctggccacct                                               20

<210> SEQ ID NO 78
<211> LENGTH: 23
<212> TYPE: DNA
<213> ORGANISM: Artificial Sequence
<220> FEATURE:
<223> OTHER INFORMATION: A synthetic primer

<400> SEQUENCE: 78
aagtgaagat ggatgcagaa ttc                                           23

<210> SEQ ID NO 79
<211> LENGTH: 23
<212> TYPE: DNA
<213> ORGANISM: Artificial Sequence
<220> FEATURE:
<223> OTHER INFORMATION: A synthetic primer

<400> SEQUENCE: 79
cggaattctg catccatctt cac                                           23

<210> SEQ ID NO 80
<211> LENGTH: 20
<212> TYPE: DNA
<213> ORGANISM: Artificial Sequence
<220> FEATURE:
<223> OTHER INFORMATION: A synthetic primer

<400> SEQUENCE: 80
tgaagtgaag atggatgcag                                               20

<210> SEQ ID NO 81
<211> LENGTH: 20
<212> TYPE: DNA
<213> ORGANISM: Artificial Sequence
<220> FEATURE:
<223> OTHER INFORMATION: A synthetic primer

<400> SEQUENCE: 81
tctgcatcca tcttcacttc                                               20

<210> SEQ ID NO 82
<211> LENGTH: 20
<212> TYPE: DNA

```
<213> ORGANISM: Artificial Sequence
<220> FEATURE:
<223> OTHER INFORMATION: A synthetic primer

<400> SEQUENCE: 82
aagtgaatct ggatgcagaa                                                  20

<210> SEQ ID NO 83
<211> LENGTH: 20
<212> TYPE: DNA
<213> ORGANISM: Artificial Sequence
<220> FEATURE:
<223> OTHER INFORMATION: A synthetic primer

<400> SEQUENCE: 83
attctgcatc cagattcact                                                  20

<210> SEQ ID NO 84
<211> LENGTH: 20
<212> TYPE: DNA
<213> ORGANISM: Artificial Sequence
<220> FEATURE:
<223> OTHER INFORMATION: A synthetic primer

<400> SEQUENCE: 84
gaagtgaatc tggatgcaga                                                  20

<210> SEQ ID NO 85
<211> LENGTH: 20
<212> TYPE: DNA
<213> ORGANISM: Artificial Sequence
<220> FEATURE:
<223> OTHER INFORMATION: A synthetic primer

<400> SEQUENCE: 85
ttctgcatcc agattcactt                                                  20

<210> SEQ ID NO 86
<211> LENGTH: 20
<212> TYPE: DNA
<213> ORGANISM: Artificial Sequence
<220> FEATURE:
<223> OTHER INFORMATION: A synthetic primer

<400> SEQUENCE: 86
tctgcatcca gattcacttc                                                  20

<210> SEQ ID NO 87
<211> LENGTH: 20
<212> TYPE: DNA
<213> ORGANISM: Artificial Sequence
<220> FEATURE:
<223> OTHER INFORMATION: A synthetic primer

<400> SEQUENCE: 87
ctgaagtgaa tctggatgca                                                  20

<210> SEQ ID NO 88
<211> LENGTH: 20
<212> TYPE: DNA
<213> ORGANISM: Artificial Sequence
<220> FEATURE:
<223> OTHER INFORMATION: A synthetic primer

<400> SEQUENCE: 88
ctgcatccag attcacttca                                                  20
```

```
<210> SEQ ID NO 89
<211> LENGTH: 20
<212> TYPE: DNA
<213> ORGANISM: Artificial Sequence
<220> FEATURE:
<223> OTHER INFORMATION: A synthetic primer

<400> SEQUENCE: 89
tctgaagtga atctggatgc                                              20

<210> SEQ ID NO 90
<211> LENGTH: 20
<212> TYPE: DNA
<213> ORGANISM: Artificial Sequence
<220> FEATURE:
<223> OTHER INFORMATION: A synthetic primer

<400> SEQUENCE: 90
tgcatccaga ttcacttcag                                              20
```